(12) United States Patent
Ahmed et al.

(10) Patent No.: US 8,691,811 B2
(45) Date of Patent: Apr. 8, 2014

(54) QUINAZOLINONE LINKED PYRROLO[2,1-C][1,4]BENZODIAZEPINE HYBRIDS AS POTENTIAL ANTICANCER AGENTS AND PROCESS FOR THE PREPARATION THEREOF

(75) Inventors: Kamal Ahmed, Hyderabad (IN); Earla V. Bharathi, Hyderabad (IN); Dudekula Dastagiri, Hyderabad (IN); Jonnala S. Reddy, Hyderabad (IN); Arutla Viswanath, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 50 days.

(21) Appl. No.: 13/129,995

(22) PCT Filed: Jul. 13, 2009

(86) PCT No.: PCT/IN2009/000400
§ 371 (c)(1),
(2), (4) Date: Jan. 3, 2012

(87) PCT Pub. No.: WO2010/058416
PCT Pub. Date: May 27, 2010

(65) Prior Publication Data
US 2012/0095214 A1     Apr. 19, 2012

(30) Foreign Application Priority Data

Nov. 19, 2008    (IN) ................. 2598/DEL/2008

(51) Int. Cl.
    C07D 487/04      (2006.01)
    A61K 31/5517     (2006.01)
(52) U.S. Cl.
    USPC ................................. 514/220; 540/456
(58) Field of Classification Search
    USPC ........................... 540/456; 514/220
    See application file for complete search history.

(56) References Cited

U.S. PATENT DOCUMENTS 5,922,866 A    7/1999   Miyata
6,683,073 B1   1/2004   Kamal

FOREIGN PATENT DOCUMENTS

WO    WO 2008/020456    2/2008

OTHER PUBLICATIONS

Design and Synthesis of C-8 Linked Pyrrolobenzodiazepine-Naphthalimide Hybrids as Anti-Tumor Agents, Kamal, Ahmed et al., Bioorganic & Medicinal Chemistry Letters, Pergamon, vol. 12, No. 15, May 6, 2002.

*Primary Examiner* — Bruck Kifle
(74) *Attorney, Agent, or Firm* — Edwards Wildman Palmer LLP; Barry Kramer; Nicholas J. DiCeglie, Jr.

(57) ABSTRACT

The present invention provides a compound of general formulae 5a-r, 9a-i to 13a-i and 17a-i to 22a-i, useful as potential antitumour agents against human cancer cell lines. The present invention further provides a process for the preparation of pyrrolo[2,1-c][1,4]benzodiazepine hybrids of general formulae 5a-r, 9a-i to 13a-i and 17a-i to 22a-i.

Formula 5a-r n = 1-9
R = Methyl, styryl

Formula 9a-i to 13a-i n = 1-9
R = alkyl, aryl
X, Y, Z = halo, alkyl, alkoxy

Formula 17a-i to 22a-i n = 1-9
R = Phenyl
$R_1$ = Hydrogen, halo, pyrrolidine, piperidine
4-methyl piperidine, morpholine

4 Claims, No Drawings

QUINAZOLINONE LINKED PYRROLO[2,1-C][1,4]BENZODIAZEPINE HYBRIDS AS POTENTIAL ANTICANCER AGENTS AND PROCESS FOR THE PREPARATION THEREOF

CROSS REFERENCE TO RELATED APPLICATIONS

This Application is a U.S. National Stage Application pursuant to 35 U.S.C. §371 of International Application No. PCT/IN2009/000400, filed Jul. 13, 2009, and amended under PCT Article 19 on Feb. 27, 2010, which claims the benefit of priority of Indian Patent Application No. 2598/DEL/2008, filed Nov. 19, 2008, the disclosures of each of which are expressly incorporated by reference in their entireties.

FIELD OF THE INVENTION

The present invention relates to quinazolinone linked pyrrolo[2,1-c][1,4]benzodiazepine hybrids as anticancer agents. Particularly, the present invention relates to quinazolinone linked pyrrolo[2,1-c][1,4]benzodiazepine hybrids of general formula A.

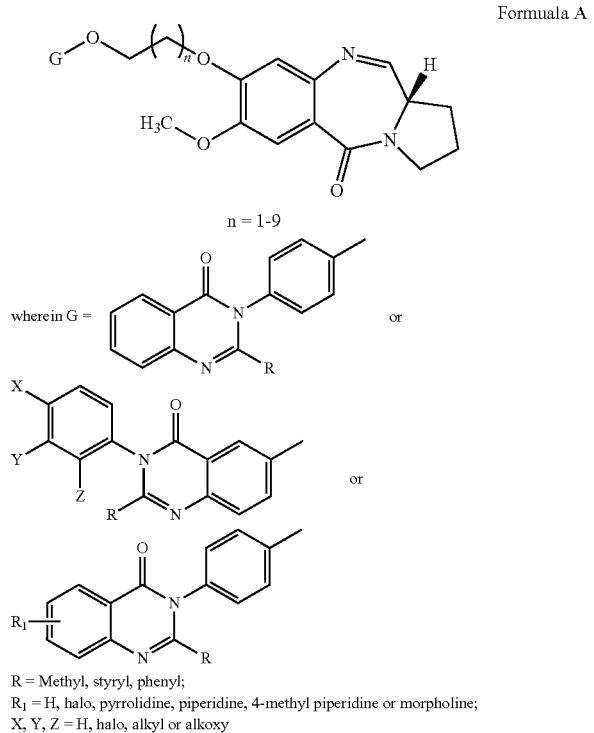

R = Methyl, styryl, phenyl;
$R_1$ = H, halo, pyrrolidine, piperidine, 4-methyl piperidine or morpholine;
X, Y, Z = H, halo, alkyl or alkoxy More particularly, the present invention relates to 7-methoxy-8{-n-[4-(2-alkyl/aryl/styryl-4-oxo-3,4-dihydro-3-quinazolinyl)phenoxy]alkyloxy}-(11aS)-1,2,3,11a-tetrahydro-5H-pyrrolo[2,1-c][1,4]benzodiazepin-5-one, 7-methoxy-8-{n-[3-aryl-2-alkyl/aryl-4-oxo-3,4-dihydro-6-quinazolinyl]oxyalkyloxy}-(11aS)-1,2,3,11a-tetrahydro-5H-pyrrolo[2,1-c][1,4]benzodiazepin-5-one and 7-methoxy-8-[n-(4-[6-halo/pyrrolidine-2-alkyl/aryl-3,4-dihydro-3-quinazolinyl]phenyloxy)alkyl]oxy]-(11aS))-1,2,3,11a-tetrahydro-5H-pyrrolo[2,1-c][1,4]benzodiazepin-5-one with aliphatic chain length variations useful as anticancer (antitumour) agents. The structural formulae of these quinazolinone linked pyrrolo[2,1-c][1,4]benzodiazepine hybrids is given below and is represented by the following compounds of formula 5a-r, 9a-i to 13a-i and 17a-i to 22a-i.

Formula 5a-r

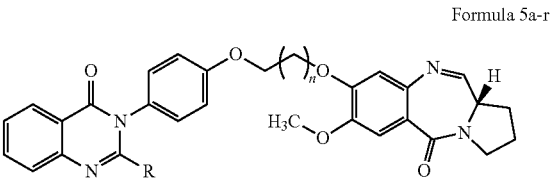

n = 1-9
R = Methyl, styryl

Formula 9a-i to 13a-i

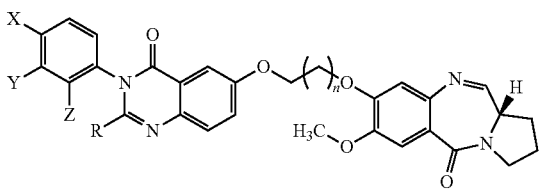

n = 1-9
R = alkyl, aryl
X, Y, Z = halo, alkyl, alkoxy

Formula 17a-i to 22a-i

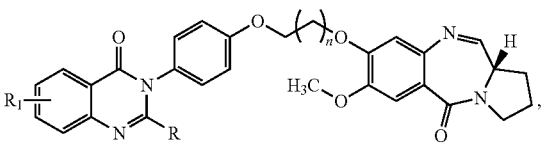

n = 1-9
R = Phenyl
$R_1$ = Hydrogen, halo, pyrrolidine, piperidine 4-methyl piperidine, morpholine

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.,* 1980, 33, 665.; Kohn, K. W. and Speous, C. L. *J. Mol. Biol.,* 1970, 51, 551.; Hurley, L. H.; Gairpla, C. and Zmijewski, M. *Biochem. Biophys. Acta.,* 1977, 475, 521.; Kaplan, D. J. and Hurley, L. H. *Biochemistry,* 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. *J. Org. Chem.* 1996, 61, 8141).

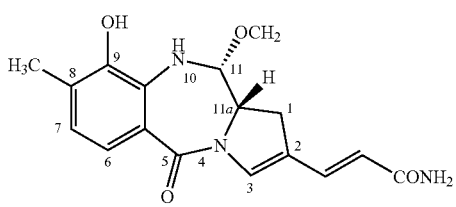

anthramycin

DC-81

Napthalimide-PBD hybrid
n = 1-9

Benzothiazole-PBD hybrid
n = 1-9

Benzimidazole-PBD hybrid
n = 1-9 sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main objective of the present invention is to provide novel quinazolinone linked pyrrolo[2,1-c][1,4]benzodiazepine hybrids, useful as antitumour agents.

Yet another object of this invention is to provide a process for the preparation of novel quinazolinone linked pyrrolo[2,1-c][1,4]benzodiazepine hybrids.

SUMMARY OF THE INVENTION

Accordingly the present invention provides novel quinazolinone linked pyrrolo[2,1-c][1,4]benzodiazepine hybrids of general formulae A Formula A

n = 1-9

Recently, PBD dimers have been developed that comprise of two C2-exo-methylene substituted DC-81 subunits tethered through their C-8 position via an inert propanedioxy linker (Gregson, S. J.; Howard, P. W.; Hartely, J, A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity. (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific wherein G =

or

R = Methyl, styryl, phenyl;
$R_1$ = H, halo, pyrrolidine, piperidine, 4-methyl piperidine or morpholine;
X, Y, Z = H, halo, alkyl or alkoxy In an embodiment of the present invention the novel quinazolinone linked pyrrolo[2,1-c][1,4]benzodiazepine hybrids of formula A is represented by the compounds of general formulae 5a-r, 9a-i to 13a-i and 17a-i to 22a-i.

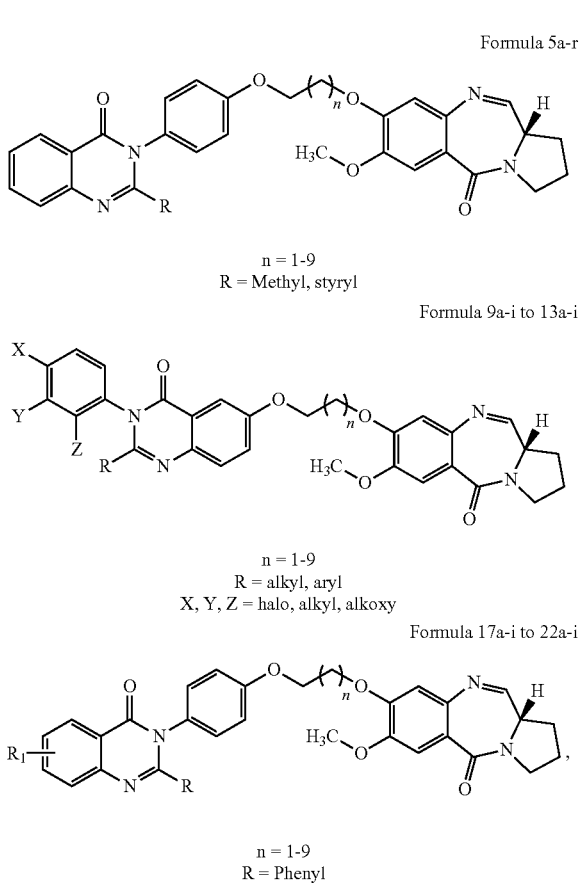

Formula 5a-r n = 1-9
R = Methyl, styryl

Formula 9a-i to 13a-i n = 1-9
R = alkyl, aryl
X, Y, Z = halo, alkyl, alkoxy

Formula 17a-i to 22a-i n = 1-9
R = Phenyl
$R_1$ = Hydrogen, halo, pyrrolidine, piperidine
4-methyl piperidine, morpholine In yet another embodiment the Quinazolinone linked pyrrolo[2,1-c][1,4]benzodiazepine hybrids is represented by the group of the following compounds:

7-methoxy-8{-2-[4-(2-methyl-4-oxo-3,4-dihydro-3-quinazolinyl)phenoxy]ethoxy}-(11aS)-1,2,3,11a-tetrahydro-5H-pyrrolo[2,1-c][1,4]benzodiazepine-5-one (5a);

7-methoxy-8{-3-[4-(2-methyl-4-oxo-3,4-dihydro-3-quinazolinyl)phenoxy]propoxy}-(11aS)-1,2,3,11a-tetrahydro-5H-pyrrolo[2,1-c][1,4]benzodiazepine-5-one (5b);

7-methoxy-8{-4-[4-(2-methyl-4-oxo-3,4-dihydro-3-quinazolinyl)phenoxy]butoxy-}-(11aS)-1,2,3,11a-tetrahydro-5H-pyrrolo[2,1-c][1,4]benzodiazepine-5-one (5c);

7-methoxy-8-{5-[4-(2-methyl-4-oxo-3,4-dihydro-3-quinazolinyl)phenoxy]pentyloxy-}-(11aS)-1,2,3,11a-tetrahydro-5H-pyrrolo[2,1-c][1,4]benzodiazepine-5-one (5d);

7-methoxy-8{-6-[4-(2-methyl-4-oxo-3,4-dihydro-3-quinazolinyl)phenoxy]hexyloxy}-(11aS)-1,2,3,11a-tetrahydro-5H-pyrrolo[2,1-c][1,4]benzodiazepine-5-one (5e);

7-methoxy-8{-7-[4-(2-methyl-4-oxo-3,4-dihydro-3-quinazolinyl)phenoxy]heptyloxy-}-(11aS)-1,2,3,11a-tetrahydro-5H-pyrrolo[2,1-c][1,4]benzodiazepine-5-one (5f);

7-methoxy-8-{-8-[4-(2-methyl-4-oxo-3,4-dihydro-3-quinazolinyl)phenoxy]octyloxy-}-(11aS)-1,2,3,11a-tetrahydro-5H-pyrrolo[2,1-c][1,4]benzodiazepine-5-one (5g);

7-methoxy-8{-9-[4-(2-methyl-4-oxo-3,4-dihydro-3-quinazolinyl)phenoxy]nonyloxy}-(11aS)-1,2,3,11a-tetrahydro-5H-pyrrolo[2,1-c][1,4]benzodiazepine-5-one (5h);

7-methoxy-8{-10-[4-(2-methyl-4-oxo-3,4-dihydro-3-quinazolinyl)phenoxy]decyloxy-}-(11aS)-1,2,3,11a-tetrahydro-5H-pyrrolo[2,1-c][1,4]benzodiazepine-5-one (5i);

7-methoxy-8-{-2-[(4-4-oxo-2-[(E)-2-phenyl-1-ethenyl]-3,4-dihydro-3-quinazolinylphenyl)oxy]ethoxy}-(11aS)-1,2,3,11a-tetrahydro-5H-pyrrolo[2,1-c][1,4]benzodiazepine-5-one (5j);

7-methoxy-8-{3-[(4-4-oxo-2-[(E)-2-phenyl-1-ethenyl]-3,4-dihydro-3-quinazolinylphenyl)oxy]propoxy}-(11aS)-1,2,3,11a-tetrahydro-5H-pyrrolo[2,1-c][1,4]benzodiazepine-5-one (5k);

7-methoxy-8-{4-[(4-4-oxo-2-[(E)-2-phenyl-1-ethenyl]-3,4-dihydro-3-quinazolinylphenyl)oxy]butoxy}-(11aS)-1,2,3,11a-tetrahydro-5H-pyrrolo[2,1-c][1,4]benzodiazepine-5-one (5l);

7-methoxy-8-{5-[(4-4-oxo-2-[(E)-2-phenyl-1-ethenyl]-3,4-dihydro-3-quinazolinylphenyl)oxy]pentyloxy}-(11aS)-1,2,3,11a-tetrahydro-5H-pyrrolo[2,1-c][1,4]benzodiazepine-5-one (5m);

7-methoxy-8-{-6-[(4-4-oxo-2-[(E)-2-phenyl-1-ethenyl]-3,4-dihydro-3-quinazolinylphenyl)oxy]hexyloxy}-(11aS)-1,2,3,11a-tetrahydro-5H-pyrrolo[2,1-c][1,4]benzodiazepine-5-one (5n);

7-methoxy-8-{-7-[(4-4-oxo-2-[(E)-2-phenyl-1-ethenyl]-3,4-dihydro-3-quinazolinylphenyl)oxy]heptyloxy}-(11aS)-1,2,3,11a-tetrahydro-5H-pyrrolo[2,1-c][1,4]benzodiazepine-5-one (5o);

7-methoxy-8-{-8-[(4-4-oxo-2-[(E)-2-phenyl-1-ethenyl]-3,4-dihydro-3-quinazohnylphenyl)oxy]octyloxy}-(11aS)-1,2,3,11a-tetrahydro-5H-pyrrolo[2,1-c][1,4]benzodiazepine-5-one (5p);

7-methoxy-8-{-9-[(4-4-oxo-2-[(E)-2-phenyl-1-ethenyl]-3,4-dihydro-3-quinazolinylphenyl)oxy]nonylyloxy}-(11aS)-1,2,3,11a-tetrahydro-5H-pyrrolo[2,1-c][1,4]benzodiazepine-5-one (5q);

7-methoxy-8-{-10-[(4-4-oxo-2-[(E)-2-phenyl-1-ethenyl]-3,4-dihydro-3-quinazolinylphenyl)oxy]nonylyloxy}-(11aS)-1,2,3,11a-tetrahydro-5H-pyrrolo[2,1-c][1,4]benzodiazepine-5-one (5r);

7-methoxy-8-{-2-[3-(4-fluorophenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (9a);

7-methoxy-8-{3-[3-(4-fluorophenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (9b);

7-methoxy-8-{4-[3-(4-fluorophenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (9c);

7-methoxy-8-{5-[3-(4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (9d);

7-methoxy-8-{6-[3-(4-fluorophenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (9e);

7-methoxy-8-{7-[3-(4-fluorophenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (9f);

7-methoxy-8-{8-[3-(4-fluorophenyl)-2-methyl-4-oxo-3,4-dihydro-6-quinazolinyl]oxyootyloxy}-(11aS)-1,2,3,11a-tetrahydro-5H-pyrrolo[2,1-c][1,4]benzodiazepine-5-one (9g);

7-methoxy-8-{9-[3-(4-fluorophenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (9h);

7-methoxy-8-[10-[3-(4-fluorophenyl)-2-methyl-4-oxo-3,4-dihydro-6-quinazolinyl]oxydecyloxy]-(11aS)-1,2,3,11a-tetrahydro-5H-pyrrolo[2,1-c][1,4]benzodiazepine-5-one (9i);

benzodiazepine-5-one (9j);

7-methoxy-8-{2-[3-(3-chloro-4-fluorophenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (10a);

7-methoxy-8-{3-[3-(3-chloro-4-fluorophenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (10b);

7-methoxy-8-{4-[3-(3-chloro-4-fluorophenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (10c);

7-methoxy-8-{5-[3-(3-chloro-4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (10d);

7-methoxy-8-{6-[3-(3-chloro-4-fluorophenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (10e);

7-methoxy-8-{7-[3-(3-chloro-4-fluorophenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (10f);

7-methoxy-8-{8-[3-(3-chloro-4-fluorophenyl)-2-methyl-4-oxo-3,4-dihydro-6-quinazolinyl]oxyoctyloxy}-(11aS)-1,2,3,11a-tetrahydro-5H-pyrrolo[2,1-c][1,4]benzodiazepine-5-one (10g);

7-methoxy-8-{9-[3-(3-chloro-4-fluorophenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (10h);

7-methoxy-8-{10-[3-(3-chloro-4-fluorophenyl)-2-methyl-4-oxo-3,4-dihydro-6-quinazolinyl]oxydecyloxy}-(11aS)-1,2,3,11a-tetrahydro-5H-pyrrolo[2,1-c][1,4]benzodiazepine-5-one (10i);

7-methoxy-8-{(2-[3-(4-methoxyphenyl)-2-methyl-4-oxo-3,4-dihydro-6-quinazolinyl]oxyethoxy}-(11aS)-1,2,3,11a-tetrahydro-5H-pyrrolo [2,1-c][1,4]benzodiazepine-5-one (11a);

7-methoxy-8-{(3-[3-(4-methoxyphenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (11b);

7-methoxy-8-{(4-[3-(4-methoxyphenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (11c);

7-methoxy-8-{(5-[3-(4-methoxyphenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (11d);

7-methoxy-8-{(6-[3-(4-methoxyphenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (11e);

7-methoxy-8-{(7-[3-(4-methoxyphenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (11f);

7-methoxy-8-{(8-[3-(4-methoxyphenyl)-2-methyl-4-oxo-3,4-dihydro-6-quinazolinyl]oxyoctyloxy}-(11aS)-1,2,3,11a-tetrahydro-5H-pyrrolo[2,1-c][1,4]benzodiazepine-5-one (11g);

7-methoxy-8-{(9-[3-(4-methoxyphenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (11h);

7-methoxy-8-{(10-[3-(4-methoxyphenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (11i);

7-methoxy-8-{2-[3-(4-iodo-2-methylphenyl)-2-methyl-4-oxo-34-dihydro-6-quinazolinyl]oxyethoxy}-(11aS)-1,2,3,11a-tetrahydro-5H-pyrrolo[2,1-c][1,4]benzodiazepine-5-one (12a);

7-methoxy-8-{3-[3-(4-iodo-2-methylphenyl)-2-methyl-4-oxo-34-dihydro-6-quinazolinyl]oxypropoxy}-(11aS)-1,2,3,11a-tetrahydro-5H-pyrrolo[2,1-c][1,4]benzodiazepine-5-one (12b);

7-methoxy-8-{4-[3-(4-iodo-2-methylphenyl)-2-methyl-4-oxo-34-dihydro-6-quinazolinyl]oxybutoxy}-(11aS)-1,2,3,11a-tetrahydro-5H-pyrrolo[2,1-c][1,4]benzodiazepine-5-one (12c);

7-methoxy-8-{5-[3-(4-iodo-2-methylphenyl)-2-methyl-4-oxo-34-dihydro-6-quinazolinyl]oxypentyloxy}-(11aS)-1,2,3,11a-tetrahydro-5H-pyrrolo[2,1-c][1,4]benzodiazepine-5-one (12d);

7-methoxy-8-{6-[3-(4-iodo-2-methylphenyl)-2-methyl-4-oxo-34-dihydro-6-quinazolinyl]oxyhexyloxy}-(11aS)-1,2,3,11a-tetrahydro-5H-pyrrolo[2,1-c][1,4]benzodiazepine-5-one (12e);

7-methoxy-8-{7-[3-(4-iodo-2-methylphenyl)-2-methyl-4-oxo-34-dihydro-6-quinazolinyl]oxyheptyloxy}-(11aS)-1,2,3,11a-tetrahydro-5H-pyrrolo[2,1-c][1,4]benzodiazepine-5-one (12f);

7-methoxy-8-{8-[3-(4-iodo-2-methylphenyl)-2-methyl-4-oxo-34-dihydro-6-quinazolinyl]oxyoctyloxy}-(11aS)-1,2,3,11a-tetrahydro-5H-pyrrolo[2,1-c][1,4]benzodiazepine-5-one (12g);

7-methoxy-8-{9-[3-(4-iodo-2-methylphenyl)-2-methyl-4-oxo-34-dihydro-6-quinazolinyl]oxynonyloxy}-(11aS)-1,2,3,11a-tetrahydro-5H-pyrrolo[2,1-c][1,4]benzodiazepine-5-one (12h);

7-methoxy-8-{10-[3-(4-iodo-2-methylphenyl)-2-methyl-4-oxo-34-dihydro-6-quinazolinyl]oxydecyloxy}-(11aS)-1,2,3,11a-tetrahydro-5H-pyrrolo[2,1-c][1,4]benzodiazepine-5-one (12i);

7-methoxy-8-{2-[3-(2,4-dichlorophenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (13a);

7-methoxy-8-{3-[3-(2,4-dichlorophenyl)-2-methyl-4-oxo-3, 4-dihydro-6-quinazolinyl]oxypropoxy}-(11aS)-1,2,3, 11a-tetrahydro-5H-pyrrolo[2,1-c][1,4]benzodiazepine-5-one (13b);

7-methoxy-8-{4-[3-(2,4-dichlorophenyl)-2-methyl-4-oxo-3, 4-dihydro-6-quinazolinyl]oxybutoxy}-(11aS)-1,2,3,11a-tetrahydro-5H-pyrrolo[2,1-c][1,4]benzodiazepine-5-one (13c);

7-methoxy-8-{5-[3-(2,4-dichlorophenyl)-2-methyl-4-oxo-3, 4-dihydro-6-quinazolinyl]oxypentyloxy}-(11aS)-1,2,3, 11a-tetrahydro-5H-pyrrolo[2,1-c][1,4]benzodiazepine-5-one (13d);

7-methoxy-8-{5-[3-(2,4-dichlorophenyl)-2-methyl-4-oxo-3, 4-dihydro-6-quinazolinyl]oxyhexyloxy}-(11aS)-1,2,3, 11a-tetrahydro-5H-pyrrolo [2,1-c][1,4]benzodiazepine-5-one (13e);

7-methoxy-8-{7-[3-(2,4-dichlorophenyl)-2-methyl-4-oxo-3, 4-dihydro-6-quinazolinyl]oxyheptyloxy}-(11aS)-1,2,3, 11a-tetrahydro-5H-pyrrolo[2,1-c][1,4]benzodiazepine-5-one (13f);

7-methoxy-8-{8-[3-(2,4-dichlorophenyl)-2-methyl-4-oxo-3, 4-dihydro-6-quinazolinyl]oxyoctyloxy}-(11aS)-1,2,3, 11a-tetrahydro-5H-pyrrolo[2,1-c][1,4]benzodiazepine-5-one (13g);

7-methoxy-8-{9-[3-(2,4-dichlorophenyl)-2-methyl-4-oxo-3, 4-dihydro-6-quinazolinyl]oxynonyloxy}-(11aS)-1,2,3, 11a-tetrahydro-5H-pyrrolo[2,1-c][1,4]benzodiazepine-5-one (13h);

7-methoxy-8-{10-[3-(2,4-dichlorophenyl)-2-methyl-4-oxo-3,4-dihydro-6-quinazolinyl]oxydecyloxy}-(11aS)-1,2,3, 11a-tetrahydro-5H-pyrrolo[2,1-c][1,4]benzodiazepine-5-one (13i);

7-(methoxy)-3-[(2-[4-(4-oxo-2-phenyl-3,4-dihydro-3-quinazolinyl)phenyl]oxyethyl)oxy]-(11aS)-1,2,3,11a-tetrahydro-5H-[pyrrolo[2,1-c][1,4]benzodiazepin-5-one (17a);

7-(methoxy)-8-[(3-[4-(4-oxo-2-phenyl-3,4-dihydro-3-quinazolinyl)phenyl]oxypropyl)oxy]-(11aS)-1,2,3,11a-tetrahydro-5H-pyrrolo[2,1-c][1,4]benzodiazepin-5-one (17b);

7-(methoxy)-8-[(4-[4-(4-oxo-2-phenyl-3,4-dihydro-3-quinazolinyl)phenyl]oxypropyl)oxy]-(11aS)-1,2,3,11a-tetrahydro-5H-pyrrolo[2,1-c][1,4]benzodiazepin-5-one (17c);

7-(methoxy)-8-[(5-[4-(4-oxo-2-phenyl-3,4-dihydro-3-quinazolinyl)phenyl]oxypentyl)oxy]-(11aS)-1,2,3,11a-tetrahydro-5H-pyrrolo[2,1-c][1,4]benzodiazepin-5-one (17d);

7-(methoxy)-8-[(6-[4-(4-oxo-2-phenyl-3,4-dihydro-3-quinazolinyl)phenyl]oxyhexyl)oxy]-(11aS)-1,2,3,11a-tetrahydro-5H-pyrrolo[2,1-c][1,4]benzodiazepin-5-one (17e);

7-(methoxy)-8-[(7-[4-(4-oxo-2-phenyl-3,4-dihydro-3-quinazolinyl)phenyl]oxyheptyl)oxy]-(11aS)-1,2,3,11a-tetrahydro-5H-pyrrolo[2,1-c][1,4]benzodiazepin-5-one (17f);

7-(methoxy)-8-[(8-[4-(4-oxo-2-phenyl-3,4-dihydro-3-quinazolinyl)phenyl]oxyoctyl)oxy]-(11aS)-1,2,3,11a-tetrahydro-5H-pyrrolo[2,1-c][1,4]benzodiazepin-5-one (17g);

7-(methoxy)-8-[(9-[4-(4-oxo-2-phenyl-3,4-dihydro-3-quinazolinyl)phenyl]oxynonyl)oxy]-(11aS)-1,2,3,11a-tetrahydro-5H-[pyrrolo[2,1-c][1,4]benzodiazepin-5-one (17h);

7-(methoxy)-8-[(10-[4-(4-oxo-2-phenyl-3,4-dihydro-3-quinazolinyl)phenyl]oxydecyl)oxy]-(11aS)-1,2,3,11a-tetrahydro-5H-[pyrrolo[2,1-c][1,4]benzodiazepin-5-one (17i);

7-methoxy-(8-[(2-[4-(6-chloro-4-oxo-2-phenyl-3,4-dihydro-3-quinazolinyl)phenyl]oxyethyl)oxy]-(11aS)-1,2,3, 11a-tetrahydro-5H-pyrrolo[2,1-c][1,4]benzodiazepin-5-one (18a);

7-methoxy-(8-[(3-[4-(6-chloro-4-oxo-2-phenyl-3,4-dihydro-3-quinazolinyl) phenyl]oxypropyl)oxy]-(11aS)-1,2,3, 11a-tetrahydro-5H-pyrrolo[2,1-c][1,4]benzodiazepin-5-one (18b);

7-methoxy-(8-[(4-[4-(6-chloro-4-oxo-2-phenyl-3,4-dihydro-3-quinazolinyl)phenyl]oxybutyl)oxy]-(11aS)-1,2,3, 11a-tetrahydro-5H-pyrrolo[2,1-c][1,4]benzodiazepin-5-one (18c);

7-methoxy-(8-[(5-[4-(6-chloro-4-oxo-2-phenyl-3,4-dihydro-3-quinazolinyl)phenyl]oxypentyl)oxy-(11aS)-1,2,3, 11a-tetrahydro-5H-pyrrolo[2,1-c][1,4]benzodiazepin-5-one (18d);

7-methoxy-(8-[(6-[4-(6-chloro-4-oxo-2-phenyl-3,4-dihydro-3-quinazolinyl)phenyl]oxyhexyl)oxy]-(11aS)-1,2,3, 11a-tetrahydro-5H-pyrrolo[2,1-c][1,4]benzodiazepin-5-one (18e);

7-methoxy-(8-[(7-[4-(6-chloro-4-oxo-2-phenyl-3,4-dihydro-3-quinazolinyl) phenyl]oxyheptyl)oxy]-(11aS)-1,2,3, 11a-tetrahydro-5H-pyrrolo[2,1-c][1,4]benzodiazepin-5-one (18f);

7-methoxy-(8-[(8-[4-(6-chloro-4-oxo-2-phenyl-3,4-dihydro-3-quinazolinyl)phenyl]oxyoctyl)oxy]-(11aS)-1,2,3, 11a-tetrahydro-5H-pyrrolo[2,1-c][1,4]benzodiazepin-5-one (18g);

7-methoxy-(8-[(9-[4-(6-chloro-4-oxo-2-phenyl-3,4-dihydro-3-quinazolinyl)phenyl]oxynonyl)oxy]-(11aS)-1,2,3, 11a-tetrahydro-5H-pyrrolo[2,1-c][1,4]benzodiazepin-5-one (18h);

7-methoxy-(8-[(10-[4-(6-chloro-4-oxo-2-phenyl-3,4-dihydro-3-quinazolinyl)phenyl]oxydecyl)oxy]-(11aS)-1,2,3, 11a-tetrahydro-5H-pyrrolo[2,1-c][1,4]benzodiazepin-5-one (18i);

7-methoxy-8-[(2-[4-(4-oxo-2-phenyl-6-tetrahydro-1H-1-pyrrolyl-3,4-dihydro-3-quinazolinyl)phenyl]oxyethyl) oxy]-(11aS)-1,2,3,11a-tetrahydro-5H-pyrrolo[2,1-c][1,4] benzodiazepin-5-one (19a);

7-methoxy-8-[(3-[4-(4-oxo-2-phenyl-6-tetrahydro-1H-1-pyrrolyl-3,4-dihydro-3-quinazolinyl)phenyl]oxypropyl) oxy]-(11aS)-1,2,3,11a-tetrahydro-5H-pyrrolo[2,1-c][1,4] benzodiazepin-5-one (19b);

7-methoxy-8-[(4-[4-(4-oxo-2-phenyl-6-tetrahydro-1H-1-pyrrolyl-3,4-dihydro-3-quinazolinyl)phenyl]oxybutyl) oxy]-(11aS)-1,2,3,11a-tetrahydro-5H-pyrrolo[2,1-c][1,4] benzodiazepin-5-one (19c);

7-methoxy-8-[(5-[4-(4-oxo-2-phenyl-6-tetrahydro-1H-1-pyrrolyl-3,4-dihydro-3-quinazolinyl)phenyl]oxypentyl) oxy]-(11aS)-1,2,3,11a-tetrahydro-5H-pyrrolo[2,1-c][1,4] benzodiazepin-5-one (19d);

7-methoxy-8-[(6-[4-(4-oxo-2-phenyl-6-tetrahydro-1H-1-pyrrolyl-3,4-dihydro-3-quinazolinyl)phenyl]oxyhexyl) oxy]-(11aS)-1,2,3,11a-tetrahydro-5H-pyrrolo[2,1-c][1,4] benzodiazepin-5-one (19e);

7-methoxy-8-[(7-[4-(4-oxo-2-phenyl-6-tetrahydro-1H-1-pyrrolyl-3,4-dihydro-3-quinazolinyl)phenyl]oxyheptyl) oxy]-(11aS)-1,2,3,11a-tetrahydro-5H-pyrrolo[2,1-c][1,4] benzodiazepin-5-one (19f);

7-methoxy-8-[(8-[4-(4-oxo-2-phenyl-6-tetrahydro-1H-1-pyrrolyl-3,4-dihydro-3-quinazolinyl)phenyl]oxyoctyl)oxy]-(11aS)-1,2,3,11a-tetrahydro-5H-pyrrolo[2,1-F][1,4]benzodiazepin-5-one (19g);

7-methoxy-8-[(9-[4-(4-oxo-2-phenyl-6-tetrahydro-1H-1-pyrrolyl-3,4-dihydro-3-quinazolinyl)phenyl]oxynonyl)oxy]-(11aS)-1,2,3,11a-tetrahydro-5H-pyrrolo[2,1-c][1,4]benzodiazepin-5-one (19h);

7-methoxy-8-[(10-[4-(4-oxo-2-phenyl-6-tetrahydro-1H-1-pyrrolyl-3,4-dihydro-8-quinazolinyl)phenyl]oxydecyl)oxy]-(11aS)-1,2,3,11a-tetrahydro-5H-pyrrolo[2,1-c][1,4]benzodiazepin-5-one (19i);

7-methoxy-8-[(2-[4-(6-hexahydro-1-pyridinyl-4-oxo-2-phenyl-3,4-dihydro-3-quinazolinyl)phenyl]oxyethyl)oxy]-(11aS))-1,2,3,11a-tetrahydro-5H-pyrrolo[2,1-c][1,4]benzodiazepin-5-one (20a);

7-methoxy-8-[(3-[4-(6-hexahydro-1-pyridinyl-4-oxo-2-phenyl-3,4-dihydro-3-quinazolinyl)phenyl]oxypropyl)oxy]-(11aS))-1,2,3,11a-tetrahydro-5H-pyrrolo[2,1-c][1,4]benzodiazepin-5-one (20b);

7-methoxy-8-[(4-[4-(6-hexahydro-1-pyridinyl-4-oxo-2-phenyl-3,4-dihydro-3-quinazolinyl)phenyl]oxybutyl)oxy]-(11aS))-1,2,3,11a-tetrahydro-5H-pyrrolo [2,1-c][1,4] benzo diazepin-5-one (20c);

7-methoxy-8-[5-[4-(6-hexahydro-1-pyridinyl-4-oxo-2-phenyl-3,4-dihydro-3-quinazolinyl)phenyl]oxypentyl)oxy]-(11aS))-1,2,3,11a-tetrahydro-5H-pyrrolo[2,1-c][1,4]benzodiazepin-5-one (20d);

7-methoxy-8-[(6-[4-(6-hexahydro-1-pyridinyl-4-oxo-2-phenyl-3,4-dihydro-3-quinazolinyl)phenyl]oxyhexyl)oxy]-(11aS))-1,2,3,11a-tetrahydro-5H-pyrrolo[2,1-c][1,4]benzodiazepin-5-one (20e);

7-methoxy-8-[7-[4-(6-hexahydro-1-pyridinyl-4-oxo-2-phenyl-3,4-dihydro-3-quinazolinyl)phenyl]oxyheptyl)oxy]-(11aS))-1,2,3,11a-tetrahydro-5H-pyrrolo[2,1-c][1,4]benzodiazepin-5-one (20f);

7-methoxy-8-[(8-[4-(6-hexahydro-1-pyridinyl-4-oxo-2-phenyl-3,4-dihydro-3-quinazolinyl)phenyl]oxyoctyl)oxy]-(11aS))-1,2,3,11a-tetrahydro-5H-pyrrolo[2,1-c][1,4]benzodiazepin-5-one (20g);

7-methoxy-8-[(9-[4-(6-hexahydro-1-pyridinyl-4-oxo-2-phenyl-3,4-dihydro-3-quinazolinyl)phenyl]oxynonyl)oxy]-(11aS))-1,2,3,11a-tetrahydro-5H-pyrrolo[2,1-c][1,4]benzodiazepin-5-one (20h);

7-methoxy-8-[(10-[4-(6-hexahydro-1-pyridinyl-4-oxo-2-phenyl-3,4-dihydro-3-quinazolinyl)phenyl]oxydecyl)oxy]-(11aS))-1,2,3,11a-tetrahydro-5H-pyrrolo[2,1-c][1,4]benzodiazepin-5-one (20i);

7-methoxy-8-[2-(4-[6-(4-methylhexahydro-1-pyridinyl)-4-oxo-2-phenyl-3,4-dihydro-3-quinazolinyl]phenyloxy)ethyl]oxy-(11aS))-1,2,3,11a-tetrahydro-5H-pyrrolo[2,1-c][1,4]benzodiazepin-5-one (21a);

7-methoxy-8-[3-(4-[6-(4-methylhexahydro-1-pyridinyl)-4-oxo-2-phenyl-3,4-dihydro-3-quinazolinyl]phenyloxy)propyl]oxy-(11aS))-1,2,3,11a-tetrahydro-5H-pyrrolo[2,1-c][1,4]benzodiazepin-5-one (21b);

7-methoxy-8-[4-(4-[6-(4-methylhexahydro-1-pyridinyl)-4-oxo-2-phenyl-3,4-dihydro-3-quinazolinyl]phenyloxy)butyl]oxy-(11aS))-1,2,3,11a-tetrahydro-5H-pyrrolo[2,1-c][1,4]benzodiazepin-5-one (21c);

7-methoxy-8-[5-(4-[6-(4-methylhexahydro-1-pyridinyl)-4-oxo-2-phenyl-3,4-dihydro-3-quinazolinyl]phenyloxy)pentyl]oxy-(11aS))-1,2,3,11a-tetrahydro-5H-pyrrolo[2,1-c][1,4]benzodiazepin-5-one (21d);

7-methoxy-8-[6-(4-[6-(4-methylhexahydro-1-pyridinyl)-4-oxo-2-phenyl-3,4-dihydro-3-quinazolinyl]phenyloxy)hexyl]oxy-(11aS))-1,2,3,11a-tetrahydro-5H-pyrrolo[2,1-c][1,4]benzodiazepin-5-one (21e);

7-methoxy-8-[7-(4-[6-(4-methylhexahydro-1-pyridinyl)-4-oxo-2-phenyl-3,4-dihydro-3-quinazolinyl]phenyloxy)heptyl]oxy-(11aS))-1,2,3,11a-tetrahydro-5H-pyrrolo[2,1-c][1,4]benzodiazepin-5-one (21f);

7-methoxy-8-[8-(4-[6-(4-methylhexahydro-1-pyridinyl)-4-oxo-2-phenyl-3,4-dihydro-3-quinazolinyl]phenyloxy)octyl]oxy-(11aS))-1,2,3,11a-tetrahydro-5H-pyrrolo[2,1-c][1,4]benzodiazepin-5-one (21g);

7-methoxy-8-[9-(4-[6-(4-methylhexahydro-1-pyridinyl)-4-oxo-2-phenyl-3,4-dihydro-3-quinazolinyl]phenyloxy)nonyl]oxy-(11aS))-1,2,3,11a-tetrahydro-5H-pyrrolo[2,1-c][1,4]benzodiazepin-5-one (21h);

7-methoxy-8-[10-(4-[6-(4-methylhexahydro-1-pyridinyl)-4-oxo-2-phenyl-3,4-dihydro-3-quinazolinyl]phenyloxy)decyl]oxy-(11aS))-1,2,3,11a-tetrahydro-5H-pyrrolo[2,1-c][1,4]benzodiazepin-5-one (21i);

7-methoxy-8-[2-(4-[6-(1,4-oxazinan-4-yl)-4-oxo-2-phenyl-3,4-dihydro-3-quinazolinyl]phenyloxy)ethyl]oxy]-(11aS))-1,2,3,11a-tetrahydro-5H-pyrrolo[2,1-c][1,4]benzodiazepin-5-one (22a);

7-methoxy-8-[3-(4-[6-(1,4-oxazinan-4-yl)-4-oxo-2-phenyl-3,4-dihydro-3-quinazolinyl]phenyloxy)propyl]oxy]-(11aS))-1,2,3,11a-tetrahydro-5H-pyrrolo[2,1-c][1,4]benzodiazepin-5-one (22b);

7-methoxy-8-[4-(4-[6-(1,4-oxazinan-4-yl)-4-oxo-2-phenyl-3,4-dihydro-3-quinazolinyl]phenyloxy)butyl]oxy]-(11aS))-1,2,3,11a-tetrahydro-5H-pyrrolo[2,1-c][1,4]benzodiazepin-5-one (22c);

7-methoxy-8-[5-(4-[6-(1,4-oxazinan-4-yl-4-oxo-2-phenyl-3,4-dihydro-3-quinazolinyl]phenyloxy)pentyl]oxy]-(11aS))-1,2,3,11a-tetrahydro-5H-pyrrolo[2,1-c][1,4]benzodiazepin-5-one (22d);

7-methoxy-8-[6-(4-[6-(1,4-oxazinan-4-yl-4-oxo-2-phenyl-3,4-dihydro-3-quinazolinyl]phenyloxy)hexyl]oxy]-(11aS))-1,2,3,11a-tetrahydro-5H-pyrrolo[2,1-c][1,4]benzodiazepin-5-one (22e);

7-methoxy-8-[7-(4-[6-(1,4-oxazinan-4-yl)-4-oxo-2-phenyl-3,4-dihydro-3-quinazolinyl]phenyloxy)heptyl]oxy]-(11aS))-1,2,3,11a-tetrahydro-5H-pyrrolo[2,1-c][1,4]benzodiazepin-5-one (22f);

7-methoxy-8-[8-(4-[6-(1,4-oxazinan-4-yl)-4-oxo-2-phenyl-3,4-dihydro-3-quinazolinyl]phenyloxy)octyl]oxy]-(11aS))-1,2,3,11a-tetrahydro-5H-pyrrolo[2,1-c][1,4]benzodiazepin-5-one (22g);

7-methoxy-8-[9-(4-[6-(1,4-oxazinan-4-yl)-4-oxo-2-phenyl-3,4-dihydro-3-quinazolinyl]phenyloxy)nonyl]oxy]-(11aS))-1,2,3,11a-tetrahydro-5H-pyrrolo[2,1-c][1,4]benzodiazepin-5-one (22h) and 7-methoxy-8-[10-(4-[6-(1,4-oxazinan-4-yl)-4-oxo-2-phenyl-3,4-dihydro-3-quinazolinyl]phenyloxy)decyl]oxy]-(11aS))-1,2,3,11a-tetrahydro-5H-pyrrolo[2,1-c][1,4]benzodiazepin-5-one (22i);

In yet another embodiment the Quinazolinone linked pyrrolo[2,1-c][1,4]benzodiazepine hybrid 5b and 5d exhibits an in vitro anticancer/antitumour activity against human cancer cell lines selected from the group consisting of lung (Hop-62), cervix (SiHa), breast (MCF7, Zr-75-1), colon (Colo205), prostate (DU145, PC3) and oral (DWD, HT1080) cell lines.

In yet another embodiment the concentration of the compound 5d used for in vitro activity against leukemia for GT50 is in the range of 0.06 to 0.19 ○m, at an exposure period of at least 48 hrs.

In yet another embodiment the concentration of the compounds 5b and 5d used for in vitro activity against lung for GI50 is in the range of 0.16 to 1.48 and 0.12 to 0.87 $\mu$m, respectively at an exposure period of at least 48 hrs.

In yet another embodiment the concentration of the compounds 5b and 5d used for in vitro activity against colon for GI50 is in the range of 0.14 $\mu$m and 0.15 to 1.09 $\mu$m, respectively at an exposure period of at least 48 hrs.

In yet another embodiment the concentration of the compounds 5d used for in vitro activity against CNS for GI50 is in the range of 0.16 to 0.38 $\mu$m, at an exposure period of at least 48 hrs.

In yet another embodiment the concentration of the compounds 5d used for in vitro activity against melanoma for GI50 is in the range of 0.15 to 0.42 $\mu$m, at an exposure period of at least 48 hrs.

In yet another embodiment the concentration of the compounds 5b and 5d concentration of the compound used for in vitro activity against ovarian for GI50 is in the range of 0.1 $\mu$m and 0.18 to 0.43 $\mu$m, respectively at an exposure period of at least 48 hrs.

In yet another embodiment the concentration of the compounds 5d used for in vitro activity against renal for GI50 is in the range of 0.16 to 0.36 $\mu$m, at an exposure period of at least 48 hrs.

In yet another embodiment the concentration of the compounds 5b and 5d used for in vitro activity against prostate for GI50 is in the range of 0.13 $\mu$m and 0.26 to 0.29 $\mu$m, respectively at an exposure period of at least 48 hrs.

In yet another embodiment the concentration of the compounds 5b and 5d used for in vitro activity against breast for IC50 is in the range of 0.16 to 1.83 $\mu$m, and 0.11 to 1.73 $\mu$m, respectively at an exposure period of at least 48 hrs.

The present invention further provides a process for the preparation of quinazolinone linked pyrrolo[2,1-c][1,4]benzodiazepine hybrids of formulae A Formuala A

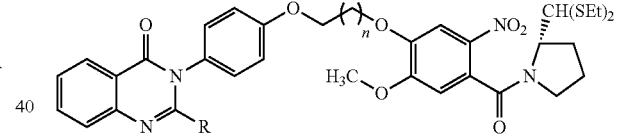

n = 1-9 wherein G = or or

R = Methyl, styryl, phenyl;
R₁ = H, halo, pyrrolidine, piperidine, 4-methyl piperidine or morpholine;
X, Y, Z = H, halo, alkyl or alkoxy and the said process comprising the steps of:

a) Reacting (2S)—N-[(n-bromoalkyloxy)-5-methoxy-2-nitrobenzol)]pyrrolidine-2-carboxaldehyde diethylthioacetal of formula with quinazolinones of formulae 2, 6 and 14, isolating the nitro compounds of formulae 3a-r, 7a-i and 15a-I,

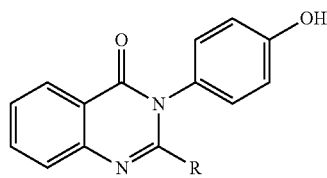

2

R = methyl, styryl

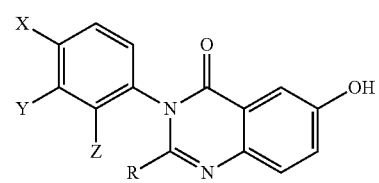

6

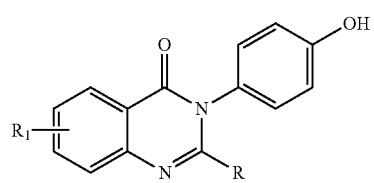

14

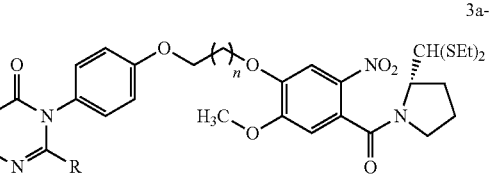

3a-r 7a-i 15a-i wherein n = 1-9 b) reducing the above nitro compounds of formulae 3a-r, 7a-i and 15a-i with SnCl₂.2H₂O in presence of organic solvent like methanol or ethanol up to a reflux temperature, isolating the amino compounds of formulae 4a-r, 8a-i and 16a-I,

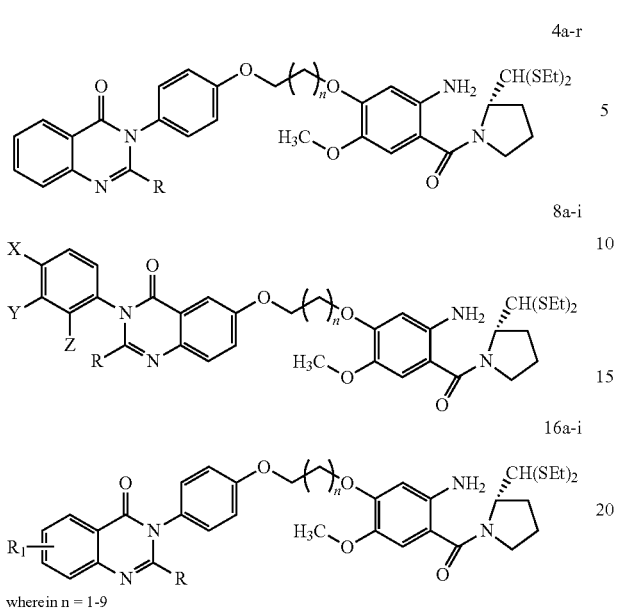

4a-r 8a-i 16a-i wherein n = 1-9 c) reacting the above amino compounds of formulae 4a-r, 8a-i and 16a-i with known deprotecting agents in a conventional manner to give novel pyrrolo[2,1-c][1,4]benzodiazepine hybrids of formulae 5a-r, 9a-i to 13a-i and 17a-i to 22a-i.

The present invention further provides a process for preparation of quinazolinone linked pyrrolo[2,1-c][1,4]benzodiazepine hybrids of formulae 5a-r, 9a-i to 13a-i and 17a-i to 22a-i which comprises a) reacting (2S)—N-[(n-bromoalkyloxy)-5-methoxy-2-nitrobenzoyl)]pyrrolidine-2-carboxaldehyde diethylthioacetal of formula 1a-i

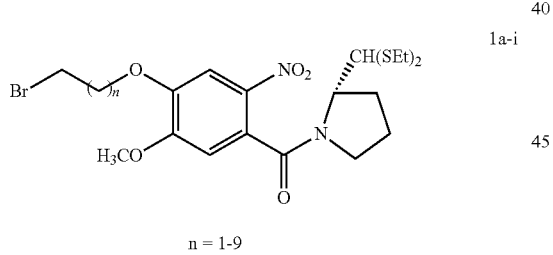

1a-i n = 1-9 wherein
n=1 for 1a ((2S)—N-[4-(2-bromoethoxy)-5-methoxy-2-nitro-benzoyl]pyrrolidine-2-carboxaldehyde diethylthioacetal)
n=2 for 1b ((2S)—N-[4-(3-bromopropoxy)-5-methoxy-2-nitro-benzoyl]pyrrolidine-2-carboxaldehyde diethylthioacetal)
n=3 for 1c ((2S)—N-[4-(4-bromobutoxy)-5-methoxy-2-nitro-benzoyl]pyrrolidine-2-carboxaldehyde diethylthioacetal)
n=4 for 1d ((2S)—N-[4-(5-bromopentyloxy)-5-methoxy-2-nitro-benzoyl]pyrrolidine-2-carboxaldehyde diethylthioacetal)
n=5 for 1e ((2S)—N-[4-(6-bromohexyloxy)-5-methoxy-2-nitro-benzoyl]pyrrolidine-2-carboxaldehyde diethylthioacetal)
n=6 for 1f ((2S)—N-[4-(7-bromoheptyloxy)-5-methoxy-2-nitro-benzoyl]pyrrolidine-2-carboxaldehyde diethylthioacetal)
n=7 for 1g ((2S)—N-[4-(8-bromooctyloxy)-5-methoxy-2-nitro-benzoyl]pyrrolidine-2-carboxaldehyde diethylthioacetal)
n=8 for 1 h ((2S)—N-[4-(9-bromononyloxy)-5-methoxy-2-nitro-benzoyl]pyrrolidine-2-carboxaldehyde diethylthioacetal)
n=9 for 1i ((2S)—N-[4-(10-bromodecyloxy)-5-methoxy-2-nitro-benzoyl]pyrrolidine-2-carboxaldehyde diethylthioacetal)
with the compounds of formulae 2, 6 and 14

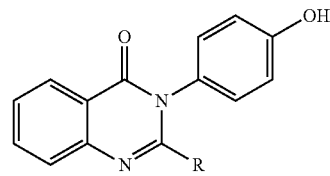

2

R = alkyl, aryl

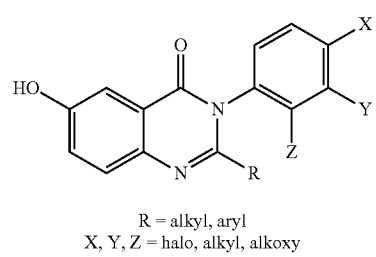

6

R = alkyl, aryl
X, Y, Z = halo, alkyl, alkoxy

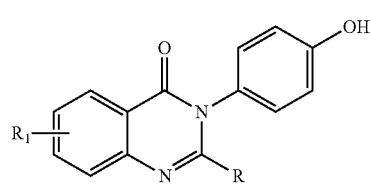

14

R = alkyl, aryl
$R_1$ = Halo, pyrrolidine, piperidine
4-methyl piperidin, morpholin in an aprotic water miscible organic solvent, in the presence of anhydrous mild inorganic base, under refluxing temperature in an oil bath, for a period of about 48 hrs, followed by the removal of inorganic base by filtration and evaporating the organic solvent to obtain the resultant crude product and purifying it by column chromatography to obtain the desired product of formulae 3a-r, 7a-i and 15a-i.

b) Reducing the compounds of formulae 3a-r, 7a-i and 15a-i with $SnCl_2.2H_2O$, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired products of formulae 4a-r, 8a-i and 16a-i.

c) Reacting the above said amino compounds of formulae 4a-r, 8a-i and 16a-i obtained in step (b) with a deprotecting agent by known method to obtain the desired compounds of formulae 5a-r, 9a-i to 13a-i and 17a-i to 22a-i.

DETAILED DESCRIPTION OF THE INVENTION

The precursors quinazolinones of formulae 2, 6 and 14 have been prepared literature method (K. Miyata, Y. Kurogi, Y. Sakai, Y. Tsuda, U.S. Pat. No. 5,922,866; Chem. Abstr. 126 (1999) 251165. D. Raffia, G. Daidone, B. Maggio, S. Cascioferro, F. Plescia, D. Schillaci, II Farmaco 59 (2004) 215-221) and (2S)-2-[di(ethylsulfanyl)methyl]tetrahydro-1H-1-pyrrolyl(4-hydroxy-5-methoxy-2-nitrophenyl)methanone of formula 1 (Thurston, D. E.; Murthy, V. S.; Langley, D. R.; Jones, G. B. *Synthesis*. 1990, 81) has been prepared by literature method.

Some representative compounds of formulae 5a-r, 9a-i to 13a-i and 17a-i to 22a-i for the present inventions are given below 7-methoxy-8{-2-[4-(2-methyl-4-oxo-3,4-dihydro-3-quinazolinyl)phenoxy]ethoxy}-(11aS)-1,2,3,11a-tetrahydro-5H-pyrrolo[2,1-c][1,4]benzodiazepine-5-one (5a);

7-methoxy-8{-3-[4-(2-methyl-4-oxo-3,4-dihydro-3-quinazolinyl)phenoxy]propoxy}-(11aS)-1,2,3,11a-tetrahydro-5H-pyrrolo[2,1-c][1,4]benzodiazepine-5-one (5b);

7-methoxy-8{-4-[4-(2-methyl-4-oxo-3,4-dihydro-3-quinazolinyl)phenoxy]butoxy-}-(11aS)-1,2,3,11a-tetrahydro-5H-pyrrolo[2,1-c][1,4]-benzodiazepine-5-one (5c);

7-methoxy-8-{5-[4-(2-methyl-4-oxo-3,4-dihydro-3-quinazolinyl)phenoxy]pentyloxy-}-(11aS)-1,2,3,11a-tetrahydro-5H-pyrrolo[2,1-c][1,4]benzodiazepine-5-one (5d);

7-methoxy-8-{3-[(4-4-oxo-2-[(E)-2-phenyl-1-ethenyl]-3,4-dihydro-3-quinazolinylphenyl)oxy]propoxy}-(11aS)-1,2,3,11a-tetrahydro-5H-pyrrolo[2,1-c][1,4]benzodiazepine-5-one (5k);

7-methoxy-8-{4-[(4-4-oxo-2-[(E)-2-phenyl-1-ethenyl]-3,4-dihydro-3-quinazolinylphenyl)oxy]butoxy}-(11aS)-1,2,3,11a-tetrahydro-5H-pyrrolo [2,1-c][1,4]benzodiazepine-5-one (5l);

7-methoxy-8-{5-[(4-4-oxo-2-[(E)-2-phenyl-1-ethenyl]-3,4-dihydro-3-quinazolinylphenyl)oxy]pentyloxy}-(11aS)-1,2,3,11a-tetrahydro-5H-pyrrolo[2,1-c][1,4]benzodiazepine-5-one (5m);

7-methoxy-8-{5-[3-(4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (9d);

7-methoxy-8-{5-[3-(3-chloro-4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (10d);

7-methoxy-8-{(5-[3-(4-methoxyphenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (11d);

7-methoxy-8-{4-[3-(4-iodo-2-methylphenyl)-2-methyl-4-oxo-34-dihydro-6-quinazolinyl]oxybutoxy}-(11aS)-1,2,3,11a-tetrahydro-5H-pyrrolo[2,1-c][1,4]benzodiazepine-5-one (12c);

7-methoxy-8-{5-[3-(4-iodo-2-methylphenyl)-2-methyl-4-oxo-34-dihydro-6-quinazolinyl]oxypentyloxy}-(11aS)-1,2,3,11a-tetrahydro-5H-pyrrolo[2,1-c][1,4]benzodiazepine-5-one (12d);

7-methoxy-8-{5-[3-(2,4-dichlorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (13d);

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1, which comprise:

1. The ether linkage at C-8 position of DC-81 intermediates with the compounds of formulae 2, 6 and 14.
2. Refluxing the reaction mixtures for 48 h.
3. Synthesis of C-8 linked PBD antitumour antibiotic hybrid imines.
4. Purification by column chromatography using different solvents like ethyl acetate, hexane, dichloromethane and methanol.

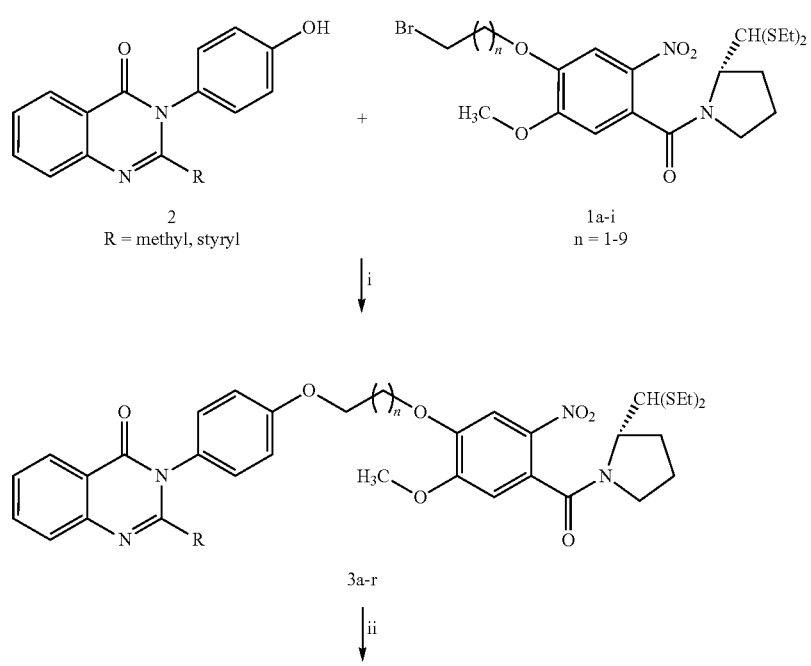

Scheme-1

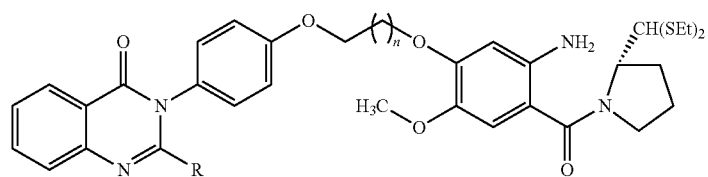
4a-r
↓ iii
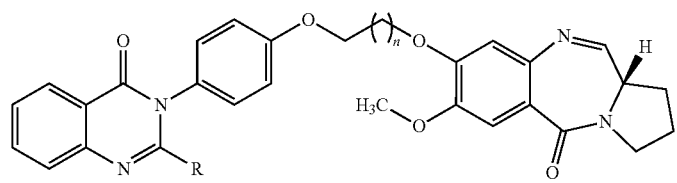
5a-r
n = 1-9
R = Methyl, styryl
Reagents and conditions:
(i) K₂CO₃, acetone, 18 h, reflux, 90-92%;
(ii) SnCl₂·2H₂O, MeOH, 2 h, reflux, 85-87%;
(iii) HgCl₂—CaCO₃, CH₃CN—H₂O (4:1), 12 h, rt, 68-71%.
Scheme 2
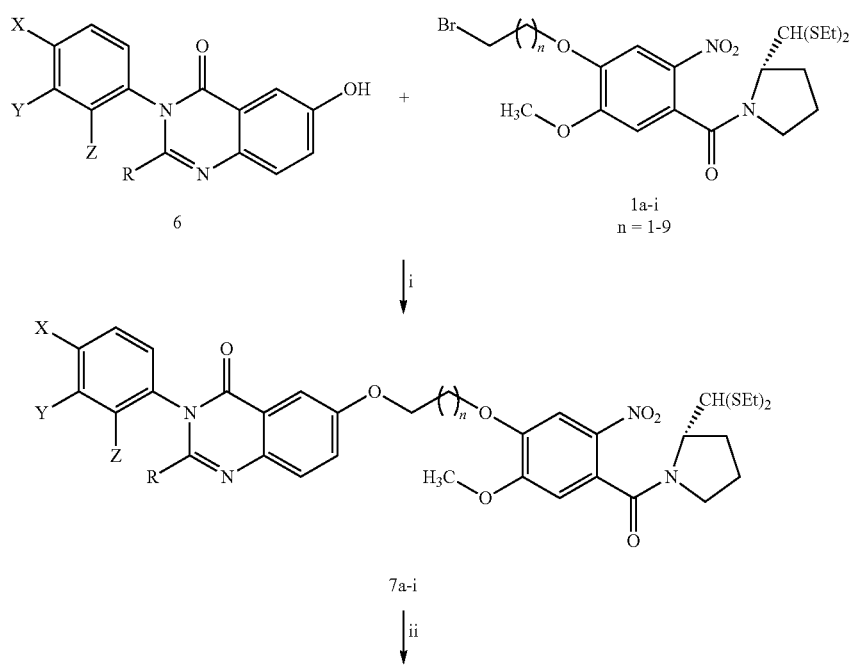

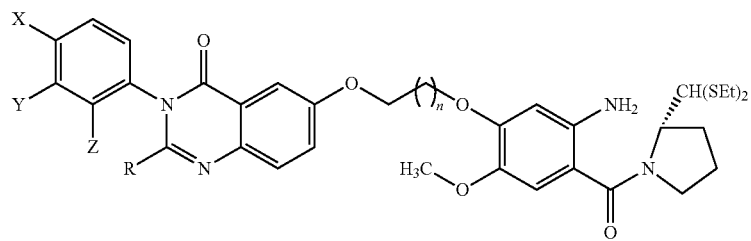
8a-i
↓ iii
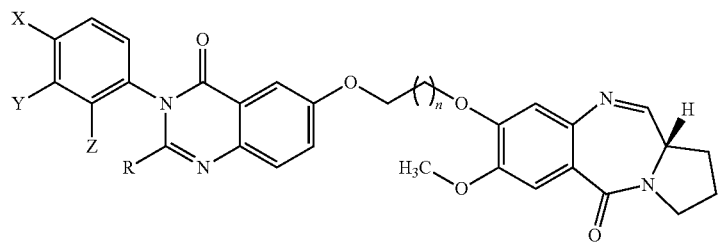
n = 1-9
9a-i to 13a-i
X = F, Y, Z = H; For 9a-i
X = F, Y = Cl, Z = H; For 10a-i
X = OMe, Y, Z = H; For 11a-i
X = I, Y = H, Z = CH₃; For 12a-i
X, Y = Cl, Z = H; For 13a-i
Reagents and conditions:
(i) K₂CO₃, acetone, 18 h, refllux, 90-92%;
(ii) SnCl₂·2H₂O, MeOH, 2 h, reflux, 85-87%;
(iii) HgCl₂—CaCO₃, CH₃CN—H₂O (4:1), 12 h, rt, 68-71%.
Scheme 3
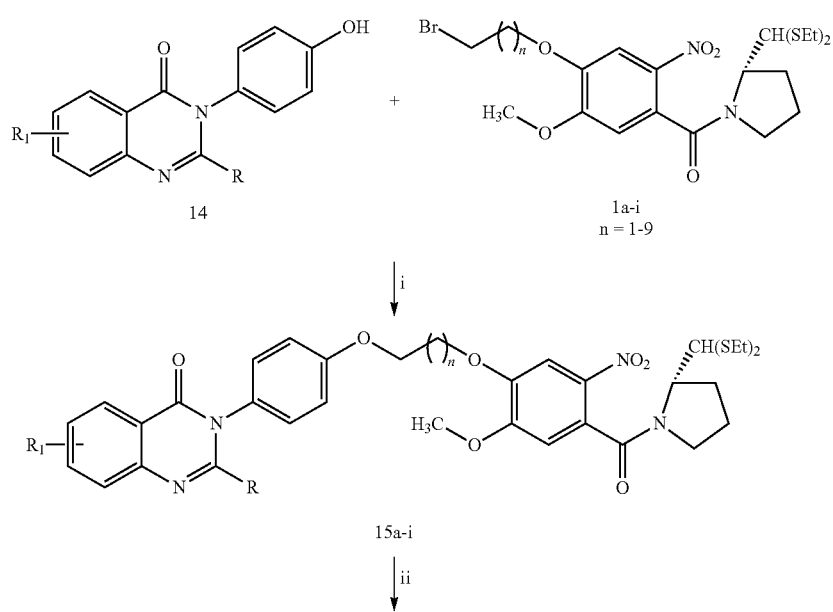
14  +  1a-i
       n = 1-9
↓ i
15a-i
↓ ii

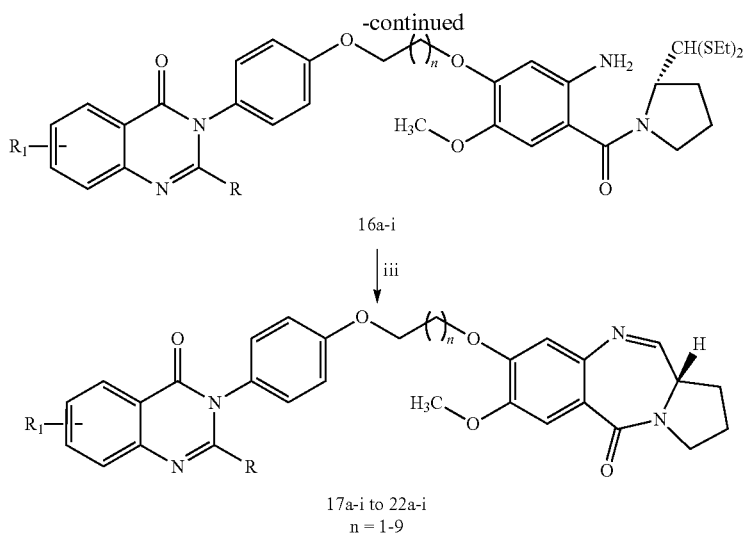

16a-i

↓ iii 17a-i to 22a-i
n = 1-9

R = Phenyl
$R_1$ = Hydrogen for 17a-i
$R_1$ = Chloro for 18a-i
$R_1$ = Pyrrolidin for 19a-i
$R_1$ = Piperidin for 20a-i
$R_1$ = 4-methyl piperidin for 21a-i
$R_1$ = Morpholin for 22a-i The following examples are given by way of illustration and therefore should not be construed to the present limit of the scope of invention.

Example-1

7-methoxy-8{-3-[4-(2-methyl-4-oxo-3,4-dihydro-3-quinazolinyl)phenoxy]propoxy}-(11aS)-1,2,3,11a-tetrahydro-5H-pyrrolo[2,1-c][1,4]benzodiazepine-5-one (5b)

To a solution of 2S—N-[4-(3-bromopropoxy)-5-methoxy-2-nitrobenzoyl]pyrrolidine-2-carboxaldehyde diethylthioacetal (1b) (521 mg, 1.0 mmol) in dry acetone (20 mL) was added anhydrous potassium carbonate (690 mg, 5.0 mmol) and 3-(4-Hydroxy-phenyl)-2-methyl-3H-quinazolinone (2) (252 mg, 1.0 mmol). The reaction mixture was refluxed in an oil bath for 24 h and the reaction was monitored by TLC using ethyl acetate-hexane (6:4) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product (3b) (553 mg, 80% yield).

$^1$H NMR (CDCl$_3$): δ 1.30-1.46 (m, 6H), 1.72-1.79 (m, 2H), 1.89-2.02 (m, 4H), 2.04-2.16 (m, 2H), 2.24 (s, 3H), 2.66-2.86 (m, 4H), 3.19-3.29 (m, 2H), 3.94 (s, 3H), 4.06 (t, 2H, J=6.23 Hz), 4.13 (t, 2H, J=6.52 Hz), 4.63-4.70 (m, 1H), 4.83 (d, 1H, J=3.966 Hz), 6.78 (s, 1H), 7.00 (d, 2H, J=8.876 Hz), 7.14 (d, 2H, J=8.876 Hz), 7.40-7.46 (m, 1H), 7.62 (d, 1H J=8.68 Hz), 7.64 (s, 1H), 7.69-7.76 (m, 1H), 8.21-8.24 (dd, 1H, J=7.932 Hz): FABMS: 693.91 (M+H)$^+$.

To a compound of 3b (692.85 mg, 1.0 mmol) in methanol (10 mL), SnCl$_9$.2H$_2$O (1.12 g, 5.0 mmol) was added and refluxed until the TLC indicated the completion of the reaction. The methanol was then evaporated in vacuum and the aqueous layer was then adjusted to pH 8 with 10% NaHCO$_3$ solution and extracted with ethyl acetatate (60 mL). The combined organic phase was dried over Na$_2$SO$_4$ and evaporated under vacuum to afford the crude amino diethylthioacetal 4b (642 mg, 97% yield), which was directly used in the next step.

A solution of 4b (662.26 mg, 1.0 mmol), HgCl$_2$ (576 mg, 2.26 mmol) and CaCO$_3$ (225 mg, 2.46 mmol) in acetonitrile-water (4:1) was stirred slowly at room temperature overnight until complete consumption of starting material as indicated by the TLC. The clear organic supernatant liquid was extracted with ethyl acetate and washed with saturated 5% NaHCO$_3$ (20 mL), brine (20 mL) and the combined organic phase was dried over Na$_2$SO$_4$. The organic layer was evaporated in vacuum to afford a white solid, which was first eluted on a column chromatography with ethyl acetate to remove mercuric salts, and then with ethyl acetate to obtain the pure product 5b (312 mg, 58% yield).

$^1$H NMR (CDCl$_3$): δ 1.84-2.09 (m, 6H), 2.26 (s, 3H), 3.70-3.87 (m, 3H), 3.95 (s, 3H), 4.01-4.10 (m, 4H), 6.82 (s, 1H), 7.03 (d, 2H, J=8.876 Hz), 7.15 (d, 2H, J=8.876 Hz), 7.44-7.49 (m, 1H), 7.52 (s, 1H), 7.67 (d, 2H, J=6.339 Hz), 7.74-7.79 (m, 1H), 8.27 (d, 1H, J=8.531 Hz): FABMS: 539 (M+H)$^+$.

Example-2

7-methoxy-8{-4-[4-(2-methyl-4-oxo-3,4-dihydro-3-quinazolinyl)phenoxy]butoxy}-(11aS)-1,2,3,11a-tetrahydro-5H-pyrrolo[2,1-c][1,4]benzodiazepine-5-one (5c)

This compound was prepared according to the method described for the compound 3b by employing 2S—N-[4-(4-bromobutoxy)-5-methoxy-2-nitrobenzoyl]pyrrolidine-2-carboxaldehyde diethylthioacetal (1c) (535 mg, 1.0 mmol) was added anhydrous potassium carbonate (690 mg, 5.0 mmol) and to obtain the pure product 3-(4-Hydroxy-phenyl)-2-methyl-3H-quinazolinone (2) (252 mg, 1.0 mmol). 3c (593 mg, 84% yield).

$^1$H NMR (CDCl$_3$): δ 1.30-1.46 (m, 10H), 1.89-2.02 (m, 4H), 2.04-2.16 (m, 2H), 2.24 (s, 3H), 2.66-2.86 (m, 4H), 3.19-3.29 (m, 2H), 3.94 (s, 3H), 4.06 (t, 2H, J=6.23 Hz), 4.13 (t, 2H, J=6.52 Hz), 4.63-4.70 (m, 1H), 4.83 (d, 1H, J=3.966 Hz), 6.78 (s, 1H), 7.00 (d, 2H, J=8.876. Hz), 7.14 (d, 2H, J=8.876 Hz), 7.40-7.46 (m, 1H), 7.62 (d, 1H J=8.68 Hz), 7.64 (s, 1H), 7.69-7.76 (m, 1H), 8.21-8.24 (dd, 1H, J=7.932 Hz): FABMS: 707.91 (M+H)$^+$.

This compound was prepared according to the method described for the compound 4b by reducing 3c (706.87 mg, 1.0 mmol) using SnCl$_2$.2H$_2$O (1.12 g, 5.0 mmol). The amino compound 4c obtained was (655 mg, 97% yield).

This compound was prepared according to the method described for the compound 5b employing 4c (676.89 mg, 1.0 mmol) and HgCl$_2$ (582 mg, 2.26 mmol), CaCO$_3$ (230 mg, 2.46 mmol) in acetonitrile-water (4:1) to obtain the pure product 5c (320 mg, 58% yield).).

$^1$H NMR (CDCl$_3$): Ω1.57-1.75 (m, 4H), 1.85-2.10 (m, 4H), 2.26 (s, 3H), 3.70-3.87 (m, 3H), 3.95 (s, 3H), 4.01-4.10 (m, 4H), 6.82 (s, 1H), 7.03 (d, 2H, J=8.876 Hz), 7.15 (d, 2H, J=8.876 Hz), 7.44-7.49 (m, 1H), 7.52 (s, 1H), 7.67 (d, 2H, J=6.339 Hz), 7.74-7.79 (m, 1H), 8.27 (d, 1H, J=8.531 Hz): FARMS: 553 (W+H)$^+$.

Example-3

7-methoxy-8{-5-[4-(2-methyl-4-oxo-3,4-dihydro-3-quinazolinyl)phenoxy]pentyloxy}-(11aS)-1,2,3,11a-tetrahydro-5H-pyrrolo[2,1-c][1,4]benzodiazepine-5-one (5d)

This compound was prepared according to the method described for the compound 3b by employing 2S—N-[4-(5-bromopentyloxy)-5-methoxy-2-nitrobenzoyl]pyrrolidine-2-carboxaldehyde diethylthioacetal (1d) (549 mg, 1.0 mmol) was added anhydrous potassium carbonate (690 mg, 5.0 mmol) and 3-(4-Hydroxy-phenyl)-2-methyl-3H-quinazolinone (2) (252 mg, 1.0 mmol) to obtain the pure product 3d (626 mg, 87% yield).

$^1$H NMR (CDCl$_3$): δ 1.30-1.46 (m, 10H), 1.70-1.81 (m, 2H), 1.89-2.02 (m, 4H), 2.04-2.16 (m, 2H), 2.24 (s, 3H), 2.66-2.86 (m, 4H), 3.19-3.29 (m, 2H), 3.94 (s, 3H), 4.06 (t, 2H, J=6.23 Hz), 4.13 (t, 2H, J=6.52 Hz), 4.63-4.70 (m, 1H), 4.83 (d, 1H, J=3.966 Hz), 6.78 (s, 1H), 7.00 (d, 2H, J=8.876 Hz), 7.14 (d, 2H, J=8.876 Hz), 7.40-7.46 (m, 1H), 7.62 (d, 1H J=8.68 Hz), 7.64 (s, 1H), 7.69-7.76 (m, 1H), 8.21-8.24 (dd, 1H, J=7.932 Hz): FABMS: 721.91 (M+H)$^+$.

This compound was prepared according to the method described for the compound 4b by reducing a solution of 3d (720.90 mg, 1.0 mmol) using SnCl$_2$.2H$_2$O (1.12 g, 5.0 mmol). The amino compound 4d obtained was (669 mg, 97% yield).

This compound was prepared according to the method described for the compound 5b employing 4d (690.92 mg; 1.0 mmol) and HgCl$_2$ (590 mg, 2.26 mmol), CaCO$_3$ (244 mg, 2.46 mmol) in acetonitrile-water (4:1) to obtain the pure product 5d (328 mg, 58% yield).

$^1$H NMR (CDCl$_3$): δ 1.57-1.75 (m, 4H), 1.86-2.11 (m, 6H), 2.26 (s, 3H), 3.70-3.87 (m, 3H), 3.95 (s, 3H), 4.01-4.10 (m, 4H), 6.82 (s, 1H), 7.03 (d, 2H, J=8.876 Hz), 7.15 (d, 2H, J=8.876 Hz), 7.44-7.49 (m, 1H), 7.52 (s, 1H), 7.67 (d, 2H, J=6.339 Hz), 7.74-7.79 (m, 1H), 8.27 (d, 1H, J=8.531 Hz): FABMS: 567 (M+H)$^+$.

Example-4

7-methoxy-8-{3-[(4-4-oxo-2-[(E)-2-phenyl-1-ethenyl]-3,4-dihydro-3-quinazolinyl phenyl)oxy]propoxy}-(11aS)-1,2,3,11a-tetrahydro-5H-pyrrolo[2,1-c][1,4]benzodiazepine-5-one (5k)

This compound was prepared according to the method described for the compound 3b by employing 2S—N-[4-(3-bromopropoxy)-5-methoxy-2-nitrobenzoyl]pyrrolidine-2-carboxaldehyde diethylthioacetal (1b) (521 mg, 1.0 mmol) was added anhydrous potassium carbonate (690 mg, 5.0 mmol) and 3-(4-hydroxyphenyl)-2-[(E)-2-phenyl-1-ethenyl]-3,4-dihydro-4-quinazolinone (340.37 mg, 1.0 mmol). to obtain the pure product 3k (655 mg, 84% yield).

$^1$H NMR (CDCl$_3$): δ 1.30-1.46 (m, 6H), 1.72-1.79 (m, 2H), 1.8.9-2.02 (m, 4H) 2.04-2.16 (m, 2H), 2.66-2.86 (m, 4H), 3.19-3.29 (m, 2H), 3.94 (s, 3H), 4.06-4.18 (m, 4H) 4.63-4.71 (m, 1H), 4.81-4.84 (m, 1H), 6.41-6.46 (d, 1H, J=15.108 Hz), 6.78 (s, 1H), 7.05 (d, 2H, J=9.065 Hz), 7.20 (d, 2H, J=8.309 Hz), 7.26-7.37 (m, 5H) 7.64 (s, 1H), 7.72-7.76 (m, 2H), 7.93-7.98 (d, 1H, J=15.108 Hz), 8.26 (d, 1H, J=7.554 Hz): FABMS: 781.91 (M+H)$^+$.

This compound was prepared according to the method described for the compound 4b by reducing 3k (780.87 mg, 1.0 mmol) using SnCl$_2$.2H$_2$O (1.12 g, 5.0 mmol). The amino compound 4k obtained was (727 mg, 97% yield).

This compound was prepared according to the method described for the compound 5b employing 4k (750 mg, 1.0 mmol) and HgCl$_2$ (582 mg, 2.26 mmol), CaCO$_3$ (230 mg, 2.46 mmol) in acetonitrile-water (4:1) to obtain the pure product 5k (372 mg, 58% yield).).

$^1$H NMR (CDCl$_3$): δ 1.87-2.14 (m, 6H), 3.70-3.87 (m, 3H), 3.96 (s, 3H), 4.04-4.20 (m, 4H), 6.45-6.52 (d, 1H, J=15.361 Hz) 6.84 (s, 1H), 7.28-7.44 (m, 10H) 7.23 (d, 2H, J=8.046 Hz), 7.53 (s, 1H), 7.68 (d, 1H, J=5.120 H), 7.80 (d, 2H, J=3.657 Hz), 7.94-8.02 (d, 1H, J=15.361 Hz) 8.31 (d, 1H, J=8.046 Hz): FABMS: 627 (M+H)$^+$.

Example-5

7-methoxy-8-{4-[(4-4-oxo-2-[(E)-2-phenyl-1-ethenyl]-3,4-dihydro-3-quinazolinylphenyl)oxy]butoxy}-(11aS)-1,2,3,11a-tetrahydro-5H-pyrrolo[2,1-c][1,4]benzodiazepine-5-one (5l)

This compound was prepared according to the method described for the compound 3b by employing 2S—N-[4-(4-bromobutoxy)-5-methoxy-2-nitrobenzoyl]pyrrolidine-2-carboxaldehyde diethylthioacetal (1c) (535 mg, 1.0 mmol) was added anhydrous potassium carbonate (690 mg, 5.0 mmol) and 3-(4-hydroxyphenyl)-2-[(E)-2-phenyl-1-ethenyl]-3,4-dihydro-4-quinazolinone (340.37 mg, 1.0 mmol). to obtain the pure product 3l (666.9 mg, 84% yield).

$^1$H NMR (CDCl$_3$): δ 1.30-1.46 (m, 10H), 1.89-2.02 (m, 4H), 2.04-2.16 (m, 2H), 2.66-2.86 (m, 4H), 3.19-3.29 (m, 2H), 3.94 (s, 3H), 4.06-4.18 (m, 4H) 4.63-4.71 (m, 1H); 4.81-4.84 (m, 1H, 6.41-6.46 (d, 1H, J=15.108 Hz), 6.78 (s, 1H), 7.05 (d, 2H, J=9.065 Hz), 7.20 (d, 2H, J=8.309 Hz), 7.26-7.37 (m, 5H) 7.64 (s, 1H), 7.72-7.76 (m, 2H), 7.93-7.98 (d, 1H, J=15.108 Hz), 8.26 (d, 1H, J=7.554 Hz): FABMS: 795.91 (M+H)$^+$.

This compound was prepared according to the method described for the compound 4b by reducing 3l (794.87 mg, 1.0 mmol) using SnCl$_2$.2H$_2$O (1.12 g, 5.0 mmol). The amino compound 4l obtained was (741 mg, 97% yield).

This compound was prepared according to the method described for the compound 5b employing 4l (764.89 mg, 1.0 mmol) and HgCl$_2$ (582 mg, 2.26 mmol), CaCO$_3$ (230 mg, 2.46 mmol) in acetonitrile-water (4:1) to obtain the pure product 5l (380 mg, 58% yield).).

$^1$H NMR (CDCl$_3$): δ 1.57-1.75 (m, 4H), 1.85-2.10 (m, 4H), 3.70-3.87 (m, 3H), 3.95 (s, 3H), 4.04-4.20 (m, 4H), 6.45-6.52 (d, 1H, J=15.361 Hz) 6.84 (s, 1H), 7.28-7.44 (m, 10H) 7.23 (d, 2H, J=8.046 Hz), 7.53 (s, 1H), 7.68 (d, 1H, J=5.120 H), 7.80 (d, 2H, J=3.657 Hz), 7.94-8.02 (d, 1H, J=15.361 Hz) 8.31 (d, 1H, J=8.046 Hz): FABMS: 641 (M+H)$^+$.

Example-6

7-methoxy-8-{5-[(4-4-oxo-2-[(E)-2-phenyl-1-ethenyl]-3,4-dihydro-3-quinazolinylphenyl)pentyloxyl}-(11aS)-1,2,3,11a-tetrahydro-5H-pyrrolo[2,1-c][1,4]benzodiazepine-5-one (5m)

This compound was prepared according to the method described for the compound 3b by employing 2S—N-[4-(5-bromopentyloxy)-5-methoxy-2-nitrobenzoyl]pyrrolidine-2-carboxaldehyde diethylthioacetal (1d) (549 mg, 1.0 mmol) was added anhydrous potassium carbonate (690 mg, 5.0 mmol), and 3-(4-hydroxyphenyl)-2-[(E)-2-phenyl-1-ethenyl]-3,4-dihydro-4-quinazolinone (340.37 mg, 1.0 mmol). to obtain the pure product 3m (654 mg, 84% yield).

$^1$H NMR (CDCl$_3$): δ 1.30-1.46 (m, 10H), 1.70-1.81 (m, 2H), 1.89-2.02 (m, 4H), 2.04-2.16 (m, 2H), 2.66-2.86 (m, 4H), 3.19-3.29 (m, 2H), 3.94 (s, 3H), 4.06-4.18 (m, 4H) 4.63-4.71 (m, 1H), 4.81-4.84 (m, 1H), 6.41-6.46 (d, 1H, J=15.108 Hz), 6.78 (s, 1H), 7.05 (d, 2H, J=9.065 Hz), 7.20 (d, 2H, J=8.309 Hz), 7.26-7.37 (m, 5H) 7.64 (s, 1H), 7.72-7.76 (m, 2H), 7.93-7.98 (d, 1H, J=15.108 Hz), 8.26 (d, 1H, J=7.554 Hz): FABMS: 809.91 (M+H)$^+$.

This compound was prepared according to the method described for the compound 4b by reducing 3m (808.87 mg, 1.0 mmol) using SnCl$_2$.2H$_2$O (1.12 g, 5.0 mmol). The amino compound 4m obtained was (755 mg, 97% yield).

This compound was prepared according to the method described for the compound 5b employing 4m (778.89 mg, 1.0 mmol) and HgCl$_2$ (582 mg, 2.26 mmol), CaCO$_3$ (230 mg, 2.46 mmol) in acetonitrile-water (4:1) to obtain the pure product 5m (390 mg, 58% yield).).

$^1$H NMR (CDCl$_3$): δ 1.61-1.82 (m, 4H), 1.87-2.14 (m, 6H), 3.70-3.87 (m, 3H), 3.96 (s, 3H) 4.04-4.20 (m, 4H), 6.45-6.52 (d, 1H, J=15.361 Hz) 6.84 (s, 1H), 7.28-7.44 (m, 10H) 7.23 (d, 2H, J=8.046 Hz), 7.53 (s, 1H), 7.68 (d, 1H, J=5.120 H), 7.80 (d, 2H, J=3.657 Hz), 7.94-8.02 (d, 1H, J=15.361 Hz) 8.31 (d, 1H, J=8.046 Hz): FABMS: 655 (M+H)$^+$.

Example-7

7-methoxy-8-{3-[3-(3-chloro-4-fluorophenyl)-2-methyl-4-oxo-3,4-dihydro-6-quinazolinyl]oxypropylloxy}-(11aS)-1,2,3,11a-tetrahydro-5H-pyrrolo[2,1-c][1,4]benzodiazepine-5-one (10b)

This compound was prepared according to the method described for the compound. 3b by employing 2S—N-[4-(3-bromopropoxy)-5-methoxy-2-nitrobenzoyl]pyrrolidine-2-carboxaldehyde diethylthioacetal (1b) (521 mg, 1.0 mmol) was added anhydrous potassium carbonate (690 mg, 5.0 mmol) and 3-(3-chloro-4-fluorophenyl)-6-hydroxy-2-methyl-3,4-dihydro-4-quinazolinone (304 mg, 1.0 mmol). to obtain the pure nitro product (625 mg, 84% yield).

$^1$H NMR (CDCl$_3$): δ 1.30-1.46 (m, 6H), 1.72-1.79 (m, 2H), 1.89-2.02 (m, 4H), 2.04-2.16 (m, 2H), 2.25 (s, 3H), 2.67-2.92 (m, 4H), 3.18-3.36 (m, 2H), 3.97 (s, 3H), 4.07-4.20 (m, 4H), 4.67-4.77 (m, 1H), 4.86-4.91 (m, 1H), 6.82 (s, 1H), 7.32-7.43 (m, 3H), 7.56-7.71 (m, 4H): FABMS: 745 (M+H)$^+$.

This compound was prepared according to the method described for the compound 4b by reducing nitro compound (744 mg, 1.0 mmol) using SnCl$_2$.2H$_2$O (1.12 g, 5.0 mmol). The amino compound obtained was (603 mg, 97% yield).

This compound was prepared according to the method described for the compound 5b employing amine (714 mg, 1.0 mmol) and HgCl$_2$ (582 mg, 2.26 mmol), CaCO$_3$ (230 mg, 2.46 mmol) in acetonitrile-water (4:1) to obtain the pure product 10b (346 mg, 58% yield).

$^1$H NMR (CDCl$_3$): δ 1.84-2.09 (m, 6H), 2.25 (s, 3H), 3.48-3.88 (m, 3H), 3.94 (s, 3H), 4.02-4.16 (m, 4H), 6.81 (s, 1H), 7.13-7.23 (m, 1H), 7.30-7.41 (m, 3H), 7.51 (s, 1H), 7.58 (d, 2H, j=2.493 Hz), 7.63 (s, 1H), 7.67 (d, 1H, J=4.985 Hz): FABMS: 591 (M+H)$^+$.

Example-8

7-methoxy-8-{4-[3-(3-chloro-4-fluorophenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (10c)

This compound was prepared according to the method described for the compound 3b by employing 2S—N-[4-(4-bromobutoxy)-5-methoxy-2-nitrobenzoyl]pyrrolidine-2-carboxaldehyde diethylthioacetal (1c) (535 mg, 1.0 mmol) was added anhydrous potassium carbonate (690 mg, 5.0 mmol) and 3-(3-chloro-4-fluorophenyl)-6-hydroxy-2-methyl-3,4-dihydro-4-quinazolinone (304 mg, 1.0 mmol). to obtain the pure nitro product (636 mg, 84% yield).

$^1$H NMR (CDCl$_3$): δ 1.30-1.46 (m, 10H), 1.89-2.02 (m, 4H), 2.04-2.16 (m, 2H), 2.25 (s, 3H), 2.67-2.92 (m, 4H), 3.18-3.36 (m, 2H), 3.97 (s, 3H), 4.07-4.20 (m, 4H), 4.67-4.77 (m, 1H), 4.86-4.91 (m, 1H), 6.82 (s, 1H), 7.32-7.43 (m, 3H), 7.56-7.71 (m, 4H): FABMS: 759 (M+H)$^+$.

This compound was prepared according to the method described for the compound 4b by reducing nitro compound (758 mg, 1.0 mmol) using SnCl$_2$.2H$_2$O (1.12 g, 5.0 mmol). The amino compound obtained was (704 mg, 97% yield).

This compound was prepared according to the method described for the compound 5b employing amine (728 mg, 1.0 mmol) and HgCl$_2$ (582 mg, 2.26 mmol), CaCO$_3$ (230 mg, 2.46 mmol) in acetonitrile-water (4:1) to obtain the pure product 10c (354 mg, 58% yield).).

$^1$H NMR (CDCl$_3$): δ 1.57-1.75 (m, 4H), 1.85-2.10 (m, 4H), 2.25 (s, 3H), 3.48-3.88 (m, 3H), 3.94 (s, 3H), 4.02-4.16 (m, 4H), 6.81 (s, 1H), 7.13-7.23 (m, 1H), 7.30-7.41 (m, 3H), 7.51 (s, 1H), 7.58 (d, 2H, J=2.493 Hz), 7.63 (s, 1H), 7.67 (d, 1H, J=4.985 Hz): FABMS: 605 (M+H)$^+$.

Example-9

7-methoxy-8-{5-[3-(3-chloro-4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (10d)

This compound was prepared according to the method described for the compound 3b by employing 2S—N-[4-(4-bromobutoxy)-5-methoxy-2-nitrobenzoyl]pyrrolidine-2-carboxaldehyde diethylthioacetal (1d) (549 mg, 1.0 mmol) was added anhydrous potassium carbonate (690 mg, 5.0 mmol) and 3-(3-chloro-4-fluorophenyl)-6-hydroxy-2-methyl-3,4-dihydro-4-quinazolinone (304 mg, 1.0 mmol). to obtain the pure nitro product (622 mg, 84% yield).

$^1$H NMR (CDCl$_3$): δ 1.24-1.44 (m, 10H), 1.67-1.83 (m, 2H), 1.88-2.06 (m, 6H), 2.1-2.24 (m, 2H), 2.25 (s, 3H), 2.67-2.92 (m, 4H), 3.18-3.36 (m, 2H), 3.97 (s, 3H), 4.07-4.20 (m, 4H), 4.67-4.77 (m, 1H), 4.86-4.91 (m, 1H), 6.82 (s, 1H), 7.32-7.43 (m, 3H), 7.56-7.71 (m, 4H): FABMS: 773 (M+H)$^+$.

This compound was prepared according to the method described for the compound 4b by reducing nitro compound (772 mg, 1.0 mmol) using SnCl$_2$.2H$_2$O (1.12 g, 5.0 mmol). The amino compound obtained was (720 mg, 97% yield).

This compound was prepared according to the method described for the compound 5b employing amine (742 mg, 1.0 mmol) and HgCl$_2$ (582 mg, 2.26 mmol), CaCO$_3$ (230 mg, 2.46 mmol) in acetonitrile-water (4:1) to obtain the pure product 10d (364 mg, 58% yield).).

$^1$H NMR (CDCl$_2$): δ 1.58-1.79 (m, 4H), 1.86-2.13 (m, 6H), 2.25 (s, 3H), 3.48-3.88 (m, 3H), 3.94 (s, 3H), 4.02-4.16 (m, 4H), 6.81 (s, 1H), 7.13-7.23 (m, 1H), 7.30-7.41 (m, 3H), 7.51 (s, 1H), 7.58 (d, 2H, J=2.493 Hz), 7.63 (s, 1H), 7.67 (d, 1H, J=4.985 Hz): FABMS: 619 (M+H)$^+$.

Example-10

7-methoxy-8-{5-[3-(4-iodo-2-methylphenyl)-2-methyl-4-oxo-34-dihydro-6-quinazolinyl]oxypentyloxy}-(11aS)-1,2,3,11a-tetrahydro-5H-pyrrolo[2,1-c][1,4]benzodiazepine-5-one (12b)

This compound was prepared according to the method described for the compound 3b by employing 2S—N-[4-(3-bromopropoxy)-5-methoxy-2-nitrobenzoyl]pyrrolidine-2-carboxaldehyde diethylthioacetal (1b) (521 mg, 1.0 mmol) was added anhydrous potassium carbonate (690 mg, 5.0 mmol) and 6-hydroxy-3-(4-iodo-2-methylphenyl)-2-methyl-3,4-dihydro-4-quinazolinone (392 mg, 1.0 mmol). to obtain the pure nitro product (698.8 mg, 84% yield).

$^1$H NMR (CDCl$_3$): δ 1.30-1.46 (m, 6H), 1.72-1.79 (m, 2H), 1.89-2.02 (m, 4H), 2.04-2.16 (m, 2H), 2.08 (s, 3H), 2.13 (s, 3H), 2.61-2.91 (m, 4H), 3.13-3.32 (m, 2H), 3.95 (s, 3H), 4.02-4.22 (m, 4H), 4.58-4.74 (m, 1H), 4.77-4.87 (m, 1H), 6.77 (s, 1H), 6.89 (d, 1H, J=7.411 Hz), 7.21-7.39 (m, 2H), 7.50-7.70 (m, 4H), 7.74 (d, 1H, J=7.411 Hz): FABMS: 833 (M+H)$^+$.

This compound was prepared according to the method described for the compound 4b by reducing nitro compound (832 mg, 1.0 mmol) using SnCl$_2$.2H$_2$O (1.12 g, 5.0 mmol). The amino compound obtained was (778 mg, 97% yield).

This compound was prepared according to the method described for the compound 5b employing amine (802 mg, 1.0 mmol) and HgCl$_2$ (582 mg, 2.26 mmol), CaCO$_3$ (230 mg, 2.46 mmol) in acetonitrile-water (4:1) to obtain the pure product 12b (394 mg, 58% yield).).

$^1$H NMR (CDCl$_3$): δ 1.84-2.09 (m, 6H), 2.08 (s, 3H), 2.16 (s, 3H), 3.51-3.88 (m, 3H), 3.94 (s, 3H), 4.02-4.16 (m, 4H), 6.81 (s, 1H), 6.90 (d, 1H, J=8.309 Hz), 7.33-7.40 (m, 1H), 7.51 (s, 1H), 7.62 (d, 2H, J=3.324 Hz), 7.69 (d, 1H, J=2.493 Hz), 7.75 (d, 1H, J=8.309 Hz): FABMS: 679 (M+H)$^+$.

Example-11

7-methoxy-8-{4-[3-(4-iodo-2-methylphenyl)-2-methyl-4-oxo-34-dihydro-6-quinazolinyl]oxybutoxy}-(11aS)-1,2,3,11a-tetrahydro-5H-pyrrolo[2,1-c][1,4]benzodiazepine-5-one (12c)

This compound was prepared according to the method described for the compound 3b by employing 2S—N-[4-(4-bromobutoxy)-5-methoxy-2-nitrobenzoyl]pyrrolidine-2-carboxaldehyde diethylthioacetal (1c) (535 mg, 1.0 mmol) was added anhydrous potassium carbonate (690 mg, 5.0 mmol) and 6-hydroxy-3-(4-iodo-2-methylphenyl)-2-methyl-3,4-dihydro-4-quinazolinone (392 mg, 1.0 mmol). to obtain the pure nitro product (710.6 mg, 84% yield).

$^1$H NMR (CDCl$_3$): δ 1.30-1.46 (m, 10H), 1.89-2.02 (m, 4H), 2.04-2.16 (m, 2H), 2.08 (s, 3H), 2.13 (s, 3H), 2.61-2.91 (m, 4H), 3.13-3.32 (m, 2H), 3.95 (s, 3H), 4.02-4.22 (m, 4H), 4.58-4.74 (m, 1H), 4.77-4.87 (m, 1H), 6.77 (s, 1H), 6.89 (d, 1H, J=7.411 Hz), 7.21-7.39 (m, 2H), 7.50-7.70 (m, 4H), 7.74 (d, 1H, J=7.411 Hz): FABMS: 847 (M+H)$^+$.

This compound was prepared according to the method described for the compound 4b by reducing nitro compound (846 mg, 1.0 mmol) using SnCl$_2$.2H$_2$O (1.12 g, 5.0 mmol). The amino compound obtained was (791.6 mg, 97% yield).

This compound was prepared according to the method described for the compound 5b employing amine (816 mg, 1.0 mmol) and HgCl$_2$ (582 mg, 2.26 mmol), CaCO$_3$ (230 mg, 2.46 mmol) in acetonitrile-water (4:1) to obtain the pure product 12c (402 mg, 58% yield).).

$^1$H NMR (CDCl$_3$): δ 1.57-1.75 (m, 4H), 1.85-2.10 (m, 4H), 2.08 (s, 3H), 2.16 (s, 3H), 3.51-3.88 (m, 3H), 3.94 (s, 3H), 4.02-4.16 (m, 4H), 6.81 (s, 1H), 6.90 (d, 1H, J=8.309 Hz), 7.33-7.40 (m, 1H), 7.51 (s, 1H), 7.62 (d, 2H, J=3.324 Hz), 7.69 (d, 1H, J=2.493 Hz), 7.75 (d, 1H, J=8.309 Hz): FABMS: 693

Example-12

7-methoxy-8-{5-[3-(4-iodo-2-methylphenyl)-2-methyl-4-oxo-34-dihydro-6-quinazolinyl]oxypentyloxy}-(11aS)-1,2,3,11a-tetrahydro-5H-pyrrolo[2,1-c][1,4]benzodiazepine-5-one (12d)

This compound was prepared according to the method described for the compound 3b by employing 2S—N-[4-(4-bromobutoxy)-5-methoxy-2-nitrobenzoyl]pyrrolidine-2-carboxaldehyde diethylthioacetal (1d) (549 mg, 1.0, mmol) was added anhydrous potassium carbonate (690 mg, 5.0 mmol) and 6-hydroxy-3-(4-iodo-2-methylphenyl)-2-methyl-3,4-dihydro-4-quinazolinone (392 mg, 1.0 mmol). to obtain the pure nitro product (722 mg, 84% yield).

$^1$H NMR (CDCl$_3$): δ 1.20-1.52 (m, 10H), 1.67-1.83 (m, 2H), 1.88-2.06 (m, 6H), 2.08 (s, 3H), 2.13 (s, 3H), 2.61-2.91 (m, 4H), 3.13-3.32 (m, 2H), 3.95 (s, 3H), 4.02-4.22 (m, 4H), 4.58-4.74 (m, 1H), 4.77-4.87 (m, 1H), 6.77 (s, 1H), 6.89 (d, 1H, J=7.411 Hz), 7.21-7.39 (m, 2H), 7.50-7.70 (m, 4H), 7.74 (d, 1H, J=7.411 Hz): FABMS: 861 (M+H)$^+$.

This compound was prepared according to the method described for the compound 4b by reducing nitro compound (860 mg, 1.0 mmol) using SnCl$_2$.2H$_2$O (1.12 g, 5.0 mmol). The amino compound obtained was (805 mg, 97% yield).

This compound was prepared according to the method described for the compound 5b employing amine (830 mg, 1.0 mmol) and HgCl$_2$ (582 mg, 2.26 mmol), CaCO$_3$ (230 mg, 2.46 mmol) in acetonitrile-water (4:1) to obtain the pure product 12d (420 mg, 58% yield).).

$^1$H NMR (CDCl$_3$): δ 1.59-1.75 (m, 4H), 1.84-2.02 (m, 6H), 2.08 (s, 3H), 2.16 (s, 3H), 3.51-3.88 (m, 3H), 3.94 (s, 3H), 4.02-4.16 (m, 4H), 6.81 (s, 1H), 6.90 (d, 1H, J=8.309 Hz), 7.33-7.40 (m, 1H), 7.51 (s, 1H), 7.62 (d, 2H, J=3.324 Hz), 7.69 (d, 1H, J=2.493 Hz), 7.75 (d, 1H, J=8.309 Hz): FABMS: 707 (M+H)$^+$.

Biological Activity:

Some of in vitro biological activity studies were carried out at the National Cancer Institute, Marryland, USA. and Tata Fundamental Reasearch Institute, Mumbai, India.

In Vitro Cytotoxicity

The C8-linked quinazolinone-PBD hybrid (5d) has been tested against sixty human tumour cell lines derived from nine cancer types (leukemia, non-small cell lung cancer, colon cancer, CNS cancer, melanoma, ovarian cancer, renal cancer, prostate cancer and breast cancer) as per NCI protocol. For each compound, dose response curves for individual cell lines have been measured at a minimum of five concentrations at 10 fold dilutions. A protocol of 48 h continuous drug exposure has been used, and a sulforhodamine B (SRB) protein assay was used to estimate cell viability or growth. The concentration for 50% cell growth inhibition ($GI_{50}$), total cell growth inhibition (TGI, 0% growth) and 50% cell death ($LC_{50}$, 50% growth) compared with the control has been calculated (Table-1). Compound 5d has been evaluated for their in vitro cytotoxicity in sixty cell lines from nine human cancer types of lung (Hop-62, NCI-H226, NCI-H522), leukemia (K-562, SR), colon (HCT-116, HCT-15, HCC-2998), CNS(SF-539), melanoma (SK-MEL-5, UACC-62, M14), ovarian (IGROV1), renal (A498), prostate (PC3) breast (BT-549, MDA-MB-435, HS578T) origin. The results are expressed as percent of cell growth determined relative to that of untreated control cells (Table 2). The representative compound 5d has shown significant cytotoxicity against some cancer cell lines.

TABLE 1

$Log_{10}$ $GI_{50}$ (concentration in mol/L causing 50% growth inhibition) values for quinazolinone-PBD hybrid (5d)

| | $Log_{10}$ GI50 | $Log_{10}$ LC50 |
|---|---|---|
| Leukemia | −6.85 | −5.30 |
| Non-small-celllung | −6.59 | −5.02 |
| Colon | −6.59 | −5.49 |
| CNS | −6.59 | −4.88 |
| Melanoma | −6.65 | −5.90 |
| Ovarian | −6.52 | −4.79 |
| Renal | −6.62 | −5.09 |
| Prostate | −6.55 | −5.19 |
| Breast | −6.66 | −4.90 |

Each cancer type represents the average of six to eight different cancer cell lines.

The compound 5d exhibits a wide spectrum of activity against sixty cell lines in nine cell panels, with $GI_{50}$ value of <1.73 μm. In the non-small cell lung cancer panel, the growth of NCI-H460, NCI-H226, NCI-H522 cell lines were affected by compound 5d with $GI_{50}$ values as 0.20, 0.16 and 0.12 μM respectively. The $GI_{50}$ values of compound 5d against colon cancer HCT-116, SW-620, KM12, COLO 205 cell lines are 0.15, 0.16, 0.17 and 0.18 μm respectively. The $GI_{50}$ values for compound 5d against leukemia K-562, SR cell lines are 0.06, 0.11 μm The $GI_{50}$ values for compound 5d against CNS U251 cell line is 0.16 μm The $GI_{50}$ values for compound 5d against melanoma LOX IMVI, UACC-62, SK-MEL-5, M14 cell lines are 0.15, 0.16, 0.16 μm and 0.17 μm The $GI_{50}$ values for compound 5d against ovarian IGROV1 cell line is 0.18 μM The $GI_{50}$ values for compound 5d against renal A498 cell line is 0.16 μm The $GI_{50}$ values for compound 5d against prostate DU-145 cell line is 0.26 μm. The $GI_{50}$ values for compound 5d against breast MCF7, MDA-MB-231/ATCC, HS 578T, MDA-MB-435, BT-549, T-47D, MDA-MB-468, cell lines are 017, 0.17, 0.16, 0.16, 0.11, 0.17, 0.16 μm.

Compound 5d exhibits activity against sixty cell lines in nine cancer cell panels with $GI_{50}$ values of <1.73 μm. in vitro cytotoxicity of compound 5d in selected cancer cell lines has been illustrated in Table 2. The average $GI_{50}$ values for each cancer panel of compounds 5d have been illustrated in Table 3.

TABLE 2

In vitro cytotoxicity of compounds 5d in sixty cancer cell lines

| Cancer panel/cell line | $GI_{50}$ (μm) 5d | Cancer panel/cell line | $GI_{50}$ (μm) 5d |
|---|---|---|---|
| Leukemia | | Ovarian | |
| CCRF-CEM | 0.16 | IGROV1 | 0.18 |
| HL-60(TB) | 0.18 | OVCAR-3 | 0.20 |
| K-562 | 0.06 | OVCAR-4 | 0.37 |
| MOLT-4 | 0.19 | OVCAR-5 | 0.33 |
| RPMI-8226 | 0.19 | OVCAR-8 | 0.34 |
| SR | 0.11 | SK-OV-3 | 0.43 |
| Non-small cell lung | | Renal | |
| A549/ATCC | 0.23 | 786-0 | 0.17 |
| EKVX | 0.87 | A498 | 0.16 |
| HOP-92 | 0.35 | ACHN | 0.29 |
| NCI-H226 | 0.16 | CAKI-1 | 0.19 |
| NCI-H23 | 0.23 | RXF 393 | 0.21 |
| NCI-H322M | 0.26 | SN12C | 0.24 |
| NCI-H460 | 0.20 | TK-10 | 0.31 |
| NCI-H522 | 0.12 | UO-31 | 0.36 |
| Colon | | Prostate | |
| COLO 205 | 0.18 | PC-3 | 0.29 |
| HCC-2998 | 0.26 | DU-145 | 0.26 |
| HCT-116 | 0.15 | | |
| HCT-15 | 1.09 | | |
| HT29 | 0.26 | | |
| KM12 | 0.17 | | |
| SW-620 | 0.16 | | |
| CNS | | Breast | |
| SF-268 | 0.26 | MCF7 | 0.17 |
| SF-539 | 0.22 | NCI/ADR-RES | 1.73 |
| SNB-19 | 0.28 | | |
| SNB-75 | 0.38 | MDA-MB-231/ATCC | 0.17 |
| U251 | 0.16 | | |
| | | HS 578T | 0.16 |
| | | MDA-MB-435 | 0.16 |
| | | BT-549 | 0.11 |
| | | T-47D | 0.17 |
| | | MDA-MB-468 | 0.16 |
| Melanoma | | Melanoma | |
| LOX IMVI | 0.15 | SK-MEL-28 | 0.20 |
| MALME-3M | 0.23 | | |
| M14 | 0.17 | SK-MEL-5 | 0.16 |
| SK-MEL-2 | 0.42 | UACC-257 | 0.39 |
| | | UACC-62 | 0.16 |

The mean graph mid point values of $log_{10}$ TGI and $log_{10}$ $LC_{50}$ as well as $log_{10}$ $GI_{50}$ for 5d is listed in Table-4. As demonstrated by mean graph pattern, compounds 5d exhibit an interesting profile of activity and selectivity for various cell lines. The mean graph mid points of $log_{10}$ TGI and $log_{10}$ $LC_{50}$ have shown similar pattern to the $log_{10}$ $GI_{50}$ mean graph mid points.

TABLE 3

$log_{10}$ $GI_{50}$, $log_{10}$ TGI and $log_{10}$ $LC_{50}$ mean graphs midpoints (MG_MID) of in vitro cytotoxicity data for the compound 5d against human tumour cell lines.

| Compound | $Log_{10}$ $GI_{50}$ | $Log_{10}$ TGI | $Log_{10}$ $LC_{50}$ |
|---|---|---|---|
| 5d | −6.63 | −6.15 | −5.21 |

The C8-linked quinazolinone-PBD hybrids (5b, 5c, 5k, 5l, 5m) have been tested against eleven human tumour cell lines derived from seven cancer types (lung cancer, colon cancer, cervix, ovarian cancer, oral cancer, prostate cancer and breast cancer) as per Tata protocol. For each compound, dose response curves for individual cell lines have been measured at a minimum of five concentrations at 10 fold dilutions. A protocol of 48 h continuous drug exposure has been used, and a sulforhodamine B (SRB) protein assay was used to estimate cell viability or growth. Compounds 5b, 5c, 5k, 5l, 5m have been evaluated for their in vitro cytotoxicity in eleven cell lines from seven human cancer types of lung (Hop-62, A-549) colon (COLO-205) cervix (Si-Ha), ovary (A-2780), prostate (PC3) breast (MCF7, Zr-75-1), oral (DWD, GURAV, KB). The results are expressed as percent of cell growth determined relative to that of untreated control cells (Table-4).

Among the compounds 5b, 5c, 5k, 5l, 5m the compound 5b exhibits a wide spectrum of activity against eleven cell lines in seven cell panels, with $GI_{50}$ value of <1.83 μm. In the lung cancer panel, the growth of Hop-62, A-549 cell lines were affected by compound 5b with $GI_{50}$ values as 0.16 and 1.48 μM respectively. The $GI_{50}$ value of compound 5b against colon cancer COLO 205 cell line is 0.14 μm. The $GI_{50}$ value of compound 5b against cervix cancer Si-Ha cell line is 0.16 μm. The $GI_{50}$ value of compound 5b against prostate cancer PC-3 cell line is 0.13 μm. The $GI_{50}$ values for compound 5b against oral cancer DWD, GURAV, KB cell lines are 0.11, 0.13, 0.15 μm respectively. The $GI_{50}$ values for compound 5b against breast MCF7, Zr-75-1 cell lines are 1.83, 0.16 μm respectively.

Compounds 5b, 5c, 5k, 5l, 5m exhibits activity against eleven cell lines in seven cancer cell panels with $GI_{50}$ values of <2.5 μm. in vitro cytotoxicity of compounds 5b, 5c, 5k, 5l, 5m in selected cancer cell lines has been illustrated in Table 4.

TABLE 4

In vitro cytotoxicity of compounds 5b, 5c, 5k, 5l, 5m in selected cancer cell lines

| Cancer panel/cell line | $GI_{50}$ (μm) | | | | |
|---|---|---|---|---|---|
| | 5b | 5c | 5k | 5l | 5m |
| Lung | | | | | |
| HOP-62 | 0.16 | 1.95 | 2.15 | 2.33 | 2.31 |
| A-549 | 1.48 | 1.93 | 1.88 | 2.39 | 2.62 |
| Oral | | | | | |
| DWD | 0.11 | 1.60 | 0.14 | 0.16 | 0.17 |
| GURAV | 0.13 | 1.95 | 1.85 | 1.93 | 1.82 |
| KB | 0.15 | 1.98 | 1.78 | 2.07 | 2.15 |
| Ovary | | | | | |
| A-2780 | 0.10 | 0.16 | 0.14 | 0.16 | 0.15 |
| Prostate | | | | | |
| PC-3 | 0.13 | 0.17 | 0.16 | 1.91 | 1.83 |
| Cervix | | | | | |
| Si-Ha | 0.16 | 1.91 | 2.00 | 2.19 | 2.08 |
| Colon | | | | | |
| Colo-205 | 0.14 | 1.81 | 2.12 | 2.23 | 2.00 |
| Breast | | | | | |
| Zr-75-1 | 0.16 | 1.97 | 0.17 | 2.44 | 2.09 |
| MCF7 | 1.83 | 2.30 | 2.03 | NA | 2.50 |

DNA-Binding Ability of Novel C8-Linked Quinazolinone-PBD Hybrids
Thermal Denaturation Studies Compounds have been subjected to thermal denaturation studies with duplex-form calf thymus DNA (CT-DNA) using a modification of a reported procedure. Working solutions in aqueous buffer (10 μm $NaH_2PO_4/Na_2HPO_4$, 1 mM $Na_2EDTA$, pH 7.00+0.01). containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 hrs prior to analysis. Samples have been monitored at 260 nm using a Beckman DU-800 spectrophotometer fitted with high performance temperature controller, and heated at 1° C. $\min^{-1}$ in the 40-110° C. range. DNA helix→coil transition temperatures ($T_m$) have been obtained from the maxima in the $d(A_{260})/dT$ derivative plots. Drug-induced alterations in DNA melting behavior are given by: $\Delta T_m = T_m(DNA+PBD) - T_m(DNA$ alone), where the $T_m$ value for the PBD-free CT-DNA is 68.5±0.01. The fixed [PBD]/[DNA] ratio used has not resulted in binding saturation of the host DNA duplex for any compound examined.

The DNA-binding for these novel C8-linked quinazolinone-PBD hybrids has been examined by thermal denaturation studies using calf thymus (CT) DNA. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. Data for 5b, 5c, 5d, and 5k, 5l, 5m and DC-81 are included in Table 5 for comparison.

TABLE 5

Thermal denaturation data for quinazolinone-PBD hybrids with calf thymus (CT) DNA

| PBD hybrids | [PBD]:[DNA] molar ratio[b] | $\Delta T_m$ ((° C.)[a] after incubation at 37° C. for | |
|---|---|---|---|
| | | 0 h | 18 h |
| 5b | 1:5 | 1.0 | 2.0 |
| 5c | 1:5 | 1.0 | 2.1 |
| 5d | 1:5 | 1.1 | 2.3 |
| 5k | 1:5 | 1.0 | 2.0 |
| 5l | 1:5 | 1.2 | 2.3 |
| 5m | 1:5 | 1.1 | 2.1 |
| DC-81 | 1:5 | 0.3 | 0.7 |

[a]For CT-DNA alone at pH 7.00 ± 0.01, $T_m$ = 68.5° C. ± 0.01 (mean value from 10 separate determinations), all $\Delta T_m$ values are ±0.1-0.2° C.
[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].
[c]The $\Delta T_m$ for PBD hybrids 5b, 5c, 5d, 5k, 5l and 5m at a [PBD]:[DNA] molar ratio of 1:5 increased to a value of 2.0° C., 2.1° C., 2.3° C., 2.0° C., 2.3° C. and 2.1° C. after 18 h incubation respectively.

Significance of the Work Carried Out

The novel C8-linked quinazolinone-PBD hybrids that have been synthesized exhibited significant DNA-binding ability and showed cytotoxic activity against sixty human tumour cell lines.

ADVANTAGES OF THE INVENTION

1. The present invention provides a new pyrrolo[2,1-c][1,4] benzodiazepine hybrids useful as antitumour agents.
2. It also provides a process for the preparation of novel pyrrolo[2,1-c][1,4]benzodiaze-pine hybrids.

We claim:

1. A compound of formula A:

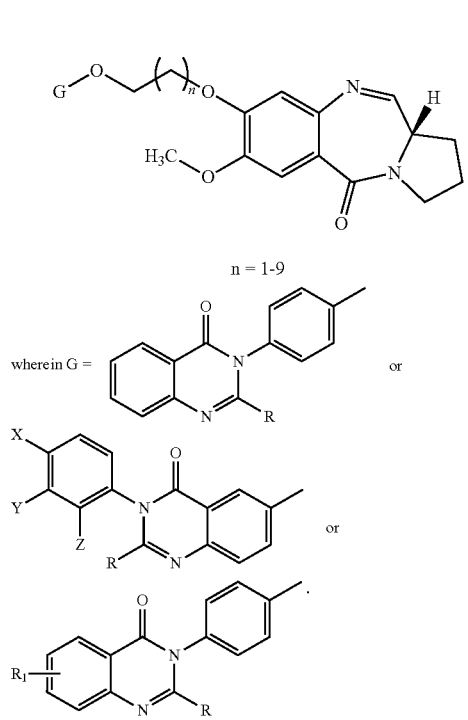

n = 1-9 wherein G =

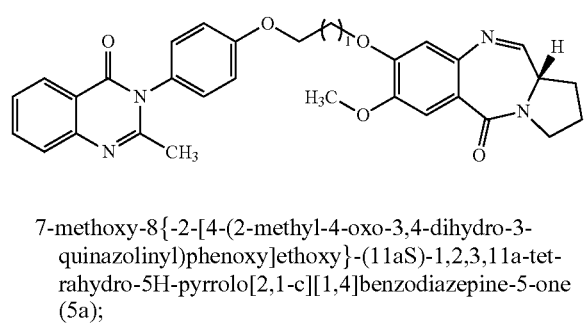

R = Methyl, styryl, phenyl;
R₁ = H, halo, pyrrolidine, piperidine, 4-methyl piperidine or morpholine;
X, Y, Z = H, halo, alkyl or alkoxy.

2. The compound as claimed in claim 1, selected from the group consisting of:

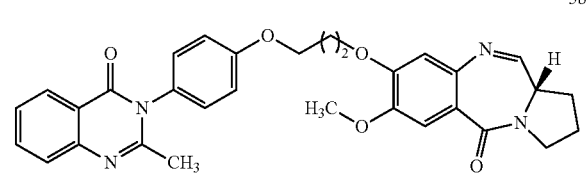

7-methoxy-8{-2-[4-(2-methyl-4-oxo-3,4-dihydro-3-quinazolinyl)phenoxy]ethoxy}-(11aS)-1,2,3,11a-tetrahydro-5H-pyrrolo[2,1-c][1,4]benzodiazepine-5-one (5a);

7-methoxy-8{-3-[4-(2-methyl-4-oxo-3,4-dihydro-3-quinazolinyl)phenoxy]propoxy}-(11aS)-1,2,3,11a-tetrahydro-5H-pyrrolo[2,1-c][1,4]benzodiazepine-5-one (5b);

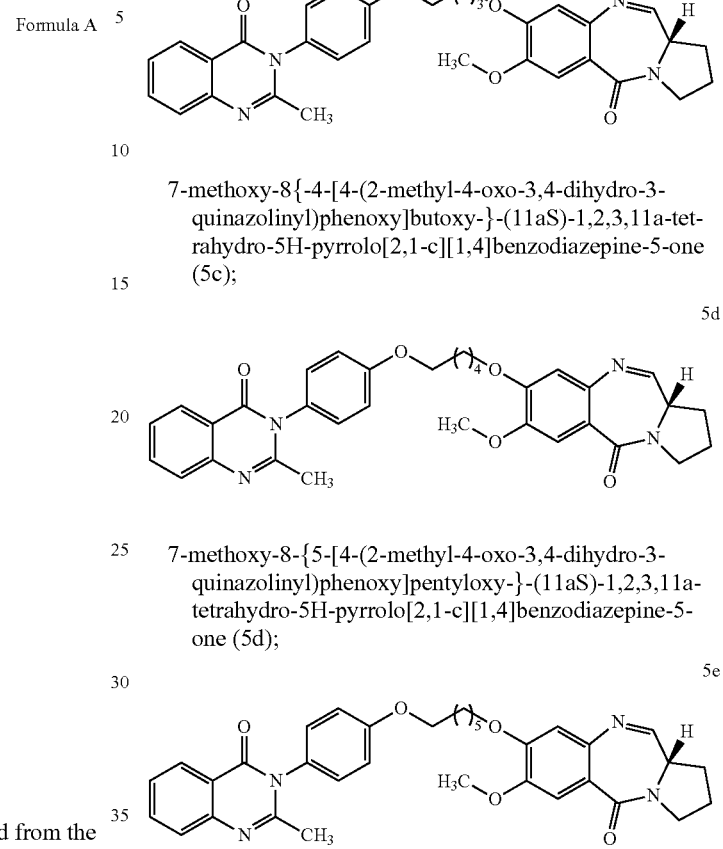

7-methoxy-8{-4-[4-(2-methyl-4-oxo-3,4-dihydro-3-quinazolinyl)phenoxy]butoxy-}-(11aS)-1,2,3,11a-tetrahydro-5H-pyrrolo[2,1-c][1,4]benzodiazepine-5-one (5c);

7-methoxy-8-{5-[4-(2-methyl-4-oxo-3,4-dihydro-3-quinazolinyl)phenoxy]pentyloxy-}-(11aS)-1,2,3,11a-tetrahydro-5H-pyrrolo[2,1-c][1,4]benzodiazepine-5-one (5d);

7-methoxy-8{-6-[4-(2-methyl-4-oxo-3,4-dihydro-3-quinazolinyl)phenoxy]hexyloxy}-(11aS)-1,2,3,11a-tetrahydro-5H-pyrrolo[2,1-c][1,4]benzodiazepine-5-one (5e);

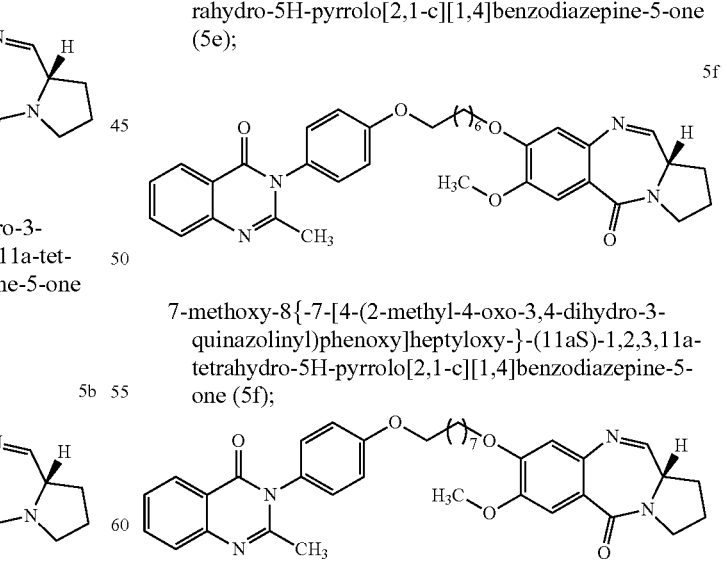

7-methoxy-8{-7-[4-(2-methyl-4-oxo-3,4-dihydro-3-quinazolinyl)phenoxy]heptyloxy-}-(11aS)-1,2,3,11a-tetrahydro-5H-pyrrolo[2,1-c][1,4]benzodiazepine-5-one (5f);

7-methoxy-8-{-8-[4-(2-methyl-4-oxo-3,4-dihydro-3-quinazolinyl)phenoxy]octyloxy-}-(11aS)-1,2,3,11a-tetrahydro-5H-pyrrolo[2,1-c][1,4]benzodiazepine-5-one (5g);

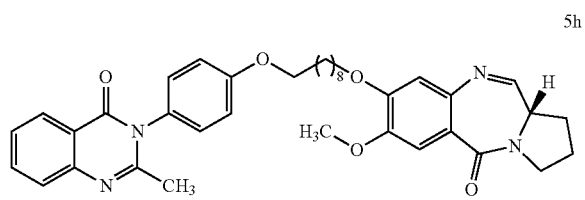

7-methoxy-8{-9-[4-(2-methyl-4-oxo-3,4-dihydro-3-quinazolinyl)phenoxy]nonyloxy}-(11aS)-1,2,3,11a-tetrahydro-5H-pyrrolo[2,1-c][1,4]benzodiazepine-5-one (5h);

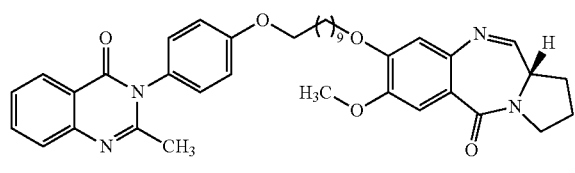

7-methoxy-8{-10-[4-(2-methyl-4-oxo-3,4-dihydro-3-quinazolinyl)phenoxy]decyloxy-}-(11aS)-1,2,3,11a-tetrahydro-5H-pyrrolo[2,1-c][1,4]benzodiazepine-5-one (5i);

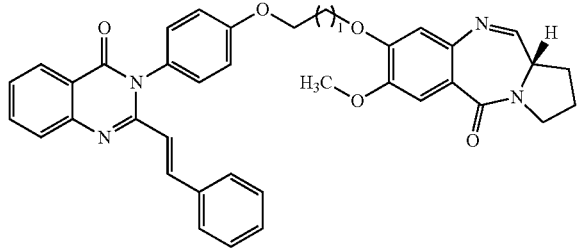

7-methoxy-8-{-2-[(4-4-oxo-2-[(E)-2-phenyl-1-ethenyl]-3,4-dihydro-3-quinazolinylphenyl)oxy]ethoxy}-(11aS)-1,2,3,11a-tetrahydro-5H-pyrrolo[2,1-c][1,4]benzodiazepine-5-one (5j);

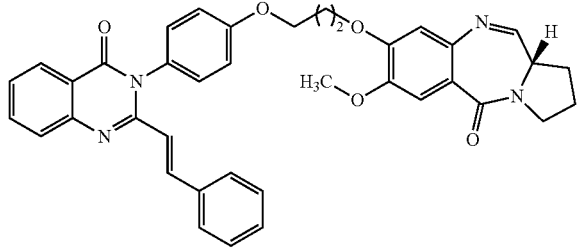

7-methoxy-8-{3-[(4-4-oxo-2-[(E)-2-phenyl-1-ethenyl]-3,4-dihydro-3-quinazolinylphenyl)oxy]propoxy}-(11aS)-1,2,3,11a-tetrahydro-5H-pyrrolo[2,1-c][1,4]benzodiazepine-5-one (5k);

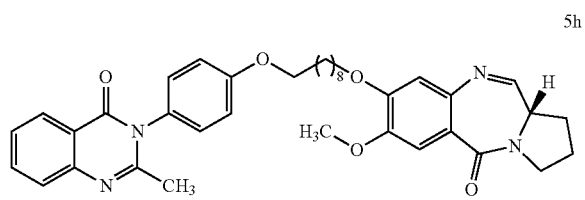

7-methoxy-8-{4-[(4-4-oxo-2-[(E)-2-phenyl-1-ethenyl]-3,4-dihydro-3-quinazolinylphenyl)oxy]butoxy}-(11aS)-1,2,3,11a-tetrahydro-5H-pyrrolo[2,1-c][1,4]benzodiazepine-5-one (5l);

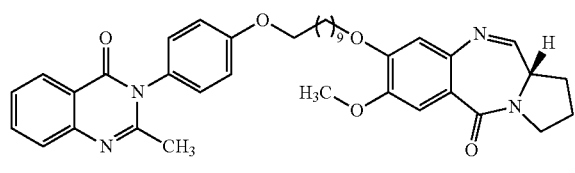

7-methoxy-8-{5-[(4-4-oxo-2-[(E)-2-phenyl-1-ethenyl]-3,4-dihydro-3-quinazolinylphenyl)oxy]pentyloxy}-(11aS)-1,2,3,11a-tetrahydro-5H-pyrrolo[2,1-c][1,4]benzodiazepine-5-one (5m);

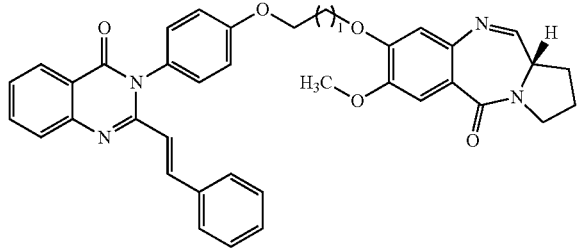

7-methoxy-8-{-6-[(4-4-oxo-2-[(E)-2-phenyl-1-ethenyl]-3,4-dihydro-3-quinazolinylphenyl)oxy]hexyloxy}-(11aS)-1,2,3,11a-tetrahydro-5H-pyrrolo[2,1-c][1,4]benzodiazepine-5-one (5n);

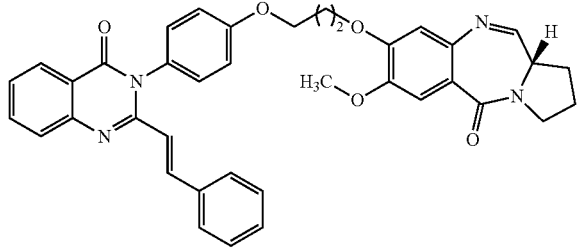

7-methoxy-8-{-7-[(4-4-oxo-2-[(E)-2-phenyl-1-ethenyl]-3,4-dihydro-3-quinazolinylphenyl)oxy]heptyloxy}-(11aS)-1,2,3,11a-tetrahydro-5H-pyrrolo[2,1-c][1,4]benzodiazepine-5-one (5o);

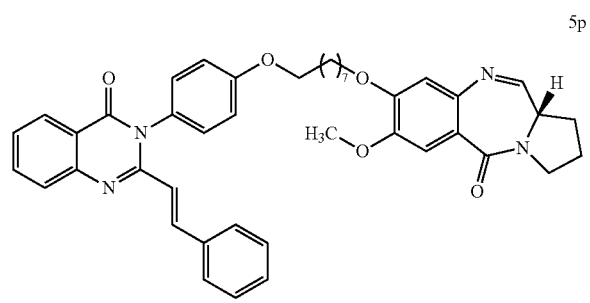

7-methoxy-8-{-8-[(4-4-oxo-2-[(E)-2-phenyl-1-ethenyl]-3,4-dihydro-3-quinazolinylphenyl)oxy]octyloxy}-(11aS)-1,2,3,11a-tetrahydro-5H-pyrrolo[2,1-c][1,4]benzodiazepine-5-one (5p);

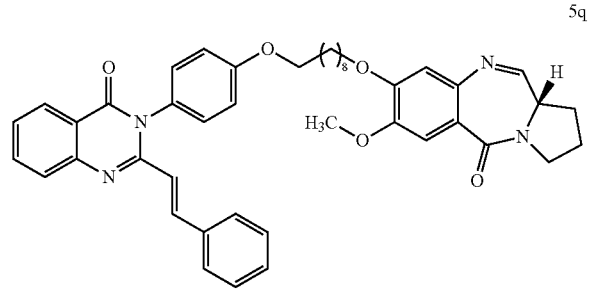

7-methoxy-8-{-9-[(4-4-oxo-2-[(E)-2-phenyl-1-ethenyl]-3,4-dihydro-3-quinazolinylphenyl)oxy]nonylyloxy}-(11aS)-1,2,3,11a-tetrahydro-5H-pyrrolo[2,1-c][1,4]benzodiazepine-5-one (5q);

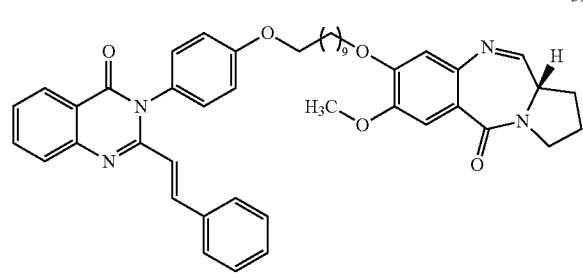

7-methoxy-8-{-10-[(4-4-oxo-2-[(E)-2-phenyl-1-ethenyl]-3,4-dihydro-3-quinazolinylphenyl)oxy]nonylyloxy}-(11aS)-1,2,3,11a-tetrahydro-5H-pyrrolo[2,1-c][1,4]benzodiazepine-5-one (5r);

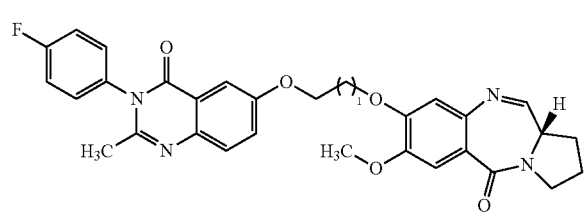

7-methoxy-8-{2-[3-(4-fluorophenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (9a);

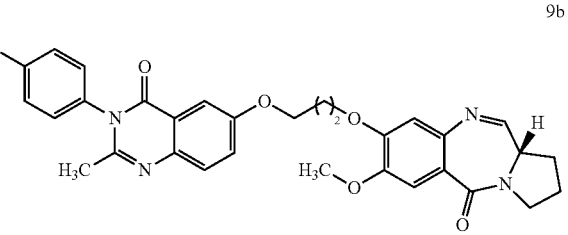

7-methoxy-8-{3-[3-(4-fluorophenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (9b);

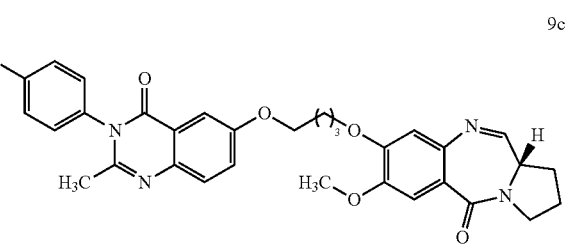

7-methoxy-8-{4-[3-(4-fluorophenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (9c);

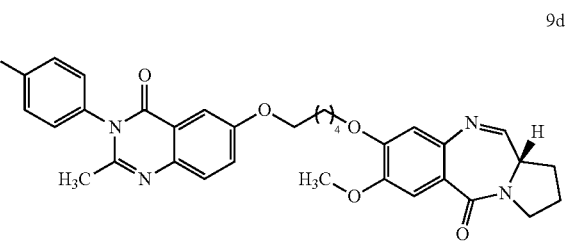

7-methoxy-8-{5-[3-(4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (9d);

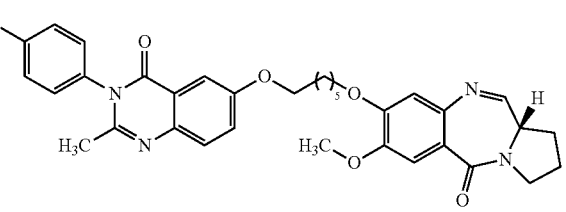

7-methoxy-8-{6-[3-(4-fluorophenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (9e);

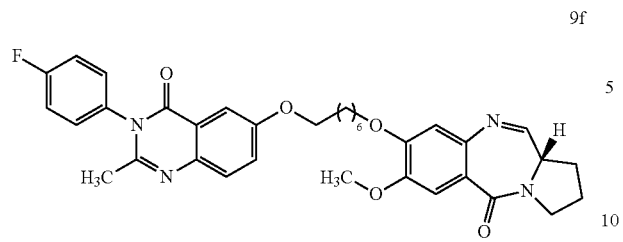

7-methoxy-8-{7-[3-(4-fluorophenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (9f);

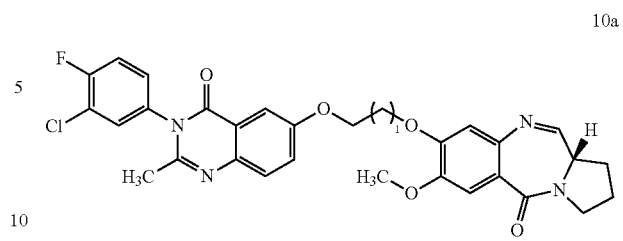

7-methoxy-8-{2-[3-(3-chloro-4-fluorophenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (10a);

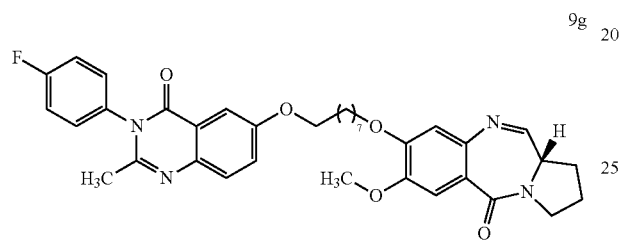

7-methoxy-8-{8-[3-(4-fluorophenyl)-2-methyl-4-oxo-3,4-dihydro-6-quinazolinyl]oxyoctyloxy}-(11aS)-1,2,3,11a-tetrahydro-5H-pyrrolo[2,1-c][1,4]benzodiazepine-5-one (9g);

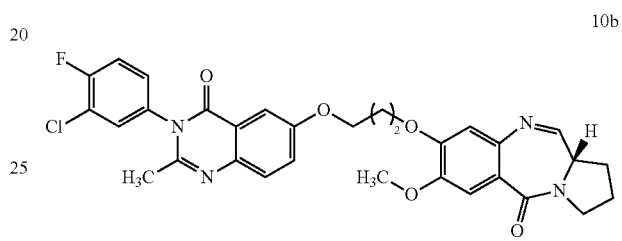

7-methoxy-8-{3-[3-(3-chloro-4-fluorophenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (10b);

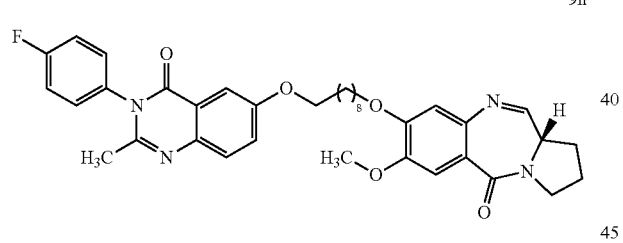

7-methoxy-8-{9-[3-(4-fluorophenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (9h);

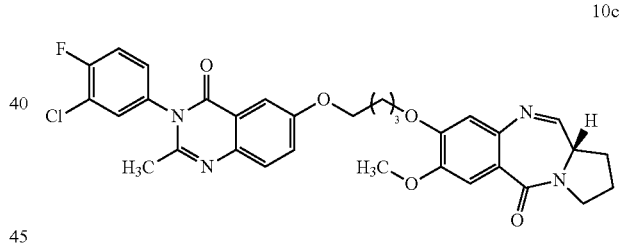

7-methoxy-8-{4-[3-(3-chloro-4-fluorophenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (10c);

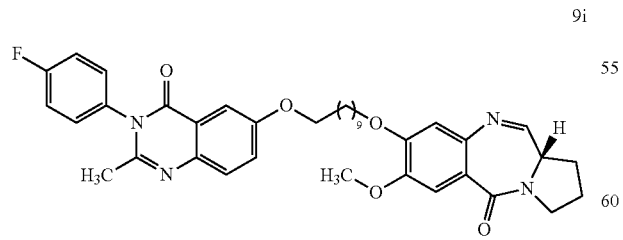

7-methoxy-8-{10-[3-(4-fluorophenyl)-2-methyl-4-oxo-3,4-dihydro-6-quinazolinyl]oxydecyloxy}-(11aS)-1,2,3,11a-tetrahydro-5H-pyrrolo[2,1-c][1,4]benzodiazepine-5-one (9i);

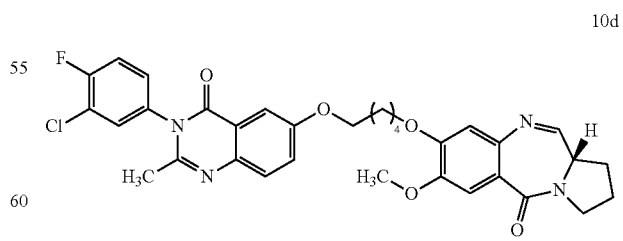

7-methoxy-8-{5-[3-(3-chloro-4-fluorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (10d);

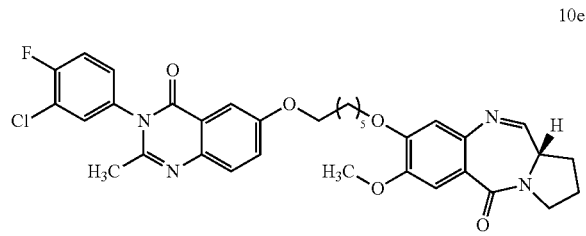

7-methoxy-8-{6-[3-(3-chloro-4-fluorophenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (10e);

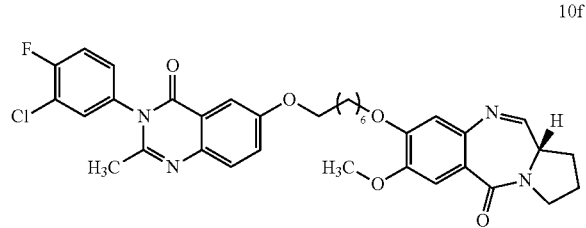

7-methoxy-8-{7-[3-(3-chloro-4-fluorophenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (10f);

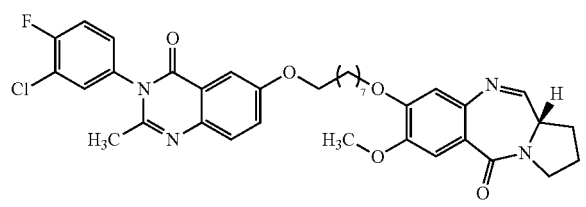

7-methoxy-8-{8-[3-(3-chloro-4-fluorophenyl)-2-methyl-4-oxo-3,4-dihydro-6-quinazolinyl]oxyoctyloxy}-(11aS)-1,2,3,11a-tetrahydro-5H-pyrrolo[2,1-c][1,4]benzodiazepine-5-one (10g);

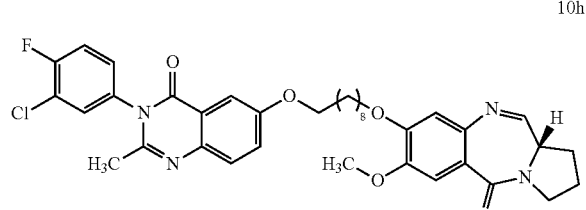

7-methoxy-8-{9-[3-(3-chloro-4-fluorophenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (10h);

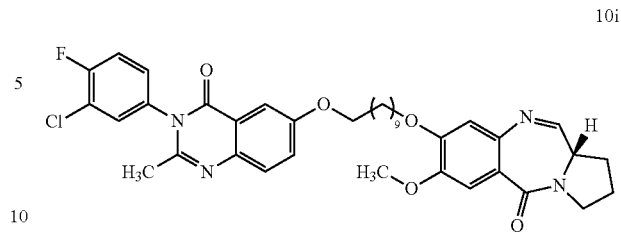

7-methoxy-8-{10-[3-(3-chloro-4-fluorophenyl)-2-methyl-4-oxo-3,4-dihydro-6-quinazolinyl]oxydecyloxy}-(11aS)-1,2,3,11a-tetrahydro-5H-pyrrolo[2,1-c][1,4]benzodiazepine-5-one (10i);

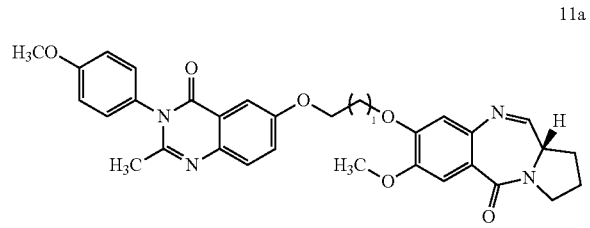

7-methoxy-8-{(2-[3-(4-methoxyphenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (11a);

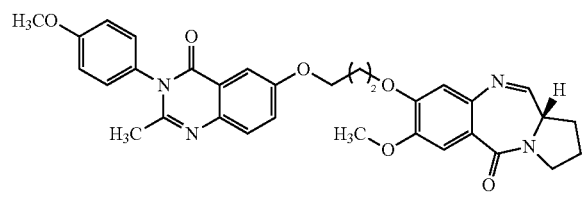

7-methoxy-8-{(3-[3-(4-methoxyphenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (11b);

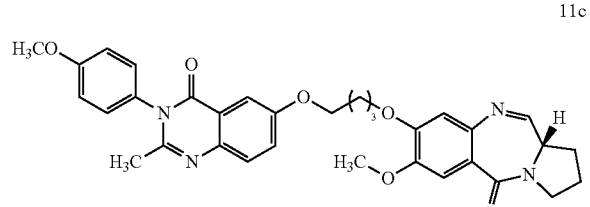

7-methoxy-8-{(4-[3-(4-methoxyphenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (11c);

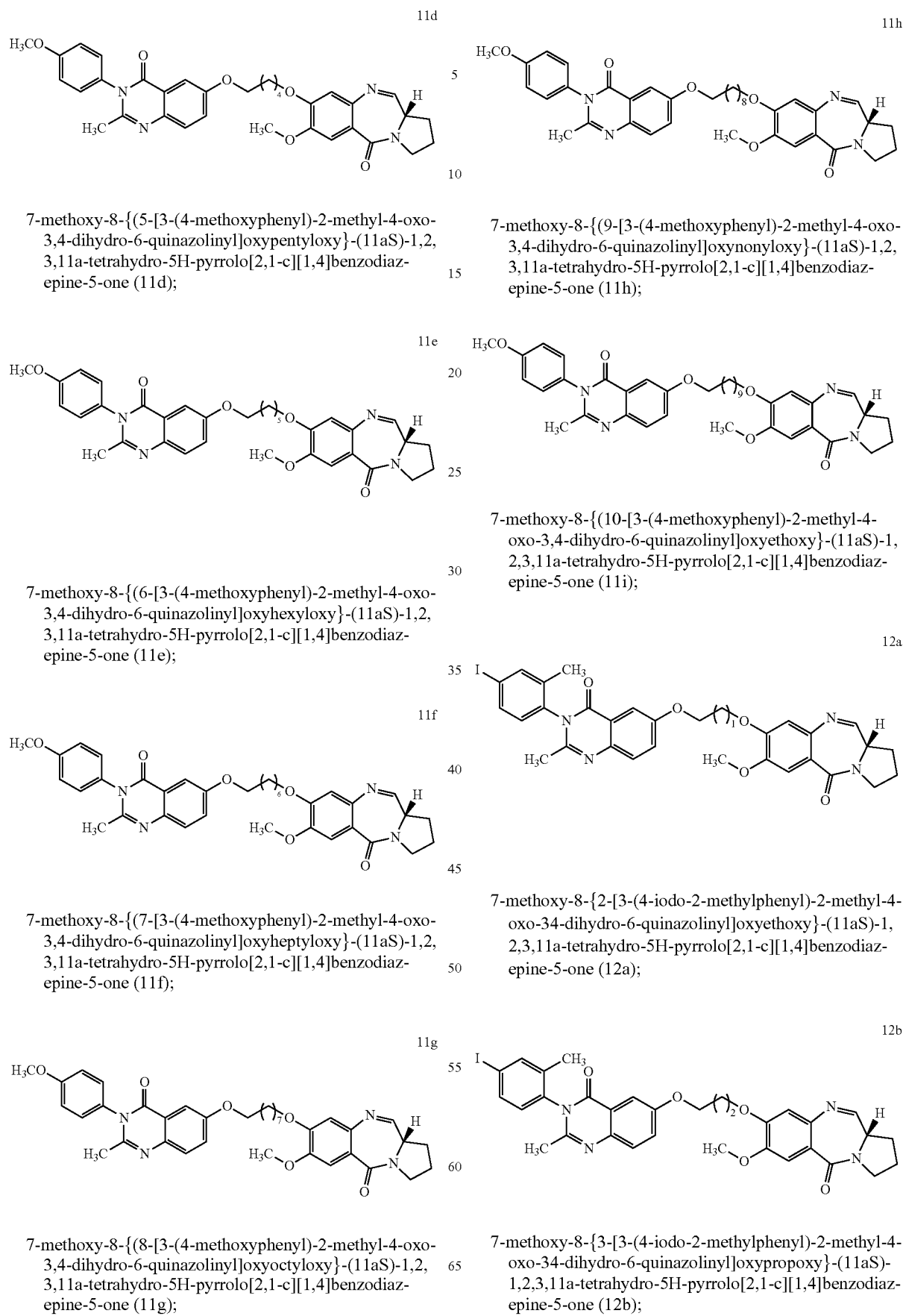

7-methoxy-8-{(5-[3-(4-methoxyphenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (11d);

7-methoxy-8-{(6-[3-(4-methoxyphenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (11e);

7-methoxy-8-{(7-[3-(4-methoxyphenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (11f);

7-methoxy-8-{(8-[3-(4-methoxyphenyl)-2-methyl-4-oxo-3,4-dihydro-6-quinazolinyl]oxyoctyloxy}-(11aS)-1,2,3,11a-tetrahydro-5H-pyrrolo[2,1-c][1,4]benzodiazepine-5-one (11g);

7-methoxy-8-{(9-[3-(4-methoxyphenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (11h);

7-methoxy-8-{(10-[3-(4-methoxyphenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (11i);

7-methoxy-8-{2-[3-(4-iodo-2-methylphenyl)-2-methyl-4-oxo-34-dihydro-6-quinazolinyl]oxyethoxy}-(11aS)-1,2,3,11a-tetrahydro-5H-pyrrolo[2,1-c][1,4]benzodiazepine-5-one (12a);

7-methoxy-8-{3-[3-(4-iodo-2-methylphenyl)-2-methyl-4-oxo-34-dihydro-6-quinazolinyl]oxypropoxy}-(11aS)-1,2,3,11a-tetrahydro-5H-pyrrolo[2,1-c][1,4]benzodiazepine-5-one (12b);

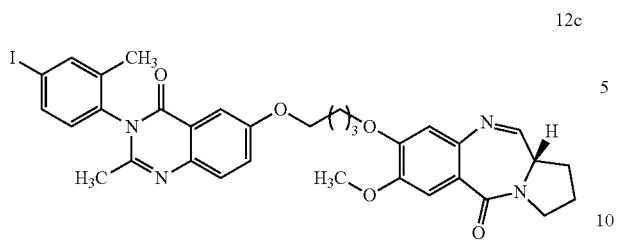

7-methoxy-8-{4-[3-(4-iodo-2-methylphenyl)-2-methyl-4-oxo-34-dihydro-6-quinazolinyl]oxybutoxy}-(11aS)-1,2,3,11a-tetrahydro-5H-pyrrolo[2,1-c][1,4]benzodiazepine-5-one (12c);

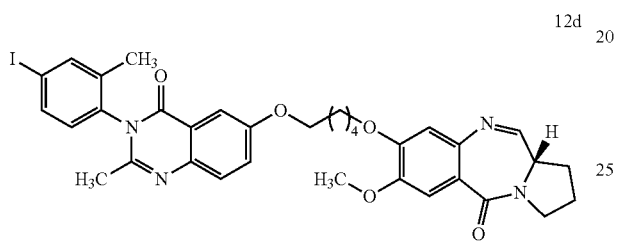

7-methoxy-8-{5-[3-(4-iodo-2-methylphenyl)-2-methyl-4-oxo-34-dihydro-6-quinazolinyl]oxypentyloxy}-(11aS)-1,2,3,11a-tetrahydro-5H-pyrrolo[2,1-c][1,4]benzodiazepine-5-one (12d);

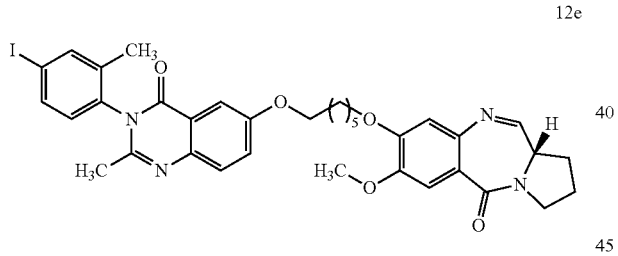

7-methoxy-8-{6-[3-(4-iodo-2-methylphenyl)-2-methyl-4-oxo-34-dihydro-6-quinazolinyl]oxyhexyloxy}-(11aS)-1,2,3,11a-tetrahydro-5H-pyrrolo[2,1-c][1,4]benzodiazepine-5-one (12e);

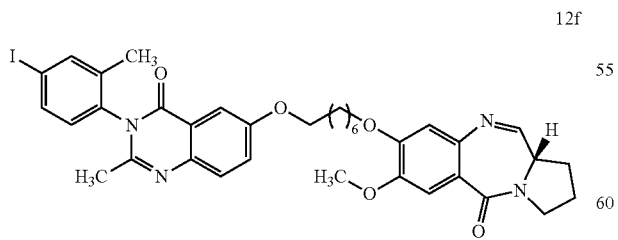

7-methoxy-8-{7-[3-(4-iodo-2-methylphenyl)-2-methyl-4-oxo-34-dihydro-6-quinazolinyl]oxyheptyloxy}-(11aS)-1,2,3,11a-tetrahydro-5H-pyrrolo[2,1-c][1,4]benzodiazepine-5-one (12f);

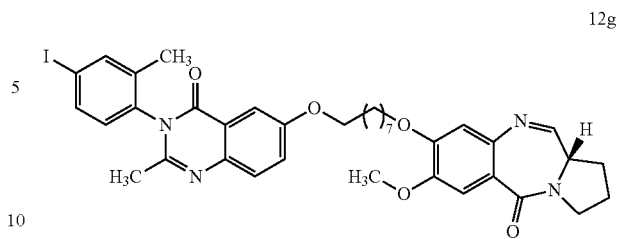

7-methoxy-8-{8-[3-(4-iodo-2-methylphenyl)-2-methyl-4-oxo-34-dihydro-6-quinazolinyl]oxyoctyloxy}-(11aS)-1,2,3,11a-tetrahydro-5H-pyrrolo[2,1-c][1,4]benzodiazepine-5-one (12g);

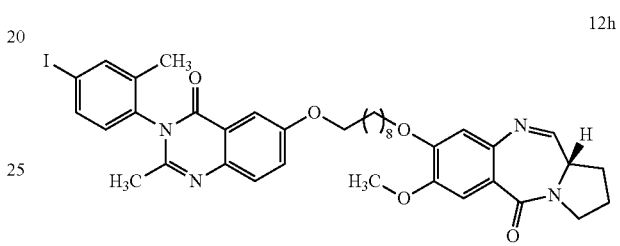

7-methoxy-8-{9-[3-(4-iodo-2-methylphenyl)-2-methyl-4-oxo-34-dihydro-6-quinazolinyl]oxynonyloxy}-(11aS)-1,2,3,11a-tetrahydro-5H-pyrrolo[2,1-c][1,4]benzodiazepine-5-one (12h);

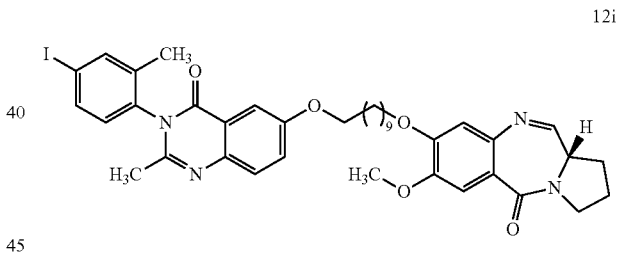

7-methoxy-8-{10-[3-(4-iodo-2-methylphenyl)-2-methyl-4-oxo-34-dihydro-6-quinazolinyl]oxydecyloxy}-(11aS)-1,2,3,11a-tetrahydro-5H-pyrrolo[2,1-c][1,4]benzodiazepine-5-one (12i);

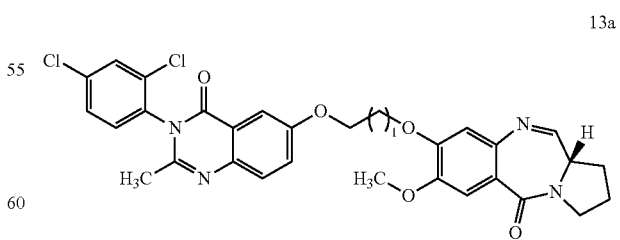

7-methoxy-8-{2-[3-(2,4-dichlorophenyl)-2-methyl-4-oxo-3,4-dihydro-6-quinazolinyl]oxyethoxy}-(11aS)-1,2,3,11a-tetrahydro-5H-pyrrolo[2,1-c][1,4]benzodiazepine-5-one (13a);

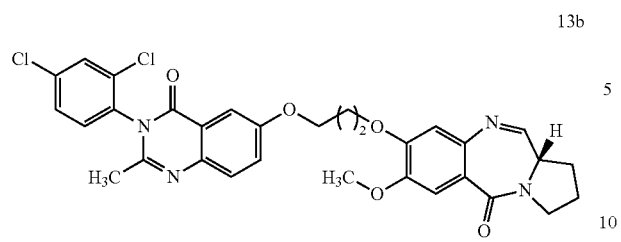

7-methoxy-8-{3-[3-(2,4-dichlorophenyl)-2-methyl-4-oxo-3,4-dihydro-6-quinazolinyl]oxypropoxy}-(11aS)-1,2,3,11a-tetrahydro-5H-pyrrolo[2,1-c][1,4]benzodiazepine-5-one (13b);

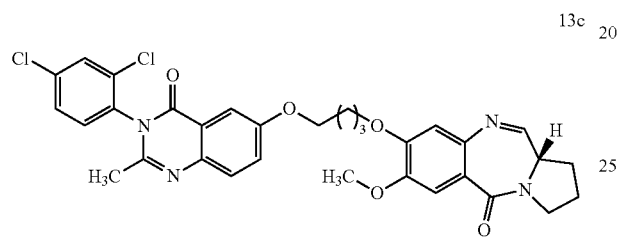

7-methoxy-8-{4-[3-(2,4-dichlorophenyl)-2-methyl-4-oxo-3,4-dihydro-6-quinazolinyl]oxybutoxy}-(11aS)-1,2,3,11a-tetrahydro-5H-pyrrolo[2,1-c][1,4]benzodiazepine-5-one (13c);

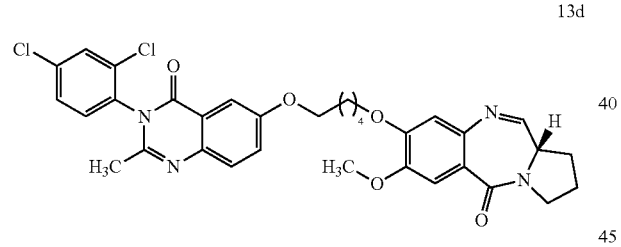

7-methoxy-8-{5-[3-(2,4-dichlorophenyl)-2-methyl-4-oxo-3,4-dihydro-6-quinazolinyl]oxypentyloxy}-(11aS)-1,2,3,11a-tetrahydro-5H-pyrrolo[2,1-c][1,4]benzodiazepine-5-one (13d);

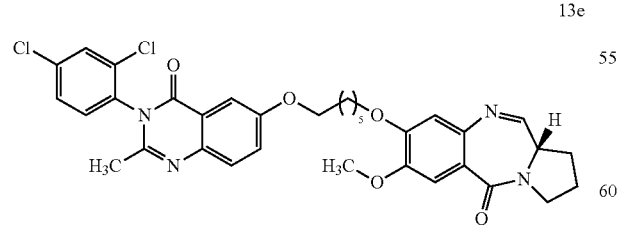

7-methoxy-8-{5-[3-(2,4-dichlorophenyl)-2-methyl-4-oxo-3,4-dihydro-6-quinazolinyl]oxyhexyloxy}-(11aS)-1,2,3,11a-tetrahydro-5H-pyrrolo[2,1-c][1,4]benzodiazepine-5-one (13e);

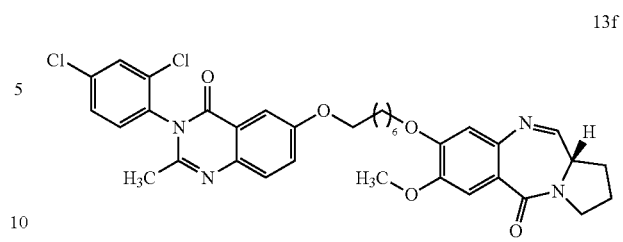

7-methoxy-8-{7-[3-(2,4-dichlorophenyl)-2-methyl-4-oxo-3,4-dihydro-6-quinazolinyl]oxyheptyloxy}-(11aS)-1,2,3,11a-tetrahydro-5H-pyrrolo[2,1-c][1,4]benzodiazepine-5-one (13f);

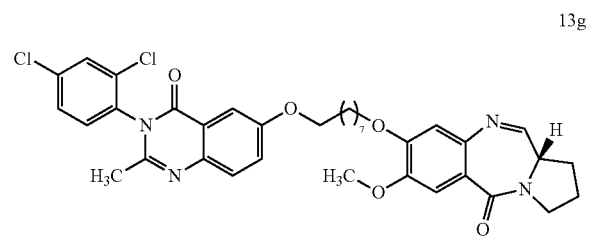

7-methoxy-8-{8-[3-(2,4-dichlorophenyl)-2-methyl-4-oxo-3,4-dihydro-6-quinazolinyl]oxyoctyloxy}-(11aS)-1,2,3,11a-tetrahydro-5H-pyrrolo[2,1-c][1,4]benzodiazepine-5-one (13g);

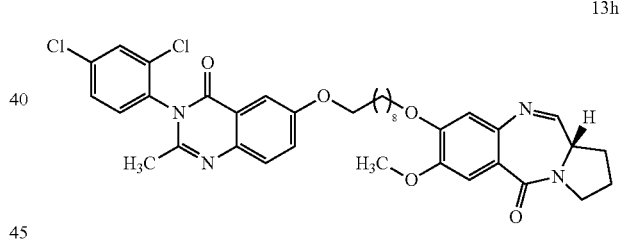

7-methoxy-8-{9-[3-(2,4-dichlorophenyl)-2-methyl-4-oxo-3,4-dihydro-6-quinazolinyl]oxynonyloxy}-(11aS)-1,2,3,11a-tetrahydro-5H-pyrrolo[2,1-c][1,4]benzodiazepine-5-one (13h);

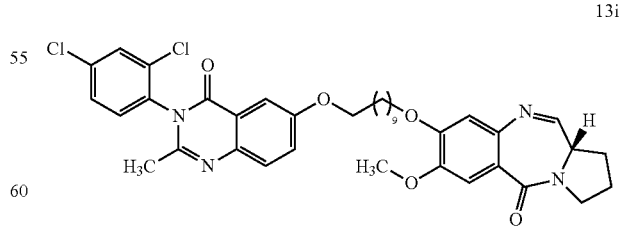

7-methoxy-8-{10-[3-(2,4-dichlorophenyl)-2-methyl-4-oxo-3,4-dihydro-6-quinazolinyl]oxydecyloxy}-(11aS)-1,2,3,11a-tetrahydro-5H-pyrrolo[2,1-c][1,4]benzodiazepine-5-one (13i);

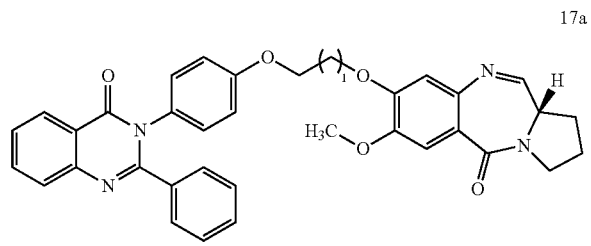

7-(methoxy)-8-[(2-[4-(4-oxo-2-phenyl-3,4-dihydro-3-quinazolinyl)phenyl]oxyethyl)oxy]-(11aS)-1,2,3,11a-tetrahydro-5H-[pyrrolo[2,1-c][1,4]benzodiazepin-5-one (17a);

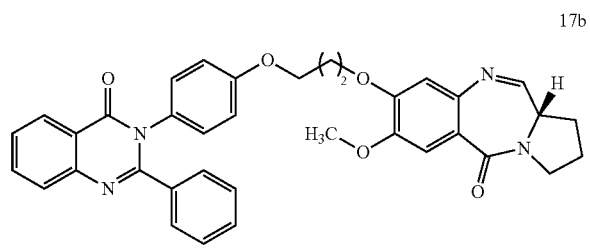

7-(methoxy)-8-[(3-[4-(4-oxo-2-phenyl-3,4-dihydro-3-quinazolinyl)phenyl]oxypropyl)oxy]-(11aS)-1,2,3,11a-tetrahydro-5H-[pyrrolo[2,1-c][1,4]benzodiazepin-5-one (17b);

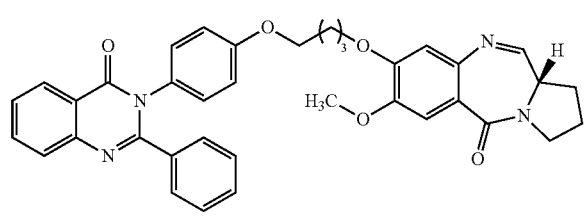

7-(methoxy)-8-[(4-[4-(4-oxo-2-phenyl-3,4-dihydro-3-quinazolinyl)phenyl]oxypropyl)oxy]-(11aS)-1,2,3,11a-tetrahydro-5H-[pyrrolo[2,1-c][1,4]benzodiazepin-5-one (17c);

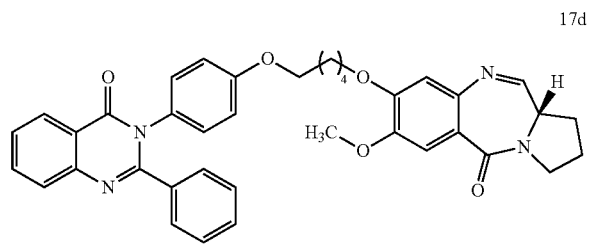

7-(methoxy)-8-[(5-[4-(4-oxo-2-phenyl-3,4-dihydro-3-quinazolinyl)phenyl]oxypentyl)oxy]-(11aS)-1,2,3,11a-tetrahydro-5H-[pyrrolo[2,1-c][1,4]benzodiazepin-5-one (17d);

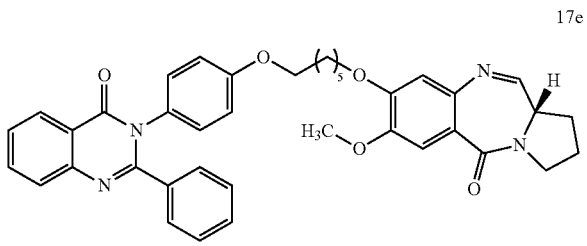

7-(methoxy)-8-[(6-[4-(4-oxo-2-phenyl-3,4-dihydro-3-quinazolinyl)phenyl]oxyhexyl)oxy]-(11aS)-1,2,3,11a-tetrahydro-5H-[pyrrolo[2,1-c][1,4]benzodiazepin-5-one (17e);

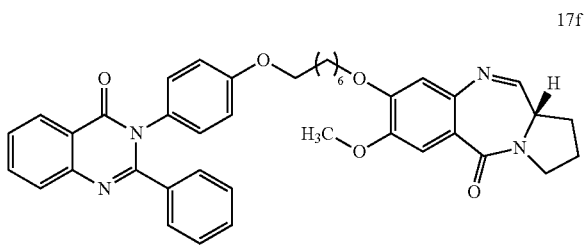

7-(methoxy)-8-[(7-[4-(4-oxo-2-phenyl-3,4-dihydro-3-quinazolinyl)phenyl]oxyheptyl)oxy]-(11aS)-1,2,3,11a-tetrahydro-5H-[pyrrolo[2,1-c][1,4]benzodiazepin-5-one (17f);

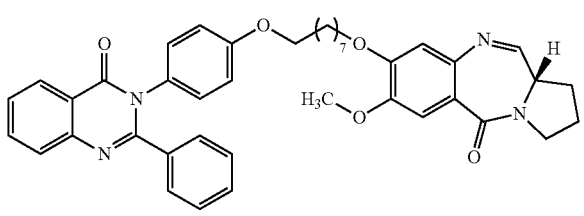

7-(methoxy)-8-[(8-[4-(4-oxo-2-phenyl-3,4-dihydro-3-quinazolinyl)phenyl]oxyoctyl)oxy]-(11aS)-1,2,3,11a-tetrahydro-5H-[pyrrolo[2,1-c][1,4]benzodiazepin-5-one (17g);

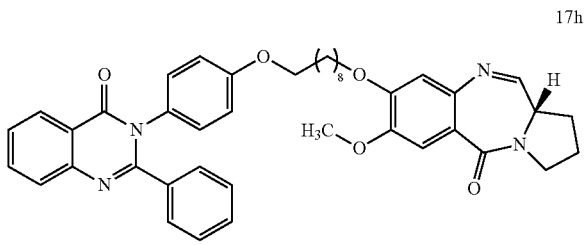

7-(methoxy)-8-[(9-[4-(4-oxo-2-phenyl-3,4-dihydro-3-quinazolinyl)phenyl]oxynonyl)oxy]-(11aS)-1,2,3,11a-tetrahydro-5H-[pyrrolo[2,1-c][1,4]benzodiazepin-5-one (17h);

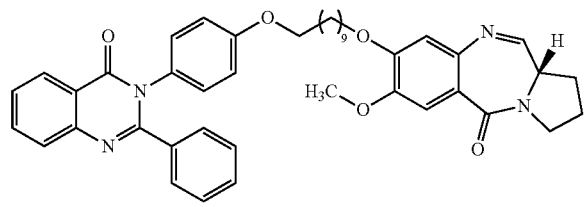

7-(methoxy)-8-[(10-[4-(4-oxo-2-phenyl-3,4-dihydro-3-quinazolinyl)phenyl]oxydecyl)oxy]-(11aS)-1,2,3,11a-tetrahydro-5H-[pyrrolo[2,1-c][1,4]benzodiazepin-5-one (17i);

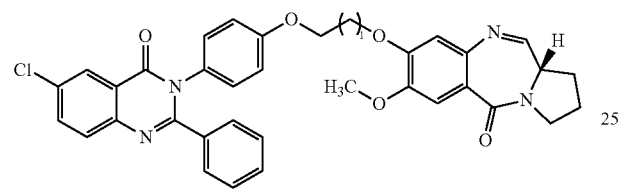

7-methoxy-(8-[(2-[4-(6-chloro-4-oxo-2-phenyl-3,4-dihydro-3-quinazolinyl)phenyl]oxyethyl)oxy]-(11aS)-1,2,3,11a-tetrahydro-5H-pyrrolo[2,1-c][1,4]benzodiazepin-5-one (18a);

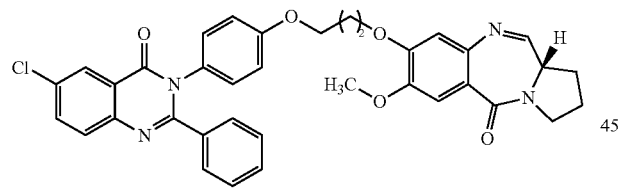

7-methoxy-(8-[(3-[4-(6-chloro-4-oxo-2-phenyl-3,4-dihydro-3-quinazolinyl)phenyl]oxypropyl)oxy]-(11aS)-1,2,3,11a-tetrahydro-5H-pyrrolo[2,1-c][1,4]benzodiazepin-5-one (18b);

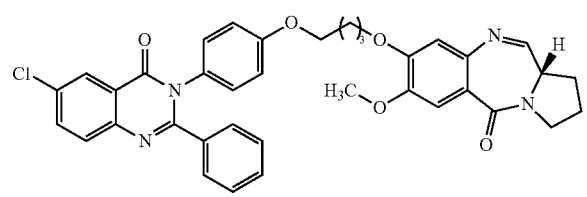

7-methoxy-(8-[(4-[4-(6-chloro-4-oxo-2-phenyl-3,4-dihydro-3-quinazolinyl)phenyl]oxybutyl)oxy]-(11aS)-1,2,3,11a-tetrahydro-5H-pyrrolo[2,1-c][1,4]benzodiazepin-5-one (18c);

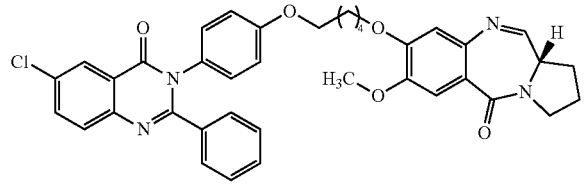

7-methoxy-(8-[(5-[4-(6-chloro-4-oxo-2-phenyl-3,4-dihydro-3-quinazolinyl)phenyl]oxypentyl)oxy]-(11aS)-1,2,3,11a-tetrahydro-5H-pyrrolo[2,1-c][1,4]benzodiazepin-5-one (18d);

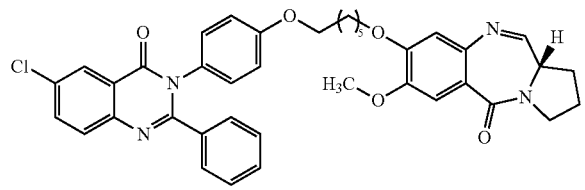

7-methoxy-(8-[(6-[4-(6-chloro-4-oxo-2-phenyl-3,4-dihydro-3-quinazolinyl)phenyl]oxyhexyl)oxy]-(11aS)-1,2,3,11a-tetrahydro-5H-pyrrolo[2,1-c][1,4]benzodiazepin-5-one (18e);

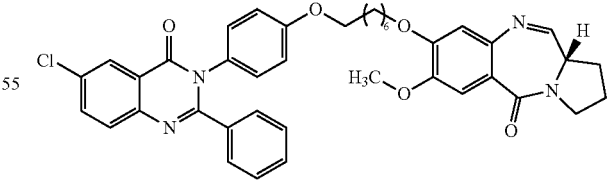

7-methoxy-(8-[(7-[4-(6-chloro-4-oxo-2-phenyl-3,4-dihydro-3-quinazolinyl)phenyl]oxyheptyl)oxy]-(11aS)-1,2,3,11a-tetrahydro-5H-pyrrolo[2,1-c][1,4]benzodiazepin-5-one (18f);

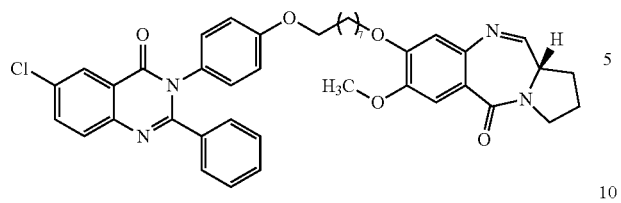

7-methoxy-(8-[(8-[4-(6-chloro-4-oxo-2-phenyl-3,4-dihydro-3-quinazolinyl)phenyl]oxyoctyl)oxy]-(11aS)-1,2,3,11a-tetrahydro-5H-pyrrolo[2,1-c][1,4]benzodiazepin-5-one (18g);

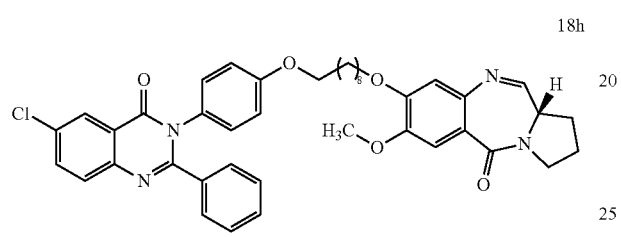

7-methoxy-(8-[(9-[4-(6-chloro-4-oxo-2-phenyl-3,4-dihydro-3-quinazolinyl)phenyl]oxynonyl)oxy]-(11aS)-1,2,3,11a-tetrahydro-5H-pyrrolo[2,1-c][1,4]benzodiazepin-5-one (18h);

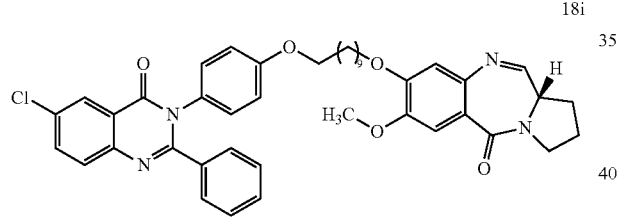

7-methoxy-(8-[(10-[4-(6-chloro-4-oxo-2-phenyl-3,4-dihydro-3-quinazolinyl)phenyl]oxydecyl)oxy]-(11aS)-1,2,3,11a-tetrahydro-5H-pyrrolo[2,1-c][1,4]benzodiazepin-5-one (18i);

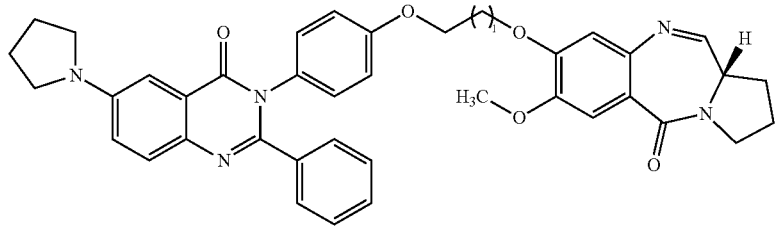

7-methoxy-8-[(2-[4-(4-oxo-2-phenyl-6-tetrahydro-1H-1-pyrrolyl]-3,4-dihydro-3-quinazolinyl)phenyl]oxyethyl)oxy]-(11aS)-1,2,3,11a-tetrahydro-5H-pyrrolo[2,1-c][1,4]benzodiazepin-5-one (19a);

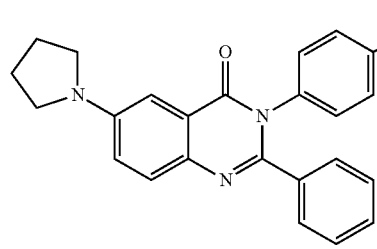

7-methoxy-8-[(3-[4-(4-oxo-2-phenyl-6-tetrahydro-1H-1-pyrrolyl)-3,4-dihydro-3-quinazolinyl)phenyl]oxypropyl)oxy]-(11aS)-1,2,3,11a-tetrahydro-5H-pyrrolo[2,1-c][1,4]benzodiazepin-5-one (19b);

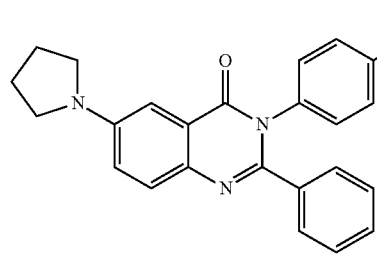

7-methoxy-8-[(4-[4-(4-oxo-2-phenyl-6-tetrahydro-1H-1-pyrrolyl)-3,4-dihydro-3-quinazolinyl)phenyl]oxybutyl)oxy]-(11aS)-1,2,3,11a-tetrahydro-5H-pyrrolo[2,1-c][1,4]benzodiazepin-5-one (19c);

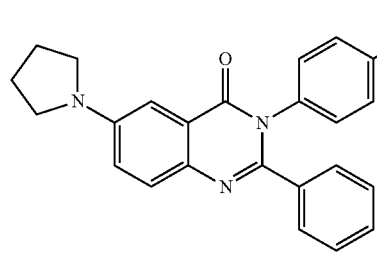

7-methoxy-8-[(5-[4-(4-oxo-2-phenyl-6-tetrahydro-1H-1-pyrrolyl)-3,4-dihydro-3-quinazolinyl)phenyl]oxypentyl)oxy]-(11aS)-1,2,3,11a-tetrahydro-5H-pyrrolo[2,1-c][1,4]benzodiazepin-5-one (19d);

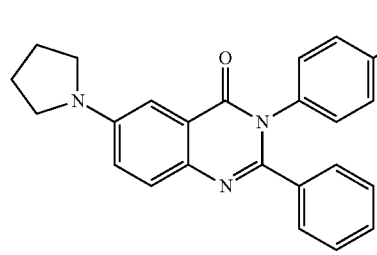

7-methoxy-8-[(6-[4-(4-oxo-2-phenyl-6-tetrahydro-1H-1-pyrrolyl)-3,4-dihydro-3-quinazolinyl)phenyl]oxyhexyl)

oxy]-(11aS)-1,2,3,11a-tetrahydro-5H-pyrrolo[2,1-c][1,4]benzodiazepin-5-one (19e);

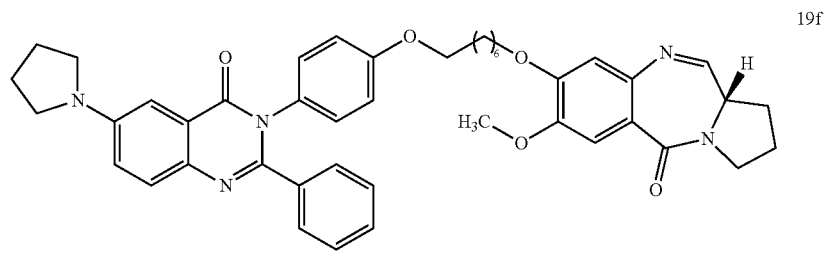

7-methoxy-8-[(7-[4-(4-oxo-2-phenyl-6-tetrahydro-1H-1-pyrrolyl-3,4-dihydro-3-quinazolinyl)phenyl]oxyheptyl)oxy]-(11aS)-1,2,3,11a-tetrahydro-5H-pyrrolo[2,1-c][1,4]benzodiazepin-5-one (19f);

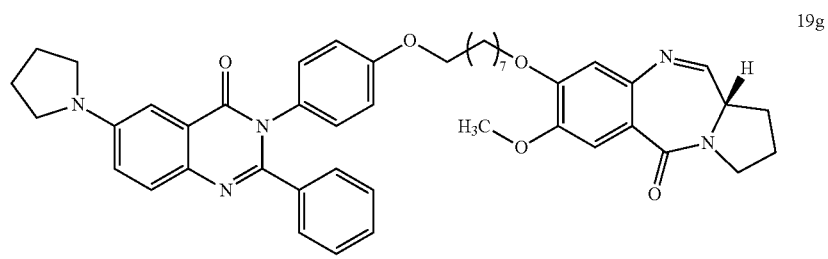

7-methoxy-8-[(8-[4-(4-oxo-2-phenyl-6-tetrahydro-1H-1-pyrrolyl-3,4-dihydro-3-quinazolinyl)phenyl]oxyoctyl)oxy]-(11aS)-1,2,3,11a-tetrahydro-5H-pyrrolo[2,1-c][1,4]benzodiazepin-5-one (19g);

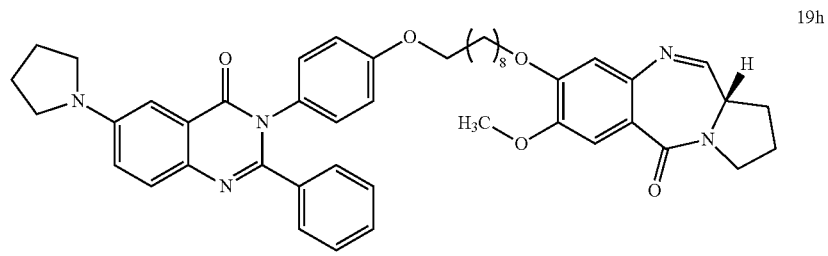

7-methoxy-8-[(9-[4-(4-oxo-2-phenyl-6-tetrahydro-1H-1-pyrrolyl-3,4-dihydro-3-quinazolinyl)phenyl]oxynonyl)oxy]-(11aS)-1,2,3,11a-tetrahydro-5H-pyrrolo[2,1-c][1,4]benzodiazepin-5-one (19h);

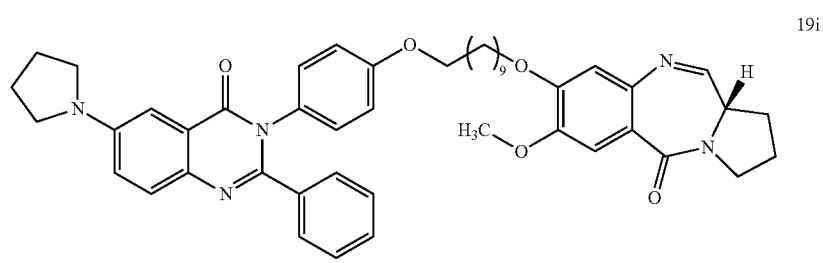

7-methoxy-8-[(10-[4-(4-oxo-2-phenyl-6-tetrahydro-1H-1-pyrrolyl-3,4-dihydro-3-quinazolinyl)phenyl]oxydecyl)oxy]-(11aS)-1,2,3,11a-tetrahydro-5H-pyrrolo[2,1-c][1,4]benzodiazepin-5-one (19i);

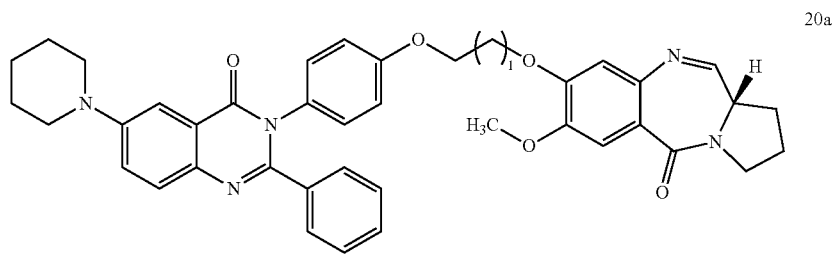

7-methoxy-8-[(2-[4-(6-hexahydro-1-pyridinyl-4-oxo-2-phenyl-3,4-dihydro-3-quinazolinyl)phenyl]oxyethyl)oxy]-(11aS))-1,2,3,11a-tetrahydro-5H-pyrrolo[2,1-c][1,4]benzodiazepin-5-one (20a);

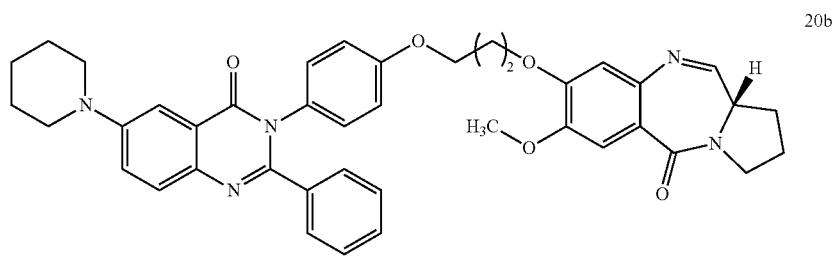

7-methoxy-8-[(3-[4-(6-hexahydro-1-pyridinyl-4-oxo-2-phenyl-3,4-dihydro-3-quinazolinyl)phenyl]oxypropyl)oxy]-(11aS))-1,2,3,11a-tetrahydro-5H-pyrrolo[2,1-c][1,4]benzodiazepin-5-one (20b);

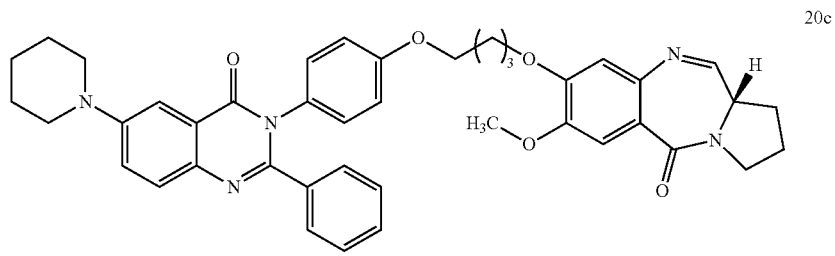

7-methoxy-8-[(4-[4-(6-hexahydro-1-pyridinyl-4-oxo-2-phenyl-3,4-dihydro-3-quinazolinyl)phenyl]oxybutyl)oxy]-(11aS))-1,2,3,11a-tetrahydro-5H-pyrrolo[2,1-c][1,4]benzodiazepin-5-one (20c);

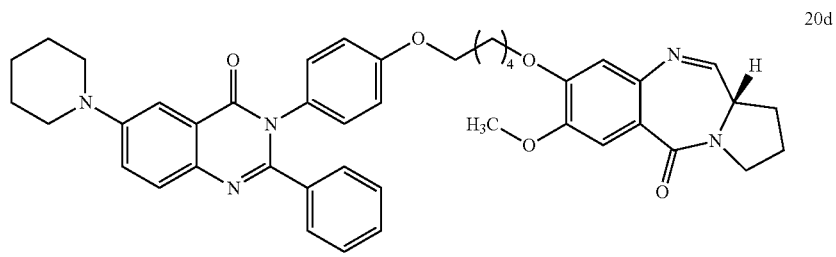

20d 7-methoxy-8-[(5-[4-(6-hexahydro-1-pyridinyl-4-oxo-2-phenyl-3,4-dihydro-3-quinazolinyl)phenyl]oxypentyl)oxy]-(11aS))-1,2,3,11a-tetrahydro-5H-pyrrolo[2,1-c][1,4]benzodiazepin-5-one (20d);

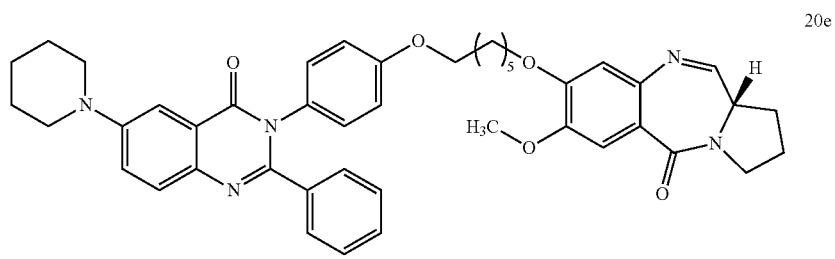

20e 7-methoxy-8-[(6-[4-(6-hexahydro-1-pyridinyl-4-oxo-2-phenyl-3,4-dihydro-3-quinazolinyl)phenyl]oxyhexyl)oxy]-(11aS))-1,2,3,11a-tetrahydro-5H-pyrrolo[2,1-c][1,4]benzodiazepin-5-one (20e);

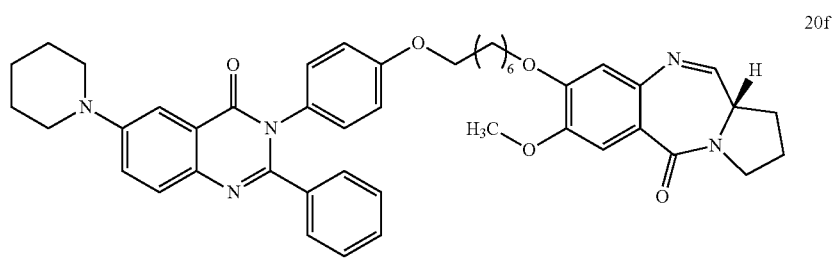

20f 7-methoxy-8-[(7-[4-(6-hexahydro-1-pyridinyl-4-oxo-2-phenyl-3,4-dihydro-3-quinazolinyl)phenyl]oxyheptyl)oxy]-(11aS))-1,2,3,11a-tetrahydro-5H-pyrrolo[2,1-c][1,4]benzodiazepin-5-one (20f);

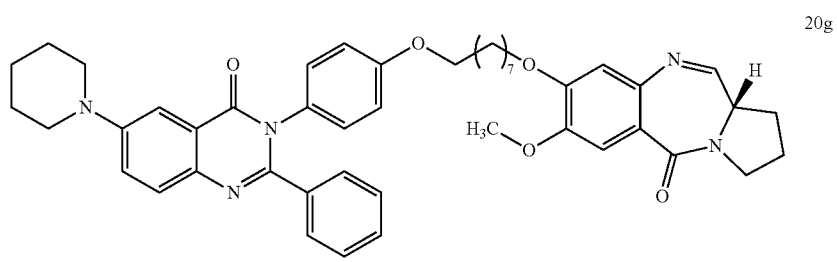

20g 7-methoxy-8-[(8-[4-(6-hexahydro-1-pyridinyl-4-oxo-2-phenyl-3,4-dihydro-3-quinazolinyl)phenyl]oxyoctyl)

oxy]-(11aS))-1,2,3,11a-tetrahydro-5H-pyrrolo[2,1-c][1,4]benzodiazepin-5-one (20g);

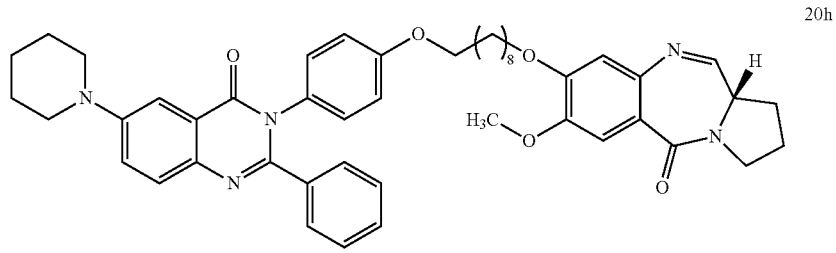

7-methoxy-8-[(9-[4-(6-hexahydro-1-pyridinyl-4-oxo-2-phenyl-3,4-dihydro-3-quinazolinyl)phenyl]oxynonyl)oxy]-(11aS))-1,2,3,11a-tetrahydro-5H-pyrrolo[2,1-c][1,4]benzodiazepin-5-one (20h);

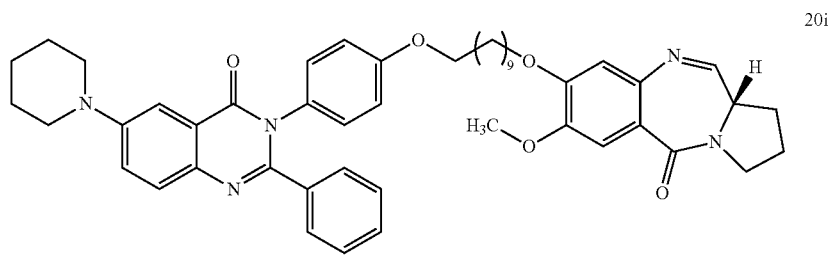

7-methoxy-8-[(10-[4-(6-hexahydro-1-pyridinyl-4-oxo-2-phenyl-3,4-dihydro-3-quinazolinyl)phenyl]oxydecyl)oxy]-(11aS))-1,2,3,11a-tetrahydro-5H-pyrrolo[2,1-c][1,4]benzodiazepin-5-one (20i);

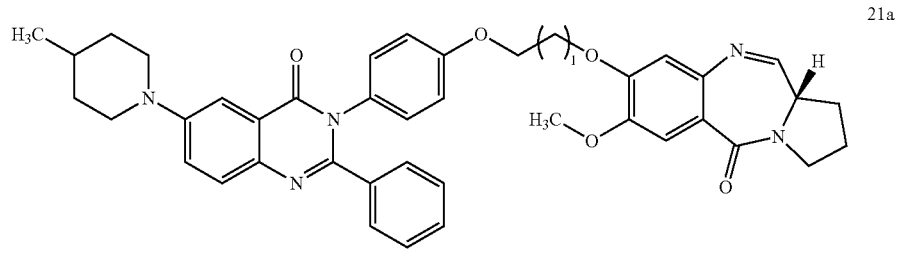

7-methoxy-8-[2-(4-[6-(4-methylhexahydro-1-pyridinyl)-4-oxo-2-phenyl-3,4-dihydro-3-quinazolinyl]phenyloxy)ethyl]oxy-(11aS))-1,2,3,11a-tetrahydro-5H-pyrrolo[2,1-c][1,4]benzodiazepin-5-one (21a);

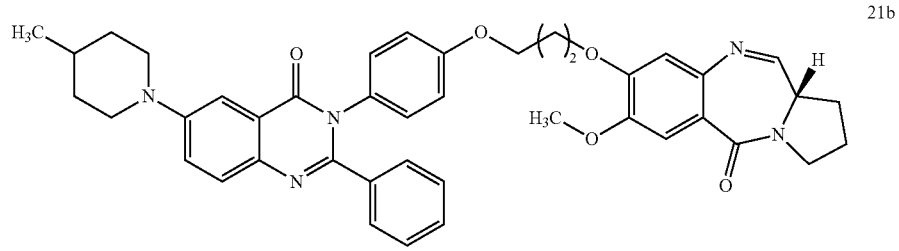

7-methoxy-8-[3-(4-[6-(4-methylhexahydro-1-pyridinyl)-4-oxo-2-phenyl-3,4-dihydro-3-quinazolinyl]phenyloxy)propyl]oxy-(11aS))-1,2,3,11a-tetrahydro-5H-pyrrolo[2,1-c][1,4]benzodiazepin-5-one (21b);

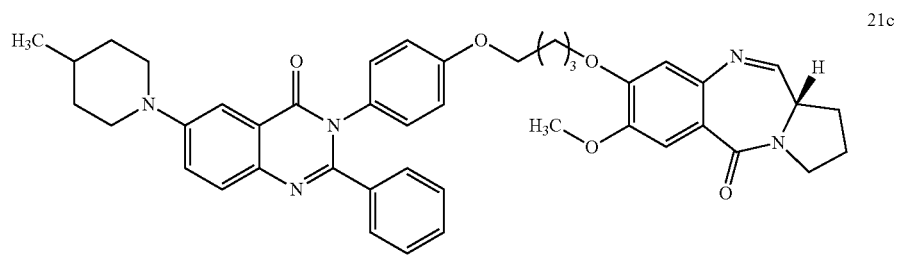

7-methoxy-8-[4-(4-[6-(4-methylhexahydro-1-pyridinyl)-4-oxo-2-phenyl-3,4-dihydro-3-quinazolinyl]phenyloxy)butyl]oxy-(11aS))-1,2,3,11a-tetrahydro-5H-pyrrolo[2,1-c][1,4]benzodiazepin-5-one (21c);

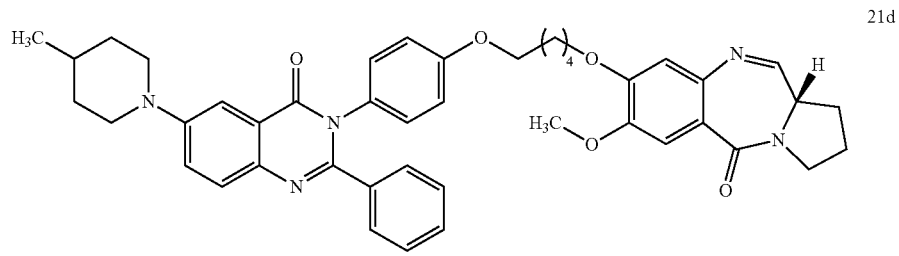

7-methoxy-8-[5-(4-[6-(4-methylhexahydro-1-pyridinyl)-4-oxo-2-phenyl-3,4-dihydro-3-quinazolinyl]phenyloxy)pentyl]oxy-(11aS))-1,2,3,11a-tetrahydro-5H-pyrrolo[2,1-c][1,4]benzodiazepin-5-one (21d);

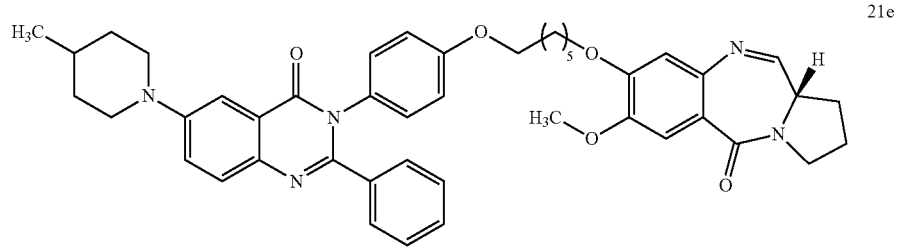

7-methoxy-8-[6-(4-[6-(4-methylhexahydro-1-pyridinyl)-4-oxo-2-phenyl-3,4-dihydro-3-quinazolinyl]phenyloxy)hexyl]oxy-(11aS))-1,2,3,11a-tetrahydro-5H-pyrrolo[2,1-c][1,4]benzodiazepin-5-one (21e);

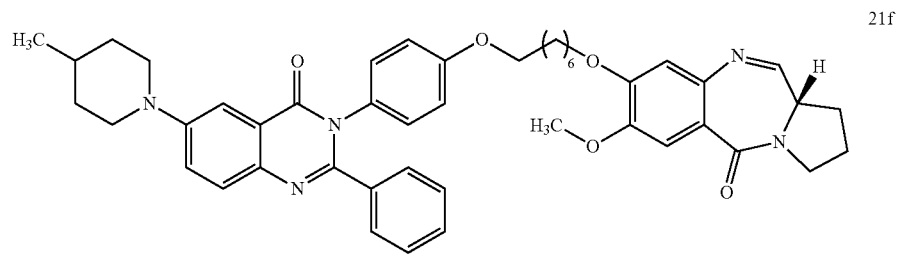

7-methoxy-8-[7-(4-[6-(4-methylhexahydro-1-pyridinyl)-4-oxo-2-phenyl-3,4-dihydro-3-quinazolinyl]phenyloxy)heptyl]oxy-(11aS))-1,2,3,11a-tetrahydro-5H-pyrrolo[2,1-c][1,4]benzodiazepin-5-one (21f);

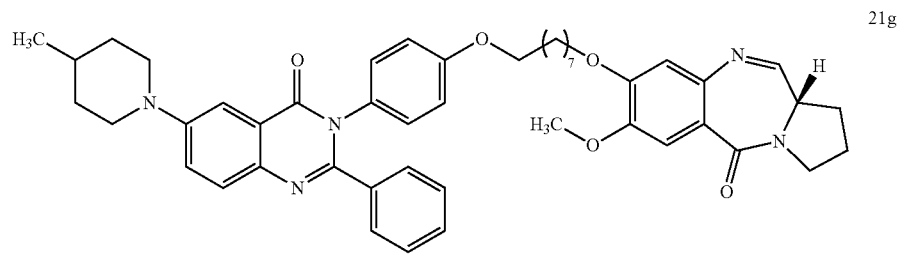

7-methoxy-8-[8-(4-[6-(4-methylhexahydro-1-pyridinyl)-4-oxo-2-phenyl-3,4-dihydro-3-quinazolinyl]phenyloxy)octyl]oxy-(11aS))-1,2,3,11a-tetrahydro-5H-pyrrolo[2,1-c][1,4]benzodiazepin-5-one (21g);

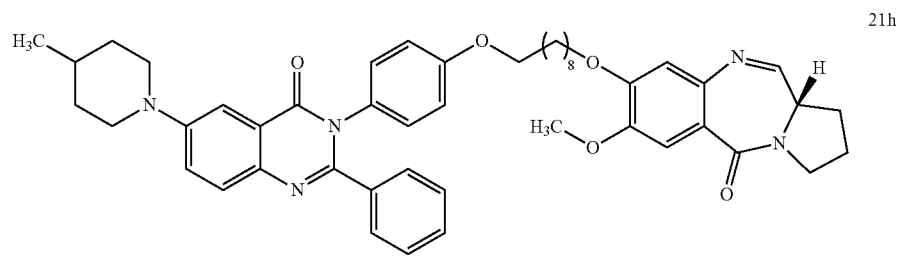

7-methoxy-8-[9-(4-[6-(4-methylhexahydro-1-pyridinyl)-4-oxo-2-phenyl-3,4-dihydro-3-quinazolinyl]phenyloxy)nonyl]oxy-(11aS))-1,2,3,11a-tetrahydro-5H-pyrrolo[2,1-c][1,4]benzodiazepin-5-one (21h);

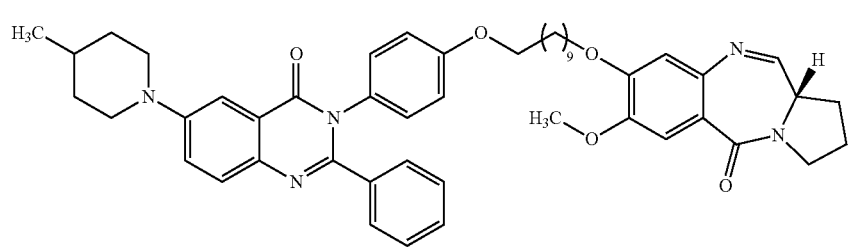

7-methoxy-8-[10-(4-[6-(4-methylhexahydro-1-pyridinyl)-4-oxo-2-phenyl-3,4-dihydro-3-quinazolinyl]phenyloxy)decyl]oxy-(11aS))-1,2,3,11a-tetrahydro-5H-pyrrolo[2,1-c][1,4]benzodiazepin-5-one (21i);

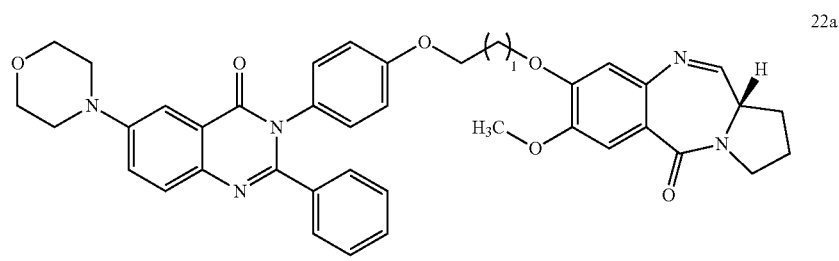

7-methoxy-8-[2-(4-[6-(1,4-oxazinan-4-yl)-4-oxo-2-phenyl-3,4-dihydro-3-quinazolinyl]phenyloxy)ethyl]oxy]-(11aS))-1,2,3,11a-tetrahydro-5H-pyrrolo[2,1-c][1,4]benzodiazepin-5-one (22a);

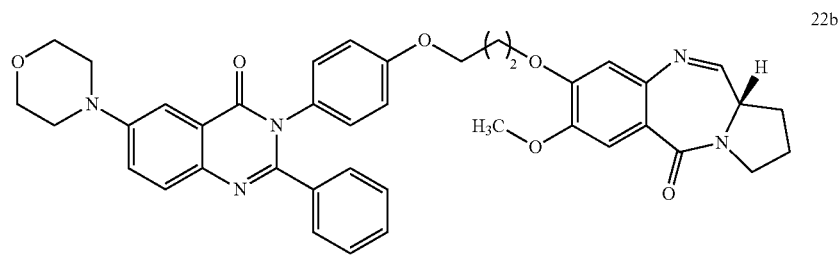

7-methoxy-8-[3-(4-[6-(1,4-oxazinan-4-yl)-4-oxo-2-phenyl-3,4-dihydro-3-quinazolinyl]phenyloxy)propyl]oxy]-(11aS))-1,2,3,11a-tetrahydro-5H-pyrrolo[2,1-c][1,4]benzodiazepin-5-one (22b);

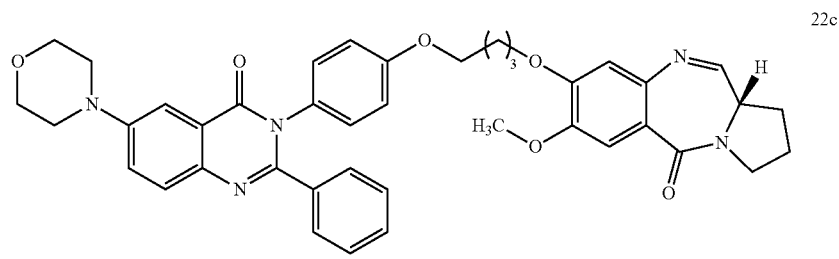

7-methoxy-8-[4-(4-[6-(1,4-oxazinan-4-yl)-4-oxo-2-phenyl-3,4-dihydro-3-quinazolinyl]phenyloxy)butyl]oxy]-(11aS))-1,2,3,11a-tetrahydro-5H-pyrrolo[2,1-c][1,4]benzodiazepin-5-one (22c);

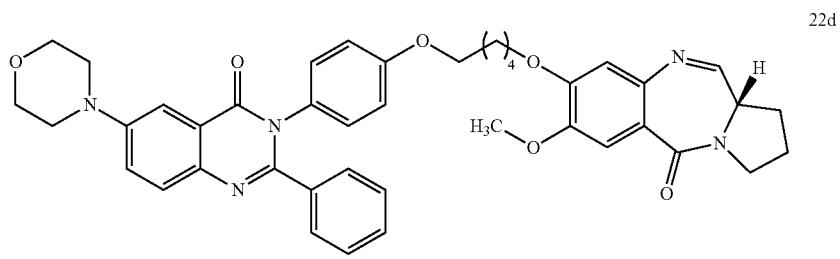

7-methoxy-8-[5-(4-[6-(1,4-oxazinan-4-yl)-4-oxo-2-phenyl-3,4-dihydro-3-quinazolinyl]phenyloxy)pentyl]oxy]-(11aS))-1,2,3,11a-tetrahydro-5H-pyrrolo[2,1-c][1,4]benzodiazepin-5-one (22d);

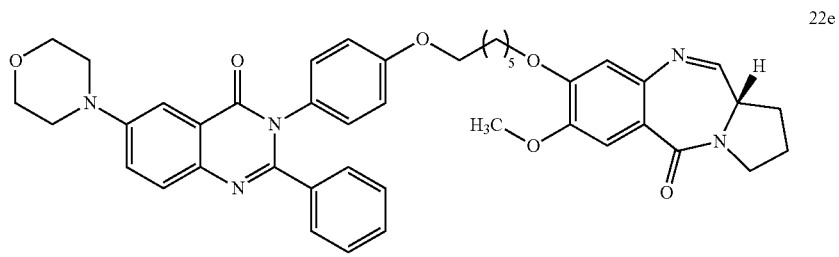

7-methoxy-8-[6-(4-[6-(1,4-oxazinan-4-yl)-4-oxo-2-phenyl-3,4-dihydro-3-quinazolinyl]phenyloxy)hexyl]oxy]-(11aS))-1,2,3,11a-tetrahydro-5H-pyrrolo[2,1-c][1,4]benzodiazepin-5-one (22e);

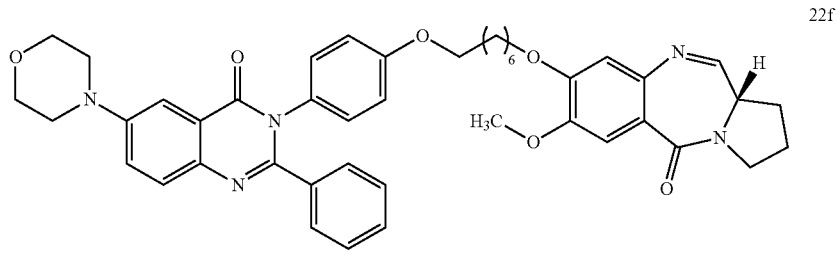

7-methoxy-8-[7-(4-[6-(1,4-oxazinan-4-yl)-4-oxo-2-phenyl-3,4-dihydro-3-quinazolinyl]phenyloxy)heptyl]oxy]-(11aS))-1,2,3,11a-tetrahydro-5H-pyrrolo[2,1-c][1,4]benzodiazepin-5-one (22f);

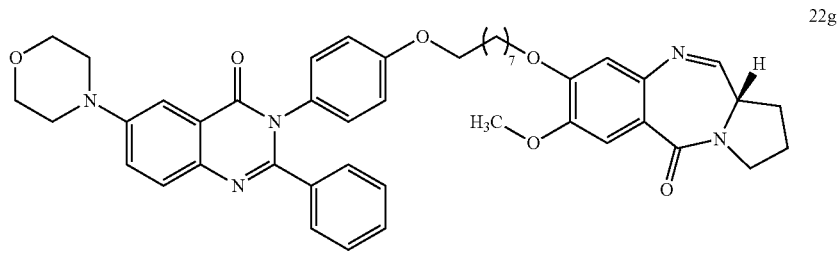

7-methoxy-8-[8-(4-[6-(1,4-oxazinan-4-yl)-4-oxo-2-phenyl-3,4-dihydro-3-quinazolinyl]phenyloxy)octyl]oxy]-(11aS))-1,2,3,11a-tetrahydro-5H-pyrrolo[2,1-c][1,4]benzodiazepin-5-one (22g);

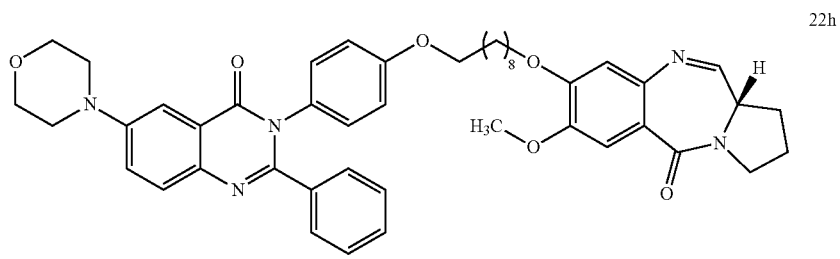

7-methoxy-8-[9-(4-[6-(1,4-oxazinan-4-yl)-4-oxo-2-phenyl-3,4-dihydro-3-quinazolinyl]phenyloxy)nonyl]oxy]-(11aS))-1,2,3,11a-tetrahydro-5H-pyrrolo[2,1-c][1,4]benzodiazepin-5-one (22h)

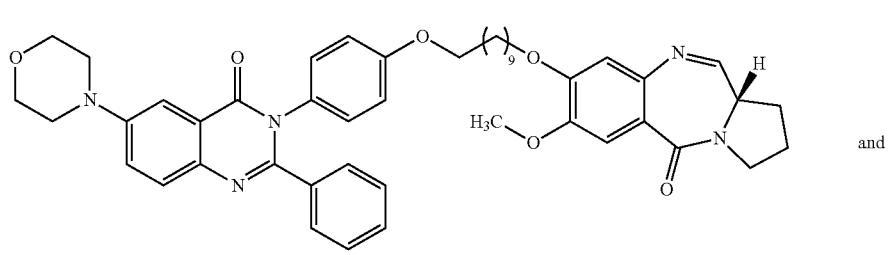

7-methoxy-8-[10-(4-[6-(1,4-oxazinan-4-yl)-4-oxo-2-phenyl-3,4-dihydro-3-quinazolinyl]phenyloxy)decyl]oxy]-(11aS))-1,2,3,11a-tetrahydro-5H-pyrrolo[2,1-c][1,4]benzodiazepin-5-one (22i).

3. A process for the preparation of a compound of formula A

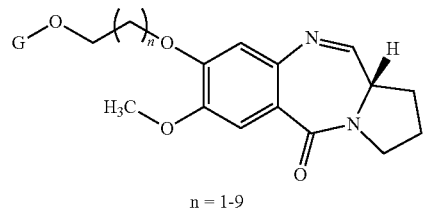

Formula A n = 1-9 wherein G =

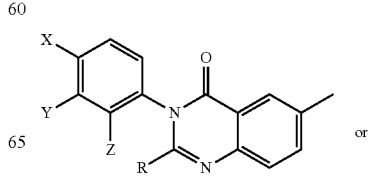

or

-continued

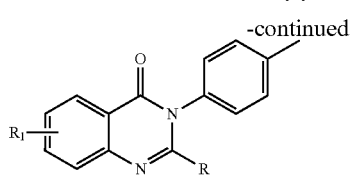

R = Methyl, styryl, phenyl;
R₁ = H, halo, pyrrolidine, piperidine, 4-methyl piperidine or morpholine;
X, Y, Z = H, halo, alkyl or alkoxy and the process comprising the steps of:
a) reacting (2S)—N-[(n-bromoalkyloxy)-5-methoxy-2-nitrobenzoyl)]pyrrolidine-2-carboxaldehyde diethylthioacetal of formula 1a-i with quinazolinones of formulae 2, 6 and 14, isolating the nitro compounds of formulae 3a-r, 7a-i and 15a-I,

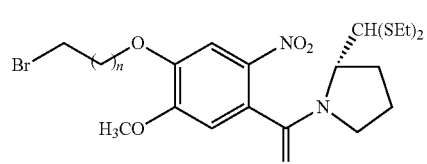

1a-i

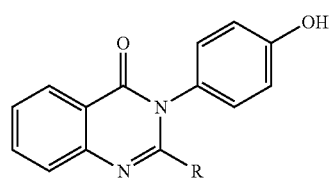

2

R = methyl, styryl

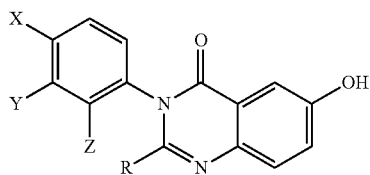

6

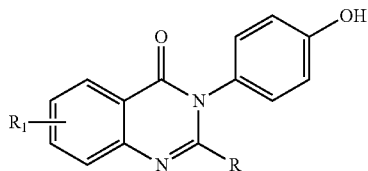

14

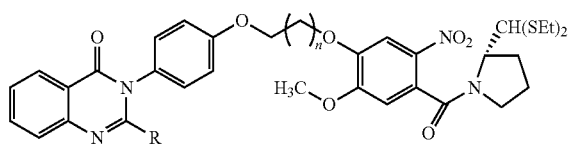

3a-r

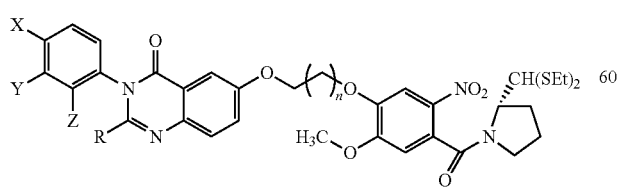

7a-i

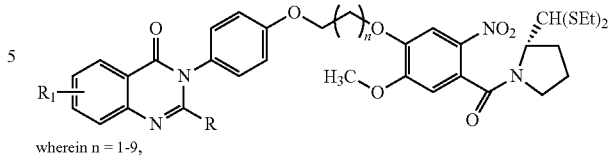

15a-i wherein n = 1-9,

X, Y and Z are independently selected from hydrogen, halo, alkyl or alkoxyl b) reducing the above nitro compounds of formulae 3a-r, 7a-i and 15a-i with $SnCl_2 \cdot 2H_2O$ in presence of organic solvent like methanol or ethanol up to a reflux temperature, isolating the amino compounds of formulae 4a-r, 8a-i and 16a-I,

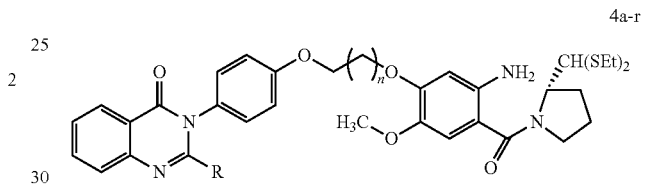

4a-r 8a-i 16a-i wherein n = 1-9,

R is methyl or styryl, R1 is hydrogen, halo, pyrrolidine, piperidine, morpholine and 4-methyl piperidine, X, Y and Z are independently selected from hydrogen, halo, alkyl or alkoxy; and c) reacting the above amino compounds of formula 4a-r, 8a-i and 16a-i with deprotecting agents to give the compound of formula A.

4. The process as claimed in claim 3 wherein the deprotecting agent used in step (c) is $HgCl_2$—$CaCO_3$ and $CH_3CN$—$H_2O$ in ratio of 4:1.

* * * * *